United States Patent
Agreda Navajas et al.

(10) Patent No.: US 9,440,966 B2
(45) Date of Patent: Sep. 13, 2016

(54) COMPOUNDS FOR TREATMENT OF METABOLIC SYNDROME

(75) Inventors: Juan Carlos Agreda Navajas, Vitoria (ES); Roberto Mikio Kassuya, Vitoria (BR)

(73) Assignee: SJT MOLECULAR RESEARCH, S.L., Vitoria (ES)

( * ) Notice: Subject to any disclaimer, the term of this patent is extended or adjusted under 35 U.S.C. 154(b) by 0 days.

(21) Appl. No.: 14/007,868

(22) PCT Filed: Mar. 28, 2012

(86) PCT No.: PCT/EP2012/055570
§ 371 (c)(1),
(2), (4) Date: Dec. 10, 2013

(87) PCT Pub. No.: WO2012/130912
PCT Pub. Date: Oct. 4, 2012

(65) Prior Publication Data
US 2015/0051204 A1     Feb. 19, 2015

Related U.S. Application Data

(60) Provisional application No. 61/468,163, filed on Mar. 28, 2011.

(51) Int. Cl.
| | | |
|---|---|---|
| C07D 241/04 | (2006.01) |
| A61K 31/437 | (2006.01) |
| C07D 471/04 | (2006.01) |
| A23L 1/29 | (2006.01) |
| A23L 1/30 | (2006.01) |
| A61K 8/49 | (2006.01) |
| A61K 8/69 | (2006.01) |
| A61Q 19/06 | (2006.01) |

(52) U.S. Cl.
CPC ............. *C07D 471/04* (2013.01); *A23L 1/293* (2013.01); *A23L 1/30* (2013.01); *A61K 8/4926* (2013.01); *A61K 8/69* (2013.01); *A61K 31/437* (2013.01); *A61Q 19/06* (2013.01); *C07D 241/04* (2013.01); *A23V 2002/00* (2013.01); *A61K 2800/92* (2013.01)

(58) Field of Classification Search
CPC ..... C07D 471/04; A61K 8/49; A61K 31/437
See application file for complete search history.

(56) References Cited

U.S. PATENT DOCUMENTS

2010/0087415 A1    4/2010  Whitten et al.
2010/0173931 A1    7/2010  Ellies et al.

FOREIGN PATENT DOCUMENTS

| BE | 612725 A1 | 7/1962 |
| GB | 975835 | 11/1964 |
| WO | 2010080756 A2 | 7/2010 |

OTHER PUBLICATIONS

International Search Report, Jul. 3, 2012.
Al-Awadi, F.M., et al.; "On the mechanism of the hypoglycaemic effect of a plant extract," Diabetologia, 1985, pp. 432-434, vol. 28.
Nazari Formagio, Anelise S., et al.; "Synthesis and antiviral activity of beta-carboline derivatives bearing a substituted carbohydrazide at C-3 against poliovirus and herpes simples virus (HSV-1)," European Journal of Medicinal Chemistry, 2009, pp. 4695-4701, vol. 44.
Cai, Wen, et al.; "Synthesis, methabolism and in vitro cytotoxicity studies on novel lavendamycin antitumor agents," Bioorganic & Medicinal Chemistry, 2010, pp. 1899-1909, vol. 18.
Crunkhorn, Sarah; "Birch bark compound combats metabolic syndrome," Nature Reviews, Drug Discovery 2011, p. 172, vol. 10.
Nazari Formagio, Anelise S., et al.; Synthesis and antitumoral activity of novel 3-(2-substituted-1,3,4-oxadiazol-5-yl) and 3-(5-substituted-1,2,4-triazol-3-yl) beta-carboline derivaties, Bioorganic & Medicinal Chemistry, 2008, pp. 9660-9667, vol. 16.
Grundy, Scott M.; "Drug therapy of the metabolic syndrome: minimizing the emerging crisis in polypharmacy," Nature Review, Drug Discovery, 2006, pp. 295-309, vol. 5.
Molina, Pedro, et al.; "Inninophosphorane-Mediated Syntheses of the Fascaplysin Alkaloid of Marine Origin and Nitramarine," Tetrahedron Letters, 1994, pp. 8851-8854, vol. 35.
Abdel-Moty, SG, et al.; "Synthesis of cytotoxic 1-polyhydroxyalkyl-Beta-carboline derivatives," European Journal of Medicinal Chemistry, 1997, pp. 1009-1017, vol. 32.
Panarese, Joseph D., et al.; "Room-Temperature Aromatization of Tetrahydro-Beta-carbolines by 2-Iodoxybenzoic Acid: Utility in a Total Synthesis of Eudistomin U," Organic Letters, 2010, pp. 4086-4089, vol. 12.
Düsman Tonin, Lilian T., et al.; "Antitrypanosomal and antileishmanial activities of novel N-alkyl0(1-phenylsubstituted-Beta-carboline)-3-carboxamides," Biomedicine & Pharmacotherapy, 2010, pp. 386-389, vol. 64.
Trinder, P.; "Determination of blood glucose using an oxidase-peroxidase system with a non-carcinogenic chromogen," J. of Clin. Path.,1969, pp. 158-161, vol. 22.
Gross, Jorge L., et al.; "Diabetes Mellitus: Diagnosis, Classification and Glucose Control Evaluation," Arq Bras Endocrinol Metab, 2002, pp. 16-26, vol. 46; and English Abstract.
Srivastava, Sanjay K., et al.; "Potent 1,3-Disubstituted-9 H-pyrido[3,4-b]indoles as New Lead Compounds in Antifilarial Chemotherapy," Bioorganic & Medicinal Chemistry, 1999, pp. 1223-1236, vol. 7.
Database CA [Online]; Chemical Abstracts Service, Zhang, Jing Xin et al.: "Solid phase synthesis of .beta.-carbolines," XP002678192; Database accession No. 2000:825550.

*Primary Examiner* — Rita Desai
(74) *Attorney, Agent, or Firm* — Sterne, Kessler, Goldstein & Fox P.L.L.C.

(57) ABSTRACT

Present invention refers to new compounds of formula I or II, its synthesis and its use in the treatment of metabolic syndrome, particularly for the treatment of type I or type II diabetes and/or metabolic syndrome or metabolic disease or metabolic disorders.

2 Claims, 5 Drawing Sheets

A

B

A

B

COMPOUNDS FOR TREATMENT OF METABOLIC SYNDROME

CROSS-REFERENCE TO RELATED APPLICATIONS

Figure 1:
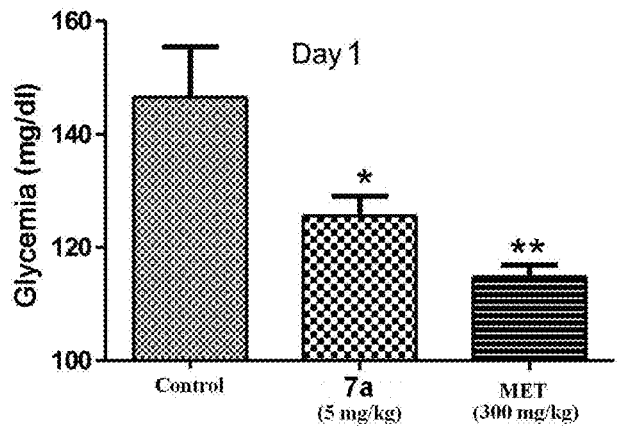
Figure 1:
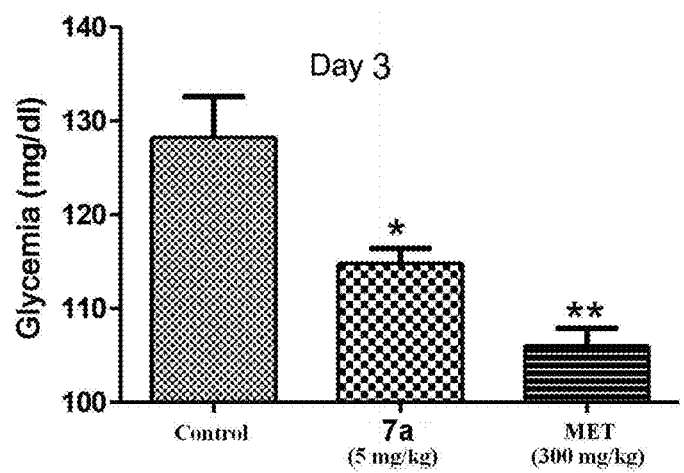

This application is filed under the provisions of 35 U.S.C. §371 and claims the priority of International Patent Application No. PCT/EP2012/055570 filed on 28 Mar. 2012 entitled "COMPOUNDS FOR TREATMENT OF METABOLIC SYNDROME" in the name of Juan Carlos AGREDA NAVAJAS, et al, which claims priority to U.S. Provisional Patent Application No. 61/468,163, filed on 28 Mar. 2011, both of which are hereby incorporated by reference herein in their entirety.

FIELD OF THE INVENTION

The present invention refers to new β-carbolinic compounds and its use for the treatment of metabolic diseases such as metabolic syndrome, type I and II diabetes.

INVENTION BACKGROUND

β-carbolinics compounds comprises a class of indol alkaloids, natural and synthetic, that present a wide range of important biological and pharmacological properties, such as antimicrobial and antiviral activities, action on metabolism and as powerful antitumorigenic agents (1, 2). Several researches have been developed for obtaining β-carbolinic alkaloid derivatives, with different replacements in 1, 3 and 9 positions of the β-carbolinic skeleton. Thus, present invention relates to the synthesis of new β-carbolinics derivatives useful for the treatment of metabolic syndrome and, particularly to the treatment of diabetes, which show improved therapeutically activity in comparison with similar compounds existing in the prior art, even at lower doses. The metabolic syndrome represents a collection of factors, such as hypertension, obesity, hyperlipidemia and diabetes (3), among others, associated with increased risk for cardiovascular disease. Metabolic syndrome is becoming increasingly common, largely as a result of the increase in the prevalence of obesity (4). Although it is generally agreed that first-line clinical intervention for the metabolic syndrome is lifestyle change, this is insufficient to normalize the risk factors in many patients, and so residual risk could be high enough to justify drug therapy. There is growing interest in therapeutic strategies that might target multiple risk factors more effectively, thereby minimizing problems with polypharmacy (3, 4).

DESCRIPTION OF THE INVENTION

The invention comprises the compounds of general formula I and any pharmaceutically, cosmetically or food grade acceptable salt thereof:

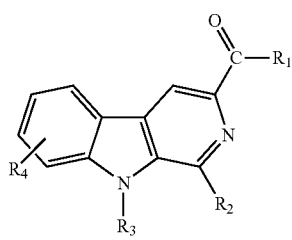

wherein, independently, $R_1$ can selected from: linear or cycled mono or dialkylamines; aminoalkylalcohols or aminoalkylethers;

$R_2$ can be selected from: benzene or heterocycle rings;

$R_3$ can be selected from: H; a hydrocarbon radical selected from straight or branched alkyl of from 1 to 5 carbons; or benzyl group;

$R_4$ can be selected from: H; a hydrocarbon radical selected from straight or branched alkyl of from 1 to 5 carbons; hydroxy or alkoxy radicals; or halogen.

Preferred compounds according to general formula I are those that, independently, $R_1$ when being a linear alkylamine is selected from: $NH-(CH_2)_n-NH_2$; $NH-(CH_2)_n-R_6$, being n a value between 0 and 4; $NH-N=CH$-phenyl-$R_7$;

and $R_1$ when being a cycled amine is selected from:

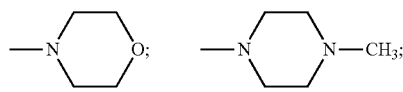

$R_1$ when being an aminoalkylalcohol group is $HNCH_2CH_2OH$; and when being an aminoalkylether group is $HNCH_2CH_2OCH_3$ $R_2$, when being a benzene substituted ring is selected from:

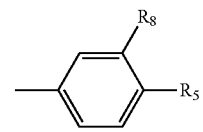

and when being a heterocycle ring is

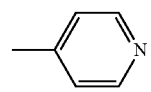

$R_3$ when being a hydrocarbon radical selected from straight alkyl of from 1 to 5 carbons, is methyl;

$R_4$ when being a hydrocarbon radical selected from straight alkyl of from 1 to 5 carbons, is methyl; $R_4$ when being an alkoxy radical is a radical methoxy;

and $R_4$ when being a halogen is fluorine;

$R_5$ can be selected from: H; alkoxy; halogen; hydroxy; or halogen-alkyl;

$R_6$ can be selected from: an alkyl, hydroxy or alkoxy moiety;

$R_7$ can be selected from: H or $NO_2$;

$R_8$ can be selected from: H; hydroxy; alkoxy;

Preferred compounds are those wherein, $R_5$ can be selected from: methoxy; chlorine, OH or trifluormethyl, preferably, when $R_5$ is H, $R_8$ is OH and when $R_5$ is OH, $R_8$ is $OCH_3$.

Preferred compounds are those wherein, wherein $R_6$ is selected from: OH, ethyl or methoxy.

Additionally preferred compounds are the ones having formula II or III

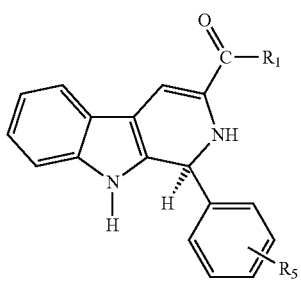

Formula II

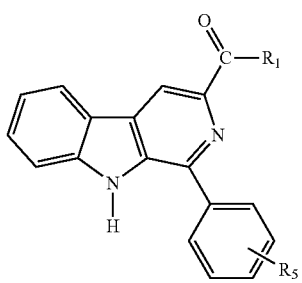

Formula III wherein, independently, $R_1$ can selected from: OH, p-OCH$_3$, NH—(CH$_2$)$_n$—NH$_2$ being n a value between 0 and 3;

or NH—N=CH-phenyl-R$_7$;

$R_5$ can be selected from: OCH$_3$ or H;

$R_7$ can be selected from: H or p-NO$_2$

More particularly, preferred compounds are those wherein, when $R_1$ is a group OH, $R_5$ is selected from H or p-OCH$_3$.

Still preferred compounds are those having a formula II selected from formula 1a wherein $R_1$ is a group OH and $R_5$ is p-OCH$_3$; or from formula 1b, wherein $R_1$ is a group OH and $R_5$ is H.

Also, preferred compounds are those wherein, when $R_1$ is a group OCH$_3$, $R_5$ is selected from H or p-OCH$_3$.

Preferred compounds according to present invention are those having a formula II selected from: formula 2a, wherein $R_1$ is a group OCH$_3$ and $R_5$ is p-OCH$_3$; from formula 2b, wherein $R_1$ is a group OCH$_3$ and $R_5$ is H; or having a formula III selected from formula 3a, wherein $R_1$ is a group OCH$_3$ and $R_5$ is p-OCH$_3$ or from formula 3b, wherein $R_1$ is a group OCH$_3$ and $R_5$ is H.

Also, preferred compounds are those wherein, when $R_1$ is a group NH—(CH$_2$)$_n$—NH$_2$, being the value of n=2 or 3, $R_5$ is p-OCH$_3$.

Preferred compounds according to present invention are those having a formula III selected from formula 4a, wherein $R_1$ is NH(CH$_2$)$_2$NH$_2$ and $R_5$ is p-OCH$_3$; or from formula 5a, wherein $R_1$ is NH(CH$_2$)$_3$NH$_2$ and $R_5$ is p-OCH$_3$.

More preferred compounds according to the present invention are the ones having formula III, wherein, when $R_1$ is a group NH—(CH$_2$)$_n$—NH$_2$, being the value of n=0, $R_5$ is selected from H or p-OCH$_3$.

Compounds also comprises in the present invention are those having a formula III selected from formula 6a, wherein $R_1$ is NHNH$_2$ and $R_5$ is p-OCH$_3$; or from formula 6b, wherein $R_1$ is NHNH$_2$ and $R_5$ is H.

More particularly, preferred compounds are those wherein, in formula III, when being $R_1$ a group NH—N=CH-phenyl, $R_5$ is p-OCH$_3$ and when being $R_1$ a group NH—N=CH— phenyl substituted by a group p-NO$_2$, $R_5$ is H.

Compounds also included in the scope of the present invention are the ones having a formula III selected from formula 7a, wherein $R_1$ is a group NH—N=CH-phenyl and $R_5$ is p-OCH$_3$; or from formula 7b, wherein $R_1$ is a group NH—N=CH-phenyl-p-NO$_2$ and $R_5$ is H.

Still most preferred compounds according to the present invention are selected among compounds: 4a, 5a, 7a, 17a, 17b, 17c, 21a, 21b, 21c, 21d, 21e, 21f, 23a, 23b, 23c, 23d, 23e, 23f, 26a or 26b, as shown in Table 1.

TABLE 1

| Compound | Structure | Name |
|---|---|---|
| IFC-110248S (ANIS-NH2 or 4a) | 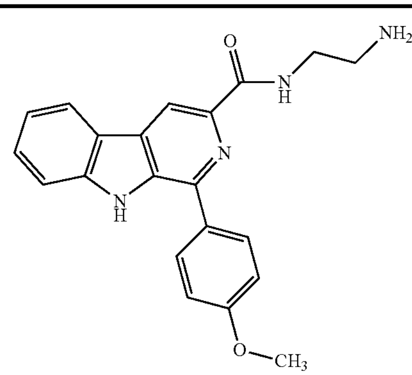 | N(-ethylamine)-1-benzosubstituted-β-carboline-3-carboxamide |

TABLE 1-continued

| Compound | Structure | Name |
|---|---|---|
| IFC-1102-57S (5a) | 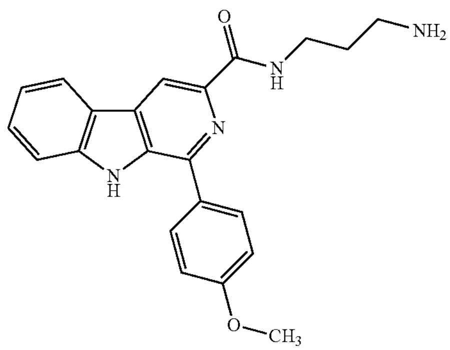 [SMILES: COc1ccc(-c2nc(C(=O)NCCCN)cc3c2[nH]c2ccccc23)cc1] | N(-propylamine)-1-benzosubstituted-β-carboline-3-carboxamide |
| IFC-1201-04 (ANIS-BZ or 7a) | 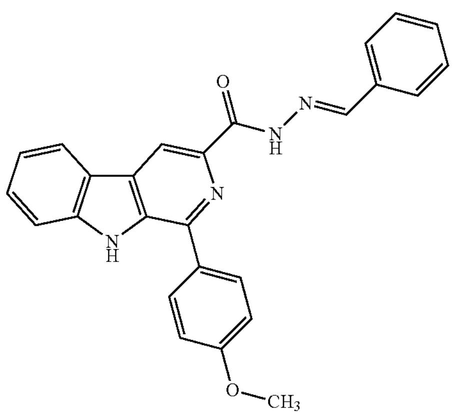 [SMILES: COc1ccc(-c2nc(C(=O)N/N=C/c3ccccc3)cc3c2[nH]c2ccccc23)cc1] | 3-(carbohydrazyl-N'-phenylsubstitute)-1-benzosubstitute-β-carbolinic-3-carbohydrazide |
| JHG-1117-26 (23b) | 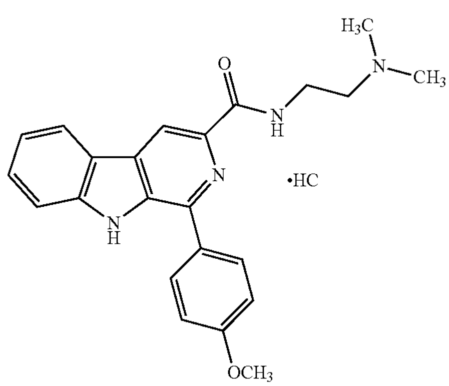 | N-(2-dimethylaminoethyl)-1-(4-methoxyphenyl)-9H-pyrido[3,4-b]indole-3-carboxamide hydrochloride |
| JHG-1117-28 (23c) | 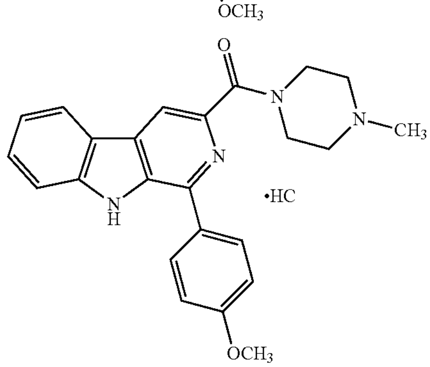 | [1-(4-methoxyphenyl)-9H-pyrido[3,4-b]indol-3-yl]-(4-methylpiperazin-1-yl)methanone hydrochloride |

TABLE 1-continued

| Compound | Structure | Name |
|---|---|---|
| JHG-1117-29 (26a) | 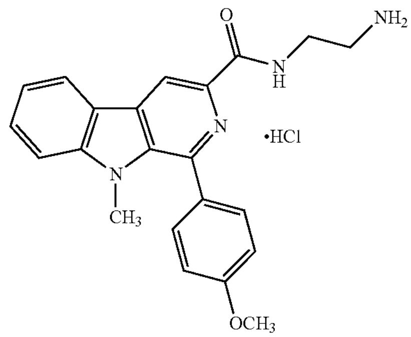 [SMILES: COc1ccc(-c2nc(C(=O)NCCN)cc3c4ccccc4n(C)c23)cc1 ; Cl] | N-(2-aminoethyl)-1-(4-methoxyphenyl)-9-methyl-pyrido[3,4-b]indole-3-carboxamide hydrochloride |
| IFC-1102-79 (21a) | 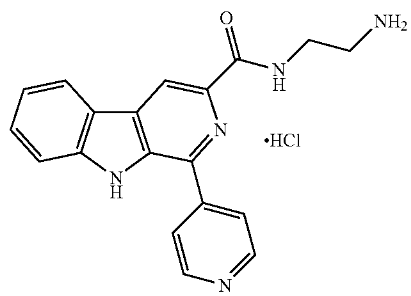 [SMILES: NCCNC(=O)c1cc2c([nH]c3ccccc32)c(-c2ccncc2)n1 ; Cl] | N-(2-aminoethyl)-1-(4-pyridyl)-9H-pyrido[3,4-b]indole-3-carboxamide hydrochloride |
| JHG-1117-24 (23a) | 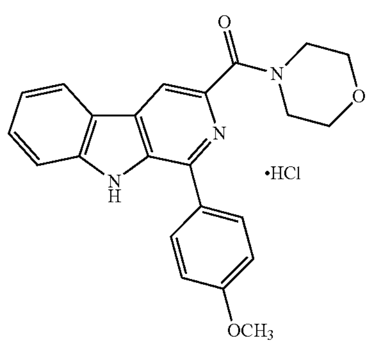 [SMILES: COc1ccc(-c2nc(C(=O)N3CCOCC3)cc3c2[nH]c2ccccc23)cc1 ; Cl] | [1-(4-methoxyphenyl)-9H-pyrido[3,4-b]indol-3-yl]-4-morpholinyl-Methanone Hydrochloride |
| JHG-1117-27S2 (23e) | 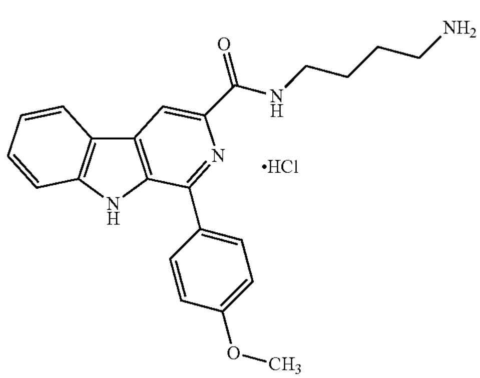 [SMILES: COc1ccc(-c2nc(C(=O)NCCCCN)cc3c2[nH]c2ccccc23)cc1 ; Cl] | N-(4-aminobutyl)-1-(4-methoxyphenyl)-9H-pyrido[3,4-b]indole-3-carboxamide hydrochloride |

TABLE 1-continued

| Compound | Structure | Name |
|---|---|---|
| JHG-1117-41 (23d) | 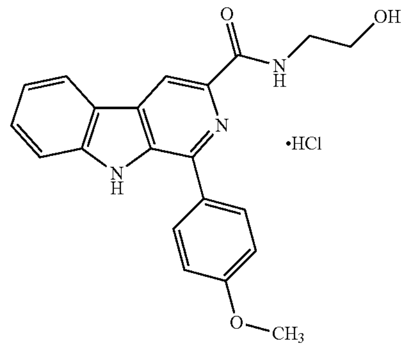 [SMILES: COc1ccc(-c2nc(C(=O)NCCO)cc3c2[nH]c2ccccc23)cc1 ; Cl] | N-(2-hydroxyethyl)-1-(4-methoxyphenyl)-9H-pyrido[3,4-b]indole-3-carboxamide hydrochloride |
| JHG-1117-43 (26b) | 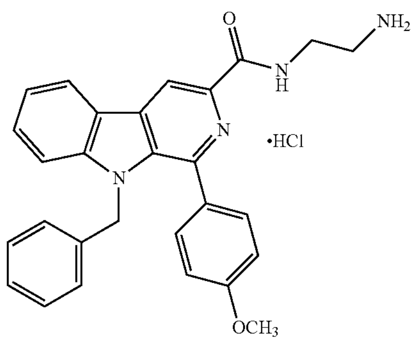 [SMILES: COc1ccc(-c2nc(C(=O)NCCN)cc3c4ccccc4n(Cc4ccccc4)c23)cc1 ; Cl] | N-(2-aminoethyl)-9-benzyl-1-(4-methoxyphenyl)pyrido[3,4-b]indole-3-carboxamide hydrochloride |
| IFC-1102-92 (21b) | 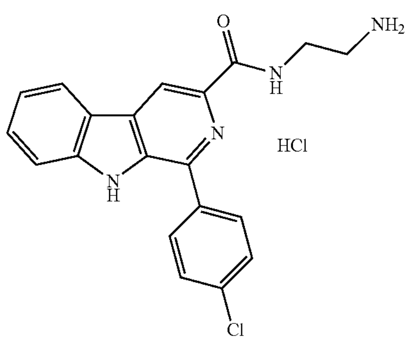 [SMILES: NCCNC(=O)c1cc2c([nH]c3ccccc32)c(-c2ccc(Cl)cc2)n1 ; Cl] | N-(2-aminoethyl)-1-(4-chlorophenyl)-9H-pyrido[3,4-b]indole-3-carboxamide |
| IFC-1102-93 (21c) | 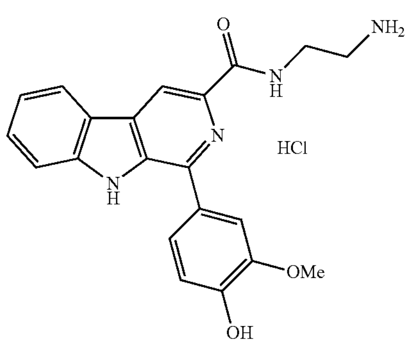 [SMILES: COc1cc(-c2nc(C(=O)NCCN)cc3c2[nH]c2ccccc23)ccc1O ; Cl] | N-(2-aminoethyl)-1-(4-hydroxy-3-methoxy-phenyl)-9H-pyrido[3,4-b]indole-3-carboxamide hydrochloride |

TABLE 1-continued

| Compound | Structure | Name |
|---|---|---|
| IFC-1102-96 (21e) | 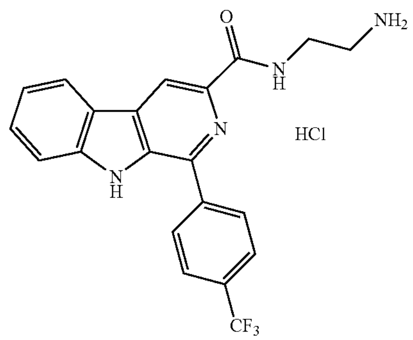 [SMILES: NCCNC(=O)c1cc2c([nH]c3ccccc32)c(-c2ccc(C(F)(F)F)cc2)n1 ; Cl] | N-(2-aminoethyl)-1-[4-(trifluoromethyl)phenyl]-9H-pyrido[3,4-b]indole-3-carboxamide hydrochloride |
| IFC-1102-94 (21d) | 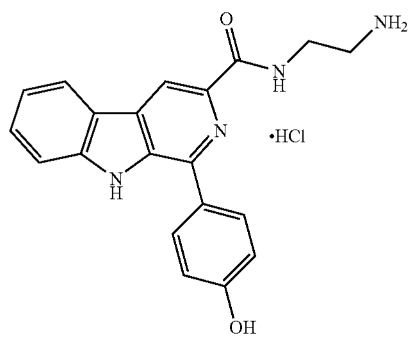 [SMILES: NCCNC(=O)c1cc2c([nH]c3ccccc32)c(-c2ccc(O)cc2)n1 ; Cl] | N-(2-aminoethyl)-1-(4-hydroxyphenyl)-9H-pyrido[3,4-b]indole-3-carboxamide hydrochloride |
| IFC-1201-04 (21f) | 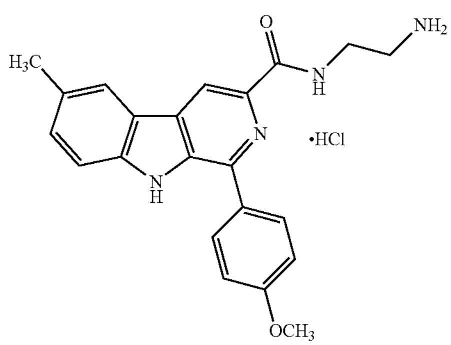 [SMILES: COc1ccc(-c2nc(C(=O)NCCN)cc3c2[nH]c2ccc(C)cc23)cc1 ; Cl] | N-(2-aminoethyl)-6-methyl-1-(4-ethoxyphenyl)-9H-pyrido[3,4-b]indole-3-carboxamide hydrochloride |
| IFC-1201-07 (17c) | 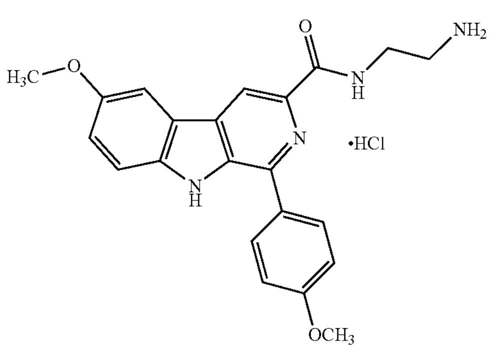 [SMILES: COc1ccc(-c2nc(C(=O)NCCN)cc3c2[nH]c2ccc(OC)cc23)cc1 ; Cl] | N-(2-aminoethyl)-6-methoxy-1-(4-methoxyphenyl)-9H-pyrido[3,4-b]indole-3-carboxamide hydrochloride |

TABLE 1-continued

| Compound | Structure | Name |
|---|---|---|
| IFC-1201-05 (17b) | 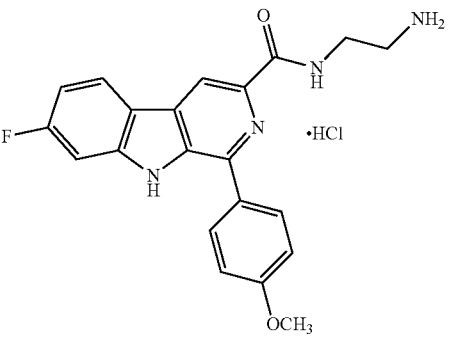 [SMILES: COc1ccc(-c2nc(C(=O)NCCN)cc3c2[nH]c2cc(F)ccc23)cc1 ; Cl] | N-(2-aminoethyl)-7-fluoro-1-(4-methoxyphenyl)-9H-pyrido[3,4-b]indole-3-carboxamide hydrochloride |
| IFC-1201-06 (20f) | 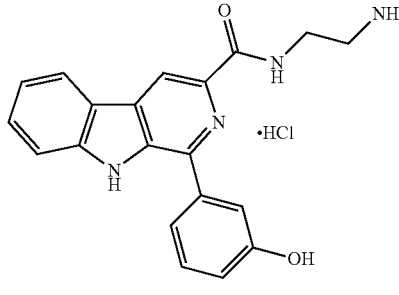 | N-(2-aminoethyl)-1-(3-hydroxyphenyl)-9H-pyrido[3,4-b]indole-3-carboxamide hydrochloride |
| IFC-1201-09 (23f) | 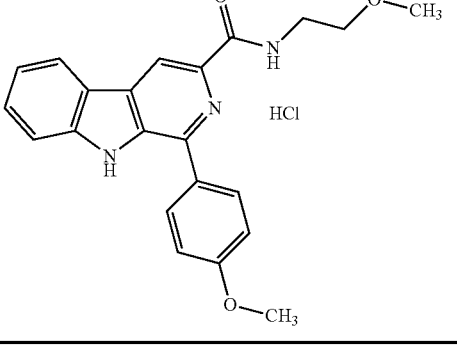 | N-(2-methoxyethyl)-1-phenyl-9H-pyrido[3,4-b]indole-3-carboxamide hydrochloride |

Present invention also covers all intermediate compounds in the synthesis of compounds of previously described compounds. Particularly, the invention covers intermediate compounds selected from: 1a, 1b, 2a, 2b, 3a, 3b, 6a, 6b, 7b, 8, 9, 13, 14a, 14b, 14c, 15a, 15b, 15c, 16a, 16b, 16c, 18a, 18b, 18c, 18d, 18e, 18f, 19a, 19b, 19c, 19d, 19e, 19f, 20a, 20b, 20c, 20d, 20e, 20f, 22a, 22b, 22c, 22d, 22e, 22f, 24a, 24b, 25a, or 25b.

The invention includes pharmaceutical, cosmetic, functional food additive or nutraceutical compositions comprising at least any of the previously mentioned compounds represented by general formulas I, II and III, and their pharmaceutically, cosmetically or food grade, acceptable or allowable, salts and combinations thereof, optionally with any inert ingredient, carrier, excipient or alike.

The invention also comprises any of the compounds covered by general formula I, II or III as previously disclosed or any pharmaceutical composition comprising the same, for use as medicament, or for use for manufacturing a medicament.

The invention also comprises any of the compounds covered by general formula I, II or III, as previously disclosed, or pharmaceutical compositions comprising the same, for use in the treatment or prevention of metabolic syndrome, metabolic disease or metabolic disorders, or for use in manufacturing a medicament for the treatment or prevention of metabolic syndrome, metabolic disease or metabolic disorders.

Preferably, the invention also comprises compounds named as: 4a, 5a, 7a, 21a, 21b, 21e, 23a, 23b, 23d, 23e, 23f or 26b, taken alone or in combinations thereof, or pharmaceutical compositions comprising the same, are particularly suitable for use in the treatment or prevention of metabolic syndrome, or for use in manufacturing a medicament for the treatment or prevention of metabolic syndrome.

The invention also comprises any of the compounds covered by general formula I, II or III, as previously disclosed, or pharmaceutical compositions comprising the same, for use in the treatment or prevention of diabetes, or for use in manufacturing a medicament for the treatment or prevention of diabetes.

Preferably, the invention also comprises compounds named as: 4a, 5a, 7a, 21a, 21b, 21e, 23a, 23b, 23d, 23e, 23f or 26b, taken alone or in combinations thereof, or pharmaceutical compositions comprising the same, are particularly suitable for use in the treatment or prevention of diabetes, or for use in manufacturing a medicament for the treatment or prevention of diabetes.

The invention also comprises any of the compounds covered by general formula I, II or III, as previously disclosed, for any pharmaceutical composition comprising the same, for use in the treatment or prevention of hypertension, or for use in manufacturing a medicament for the treatment or prevention of hypertension.

Preferably, the invention also comprises compounds named as: 4a, 5a, 7a, 21a, 21b, 21e, 23a, 23b, 23d, 23e, 23f or 26b, taken alone or in combinations thereof, or any pharmaceutical composition comprising the same, are particularly suitable for use in the treatment or prevention of hypertension, or for use in manufacturing a medicament for the treatment or prevention of hypertension. More preferably, compounds 4a, 5a and 7a or any pharmaceutical composition comprising the same, are selected for use in the treatment or prevention of hypertension, or for use in manufacturing a medicament for the treatment or prevention of hypertension.

The invention also comprises any of the compounds covered by general formula I, II or III, as previously disclosed, or any pharmaceutical composition comprising the same, for use in the treatment or prevention of hyperlipidemia, assessed mainly as hypercholesterolemia, or for use in manufacturing a medicament for the treatment or prevention of hyperlipidemia, in general, and particularly for treatment or prevention of hypercholesterolemia.

Preferably, the invention also comprises compounds named as: 4a, 5a, 7a, 21a, 21b, 21e, 23a, 23b, 23d, 23e, 23f or 26b, taken alone or in combinations thereof, or any pharmaceutical composition comprising the same, for use in the treatment or prevention of hyperlipidemia, assessed mainly as hypercholesterolemia, or for use in manufacturing a medicament for the treatment or prevention of hyperlipidemia, in general, and particularly for treatment or prevention of hypercholesterolemia. More preferably, compounds 4a, 5a and 7a or any pharmaceutical composition comprising the same, are selected for use in the treatment or prevention of hyperlipidemia, assessed mainly as hypercholesterolemia, or for use in manufacturing a medicament for the treatment or prevention of hyperlipidemia, in general, and particularly for treatment or prevention of hypercholesterolemia.

The invention also comprises any of the compounds covered by general formula I, II or III, as previously disclosed, or any pharmaceutical composition comprising the same, for use in the treatment or prevention of hyperlipidemia, assessed mainly as hypertriglyceridemia, or for use in manufacturing a medicament for the treatment or prevention of hyperlipidemia, in general, and particularly for treatment or prevention of hypertriglyceridemia.

Preferably, the invention also comprises compounds named as: 4a, 5a, 7a, 21a, 21b, 21e, 23a, 23b, 23d, 23e, 23f or 26b, taken alone or in combinations thereof, or any pharmaceutical composition comprising the same, are particularly suitable for use in the treatment or prevention of hyperlipidemia, assessed mainly as hypertriglyceridemia, or for use in manufacturing a medicament for the treatment or prevention of hyperlipidemia, in general, and particularly for treatment or prevention of hypertriglyceridemia. More preferably, compound 4a is selected for use in the treatment or prevention of hyperlipidemia, assessed mainly as hypertriglyceridemia, or for use in manufacturing a medicament for the treatment or prevention of hyperlipidemia, in general, and particularly for treatment or prevention of hypertriglyceridemia.

The invention also comprises any of the compounds covered by general formula I, II or III as previously disclosed, or any pharmaceutical composition comprising the same, for use in the treatment or prevention of obesity or overweight, or for use in manufacturing a medicament for the treatment or prevention of obesity or overweight.

Preferably, the invention also comprises compounds named as: 4a, 5a, 7a, 21a, 21b, 21e, 23a, 23b, 23d, 23e, 23f or 26b, taken alone or in combinations thereof, or any pharmaceutical composition comprising the same, they all are particularly suitable for use in the treatment or prevention of obesity or overweight, or for use in manufacturing a medicament for the treatment or prevention of obesity or overweight. More preferably, compound 5a or any pharmaceutical composition comprising the same, it is selected for use in the treatment or prevention of obesity or overweight, or for use in manufacturing a medicament for the treatment or prevention of obesity or overweight.

The invention also comprises any of the compounds covered by general formula I, II or III as previously disclosed, or any cosmetic composition comprising the same, for use as cosmetic particularly for reducing obesity or overweight, or for use in manufacturing a cosmetic particularly for reducing obesity or overweight.

Preferably, the invention also comprises compounds named as: 4a, 5a, 7a, 21a, 21b, 21e, 23a, 23b, 23d, 23e, 23f or 26b, taken alone or in combinations thereof, or any cosmetic composition comprising the same, they are particularly suitable for use as cosmetic particularly for reducing obesity or overweight, or for use in manufacturing a cosmetic particularly for reducing obesity or overweight. More preferably, compound 5a or any cosmetic composition comprising the same, it is selected for use as cosmetic particularly for reducing obesity or overweight, or for use in manufacturing a cosmetic particularly for reducing obesity or overweight.

The invention also comprises any of the compounds covered by general formula I, II or III as previously disclosed, or any functional food additive or nutraceutical composition comprising the same, for use as food functional additive or nutraceutic particularly for preventing or for reducing the symptoms related to: diabetes, elevated glucose blood levels, hypertension, elevated blood cholesterol levels, elevated blood triglycerides levels, obesity or overweight, or for use in manufacturing a food functional additive or nutraceutic particularly for preventing or for reducing the symptoms related to: diabetes, elevated glucose blood levels, hypertension, elevated blood cholesterol levels, elevated blood triglycerides levels, obesity or overweight.

Preferably, the invention also comprises compounds named as: 4a, 5a, 7a, 21a, 21b, 21e, 23a, 23b, 23d, 23e, 23f or 26b, taken alone or in combinations thereof, or any functional food additive or nutraceutical composition comprising the same, they are particularly suitable for use as food functional additive or nutraceutic particularly for preventing or for reducing the symptoms related to: diabetes, elevated glucose blood levels, hypertension, elevated blood cholesterol levels, elevated blood triglycerides levels, obesity or overweight, or for use in manufacturing a food functional additive or nutraceutic particularly for preventing or for reducing the symptoms related to: diabetes, elevated glucose blood levels, hypertension, elevated blood cholesterol levels, elevated blood triglycerides levels, obesity or overweight.

The invention also discloses processes for producing the different compounds represented by formula I, II or III.

Particularly, it has been disclosed, a process of synthesis of a compound of formula I and any pharmaceutically, cosmetically or foodstuff acceptable salt thereof:

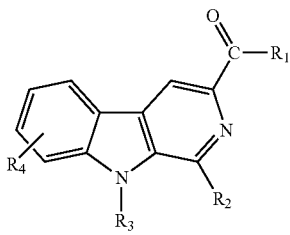

wherein, independently, $R_1$ can selected from: linear or cycled mono or dialkylamines; aminoalkylalcohols or aminoalkylethers;

$R_2$ can be selected from: benzene or heterocycle rings;

$R_3$ can be selected from: H; a hydrocarbon radical selected from straight or branched alkyl of from 1 to 5 carbons; or benzyl group;

$R_4$ can be selected from: H; a hydrocarbon radical selected from straight or branched alkyl of from 1 to 5 carbons; hydroxy or alkoxy radicals; or halogen, which comprises:

i. condensation reaction of L-tryptophan and an aldehyde selected from anisaldehyde (a) or benzaldehyde (b), obtaining compounds 1a or 1 b, respectively;

ii. diluting compounds 1a or 1b, respectively, in an alcohol, and adding to the corresponding solutions an acid; after evaporation of the alcohol the resulting products were neutralized with a base; then the organic phase was extracted with an organic solvent and after drying and solvent removal, compounds 2a or 2b were obtained;

iii. compounds 2a or 2b were dissolved in an organic solvent and an acid was added until a precipitate was obtained; the precipitate was filtered and washed with an ether, thus obtaining compounds 3a or 3b, respectively iv. compound 3a is reacted either with ethylenediamine or propylenediamine, obtaining, respectively, compounds 4a or 5a;

alternatively, compounds 3a or 3b are reacted, in an alcohol solution, with a hydrazine until a precipitate is formed; the precipitate is filtered and washed with an alcohol and compounds 6a and 6b are respectively;

v. to a solution of compounds 6a or 6b in water, an acid is added and, after solubilization, each respective aldehyde in alcohol solution, benzaldehyde for compound 6a and p-nitrobenzaldehyde for compound 6b, is added; after base neutralization a precipitate is formed which is filtered and recrystallized with an alcohol, hence obtaining, respectively compounds 7a and 7b.

An embodiment of the previous process is that wherein step iv) is replaced, alternatively, as follows:

iv' compound 3a is dissolved in 1,3-diaminepropane and the excess of diamine was removed; the solid formed was triturated with acetone and then filtered for obtaining compound 5a;

Another embodiment of the process disclosed hereto is that wherein step v) is replaced, alternatively, as follows:

v' an alcohol suspension of compound 6a is heated and then benzaldehyde is added also in alcohol solution until complete solubilization; the crude was concentrated until obtaining a solid which is recrystallized with an alcohol, obtaining compound 7a.

As additional process step for the above previous preferred embodiments for the compounds' production processes is that wherein any compound obtained selected among: 2a, 2b, 3a, 3b, 4a, 5a, 6a, 6b, 7a or 7b, is further reacted with an acid in order to form the corresponding salt, preferably, wherein the acid is HCl and the salt formed is the corresponding clorhidrate.

The inventions also disclose the different processes for preparation of each one of the claimed compounds.

Compound Synthesis:

A.-Scheme I of β-carbolinic derivatives synthesis:

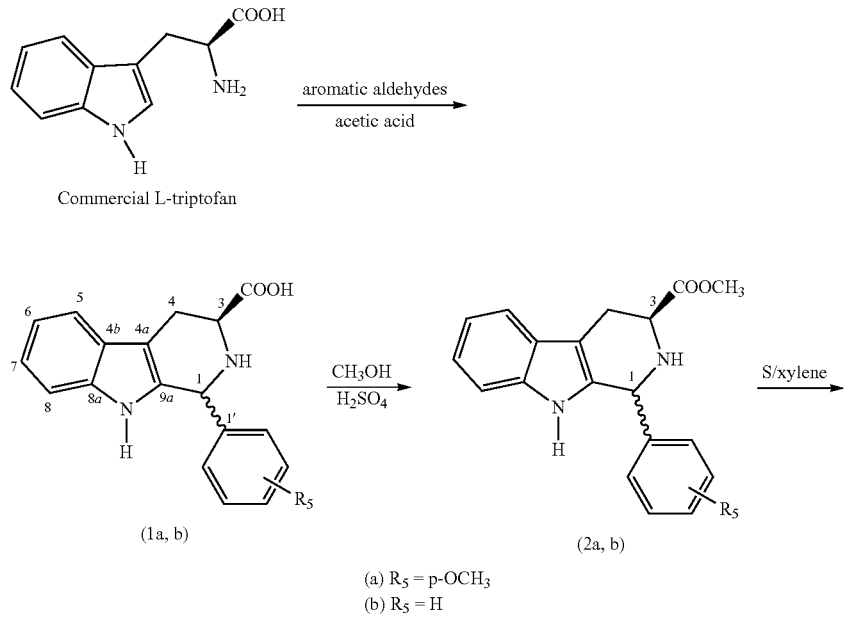

-continued

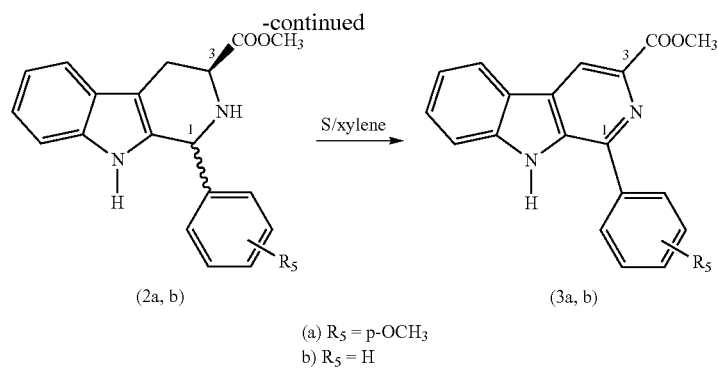

(a) $R_5$ = p-OCH$_3$
b) $R_5$ = H

S: sulfur; S/xylene

For the purposes of the present invention, wavy bond indicates that the corresponding substituents can be in axial or equatorial.

B.-Scheme II of carboxiamide derivatives synthesis:

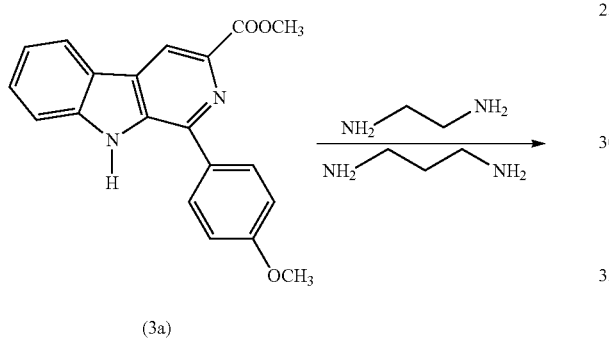

C.-Scheme III of carbohydrazide derivatives synthesis:

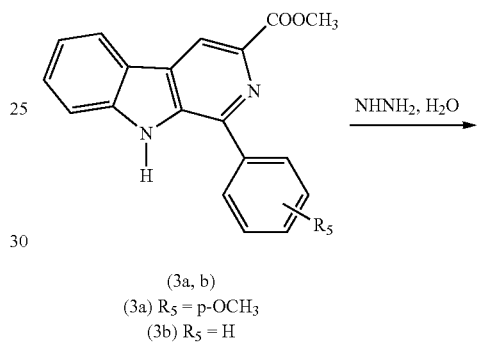

(3a, b)
(3a) $R_5$ = p-OCH$_3$
(3b) $R_5$ = H

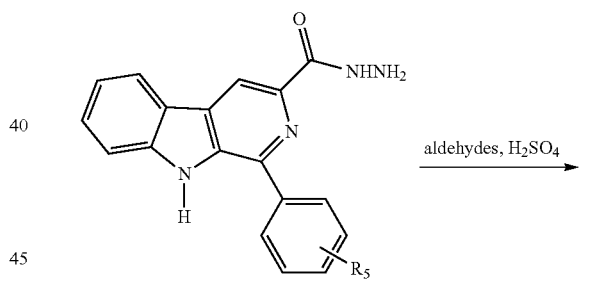

(6a, b)
(6a) $R_5$ = p-OCH$_3$
(6b) $R_5$ = H n = 2 (4a)
n = 3 (5a)

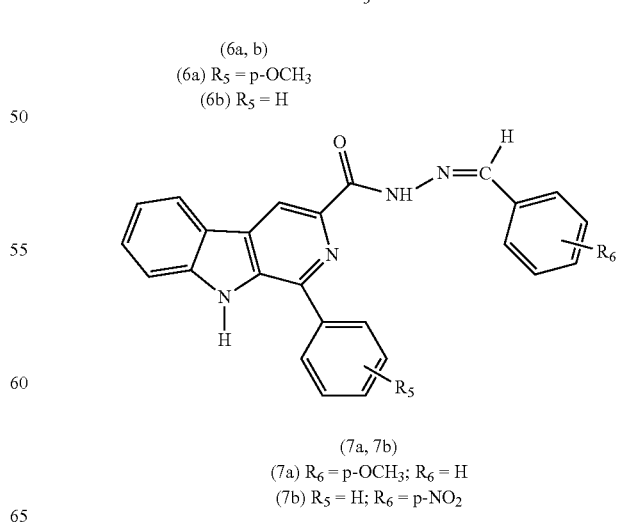

(7a, 7b)
(7a) $R_6$ = p-OCH$_3$; $R_6$ = H
(7b) $R_5$ = H; $R_6$ = p-NO$_2$

D.- Scheme IV of alternative synthesis of compounds 4a, 5a and 7a:
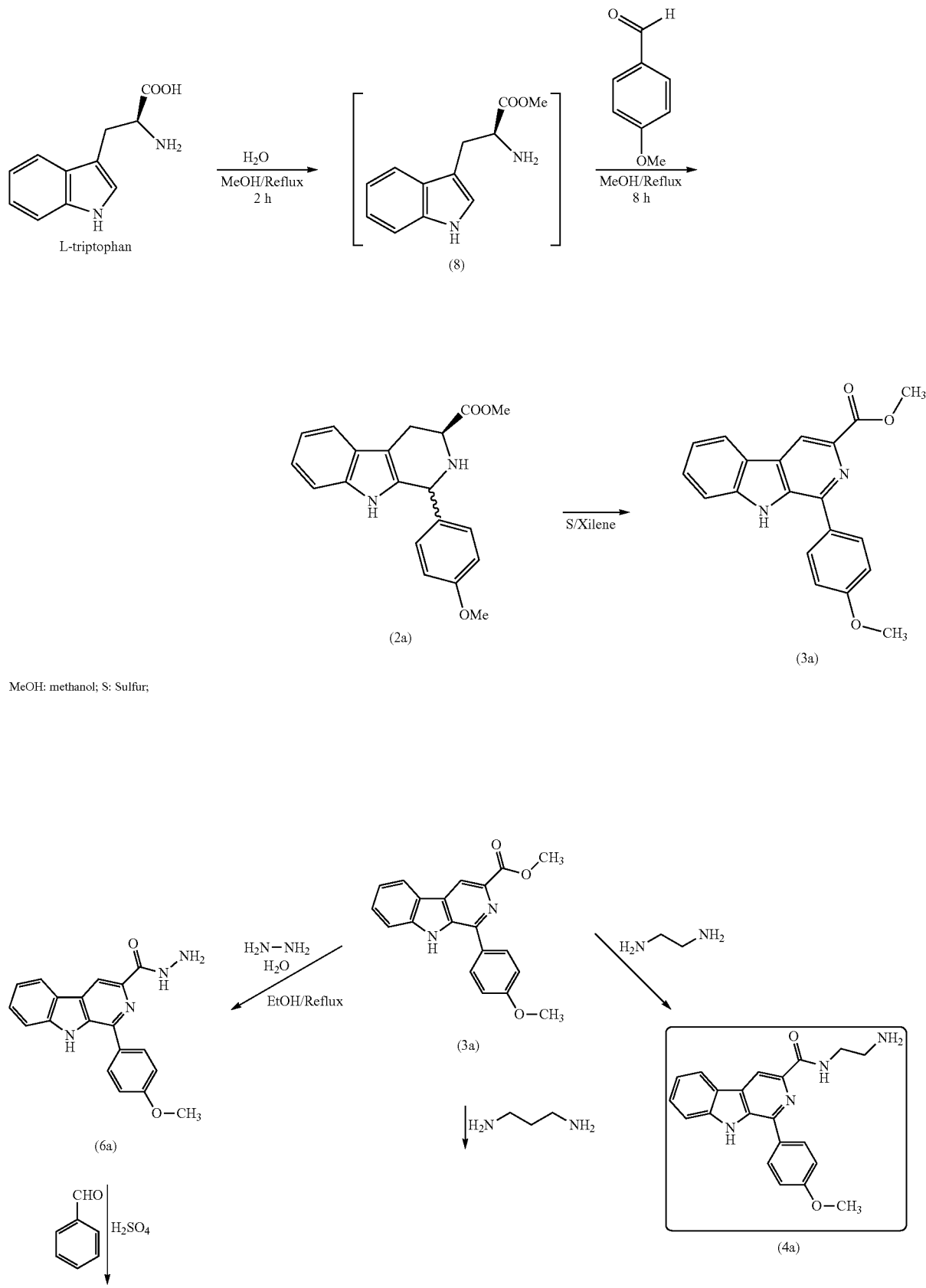
MeOH: methanol; S: Sulfur;

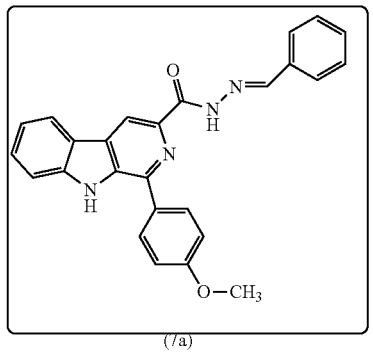
(7a)
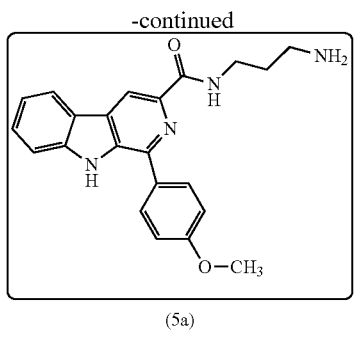
(5a)
E.- Scheme V of synthesis of derivatives of general formula I. The different domains modified for synthesis of said derivatives are shown in the following Scheme V:
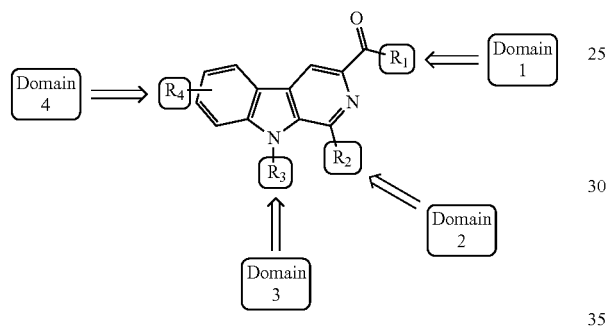
E1: Variation in the Domain 1 ($R_1$)
The variations in the Domain 1 are achieved by reaction with different amines in the last step. The synthesis is represented in the Scheme VI:
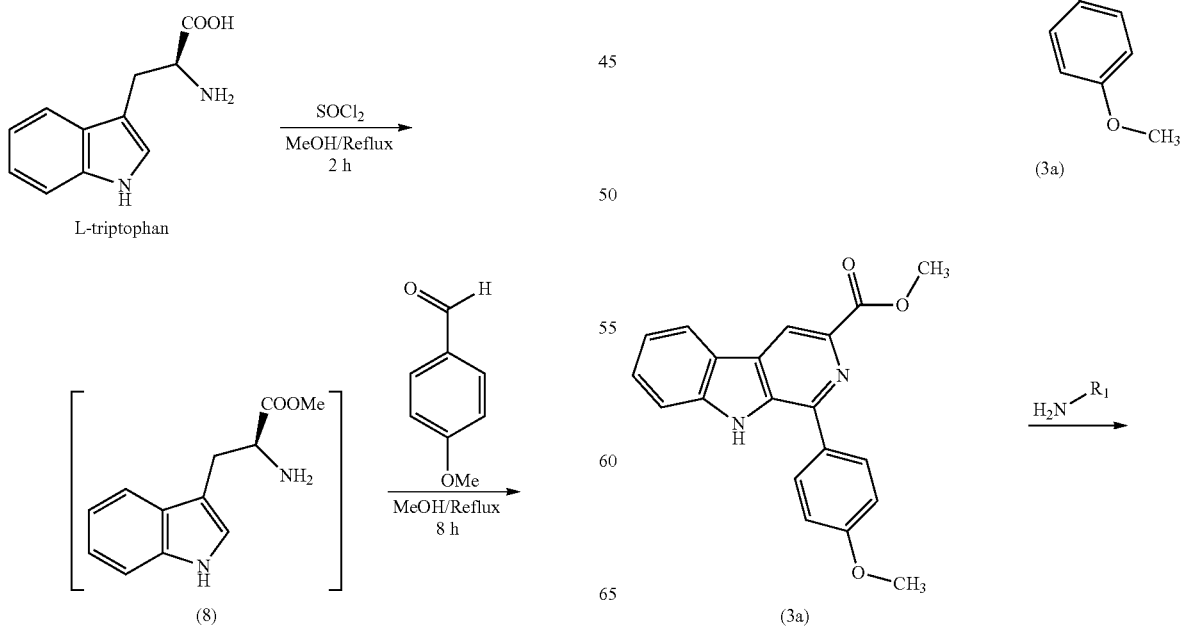

25
-continued

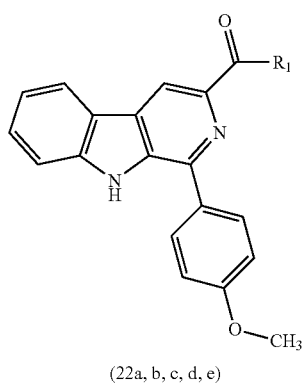

(22a, b, c, d, e)

→ HCl

26
-continued

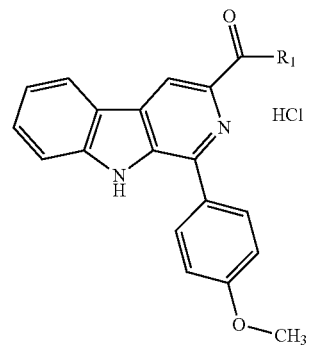

(23a, b, c, d, e)

TABLE 2

| Variations in Domain 1 ($R_1$) | | | | |
|---|---|---|---|---|
| Compound | $R_1$ | $R_2$ | $R_3$ | $R_4$ |
| 23a (JHG-1117-24) | 4-Morpholinyl | 1-(4-methoxyphenyl) | H | H |
| 23b (JHG-1117-26) | $HNCH_2CH_2N(CH_3)_2$ N-(2-dimethylaminoethyl) | 1-(4-methoxyphenyl) | H | H |
| 23c (JHG-1117-28) | 4-methylpiperazin-1-yl | 1-(4-methoxyphenyl) | H | H |
| 23d (JHG-1117-41) | $HNCH_2CH_2OH$ N-2-hydroxyethyl | 1-(4-methoxyphenyl) | H | H |
| 23e (JHG-1117-27S2) | $HN-(CH_2)_4-NH_2$ N-(4-aminobutyl) | 1-(4-methoxyphenyl) | H | H |
| 23f (IFC-1201-09) | $HNCH_2CH_2OCH_3$ N-(2-methoxyethyl) | 1-(4-methoxyphenyl) | H | H |

E2: Variation in the Domain 2 (R₂)

The reaction between L-tripthophan methyl ester and different aldehydes leads to compounds with different R₂. The synthesis is represented in the Scheme VII:

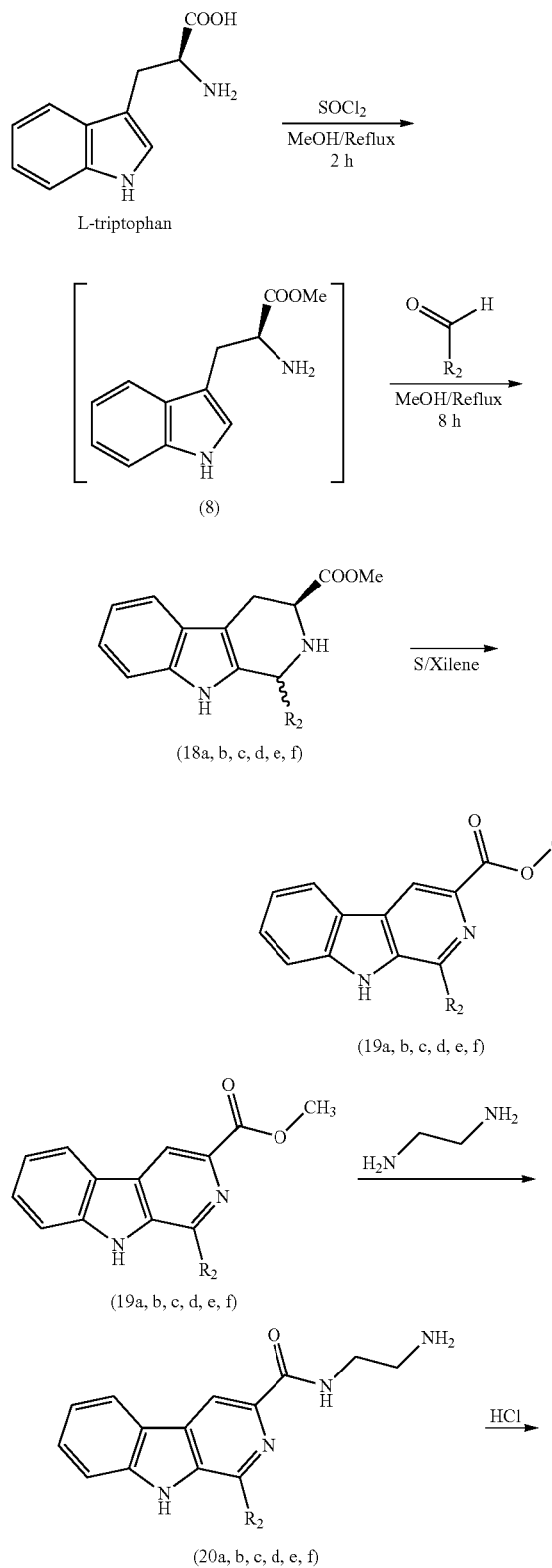

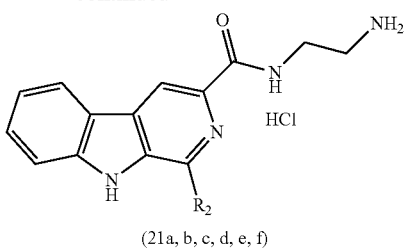

(21a, b, c, d, e, f)

TABLE 3

| | | Variations in Domain 2 (R₂) | | | |
|---|---|---|---|---|---|
| Compound | R₁ | | R₂ | R₃ | R₄ |
| 21a (IFC-1102-79) | HNCH₂CH₂NH₂ N-(2-aminoethyl) | | 1-(4-pyridyl) | H | H |
| 21b (IFC-1102-92) | HNCH₂CH₂NH₂ N-(2-aminoethyl) | | 1-(4-chlorophenyl) | H | H |
| 21c (IFC-1102-93) | HNCH₂CH₂NH₂ N-(2-aminoethyl) | | 1-(4-hydroxy-3-methoxyphenyl) | H | H |
| 21d (IFC-1102-94) | HNCH₂CH₂NH₂ N-(2-aminoethyl) | | 1-(4-hydroxyphenyl) | H | H |
| 21e (IFC-1102-96) | HNCH₂CH₂NH₂ N-(2-aminoethyl) | | 1-(4-(trifluoromethyl)phenyl) | H | H |
| 21f (IFC-1201-04) | HNCH₂CH₂NH₂ N-(2-aminoethyl) | | 1-(3-hydroxyphenyl) | H | H |

E3: Variation in the Domain 3 (R₃)

The variations in the Domain 3 are achieved following the synthetic method indicated in the Scheme VIII:

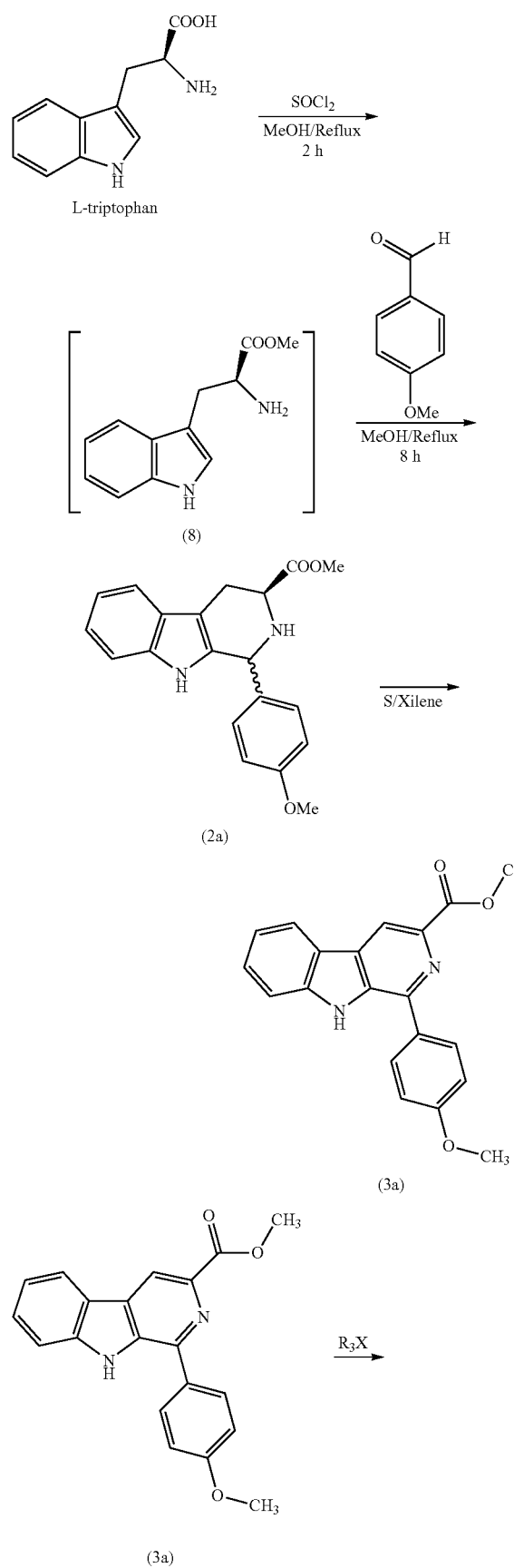
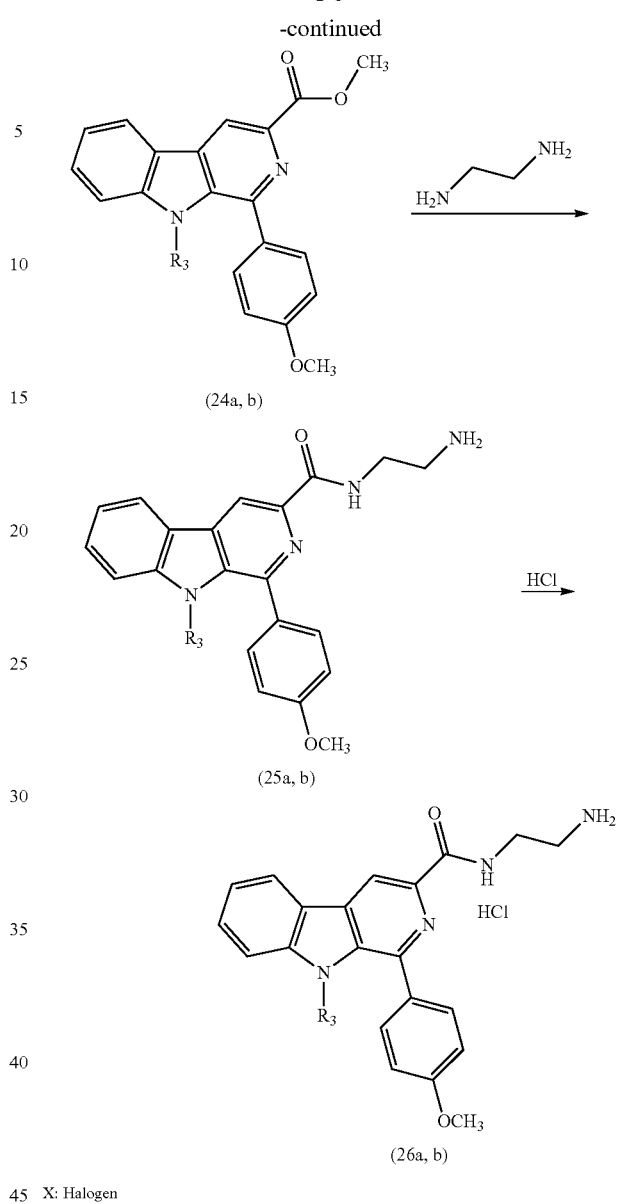
X: Halogen
TABLE 4
Variations in Domain 3 ($R_3$)
| Compound | $R_1$ | $R_2$ | $R_3$ | $R_4$ |
|---|---|---|---|---|
| 26a (JHG-1117-29) | HNCH$_2$CH$_2$NH$_2$ N-(2-aminoethyl) | 1-(4-methoxyphenyl) | CH$_3$ methyl | H |
| 26b (JHG-1117-43) | HNCH$_2$CH$_2$NH$_2$ N-(2-aminoethyl) | 1-(4-methoxyphenyl) | CH$_2$Ph benzyl | |
CH$_2$Ph: Benzyl group

E4. Variation in the Domain 4 ($R_4$)

To obtain compounds with different $R_4$ is necessary to use several triptophans as starting materials. The synthesis is represented in the Scheme IX:

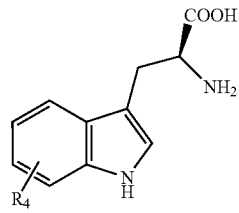

L-triptophan

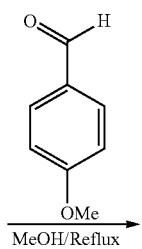

(13)

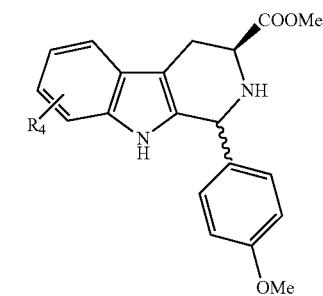

(14)

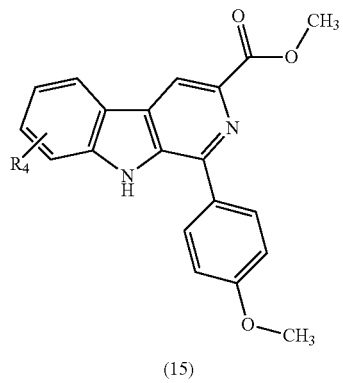

(15)

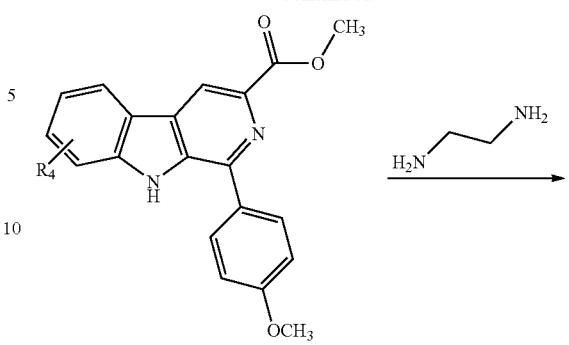

(15)

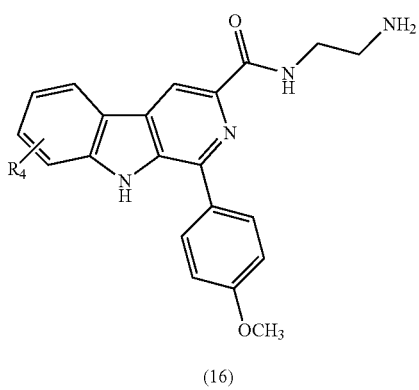

(16)

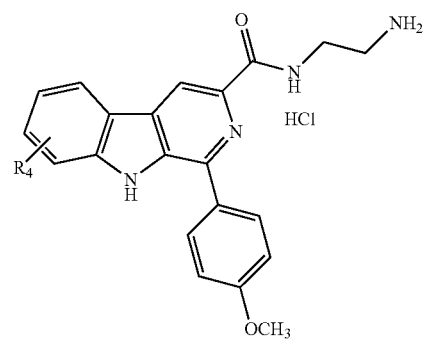

(17a, b, c)

TABLE 5

Variations in Domain 4 ($R_4$)

| Compound | $R_1$ | $R_2$ | $R_3$ | $R_4$ |
|---|---|---|---|---|
| 17a (IFC-1201-04) | HNCH$_2$CH$_2$NH$_2$ N-(2-aminoethyl) | 1-(4-methoxyphenyl) | H | CH$_3$ methyl |
| 17b (IFC-1201-05) | HNCH$_2$CH$_2$NH$_2$ N-(2-aminoethyl) | 1-(4-methoxyphenyl) | H | F fluoro |

TABLE 5-continued
Variations in Domain 4 (R4)
| Compound | R1 | R2 | R3 | R4 |
|---|---|---|---|---|
| 17c (IFC-1201-07) | HNCH₂CH₂NH₂ N-(2-aminoethyl) | 1-(4-methoxyphenyl) | H | OCH₃ methoxy |
F.- Scheme X of alternative synthesis of compound 4a (IFC-110248S):
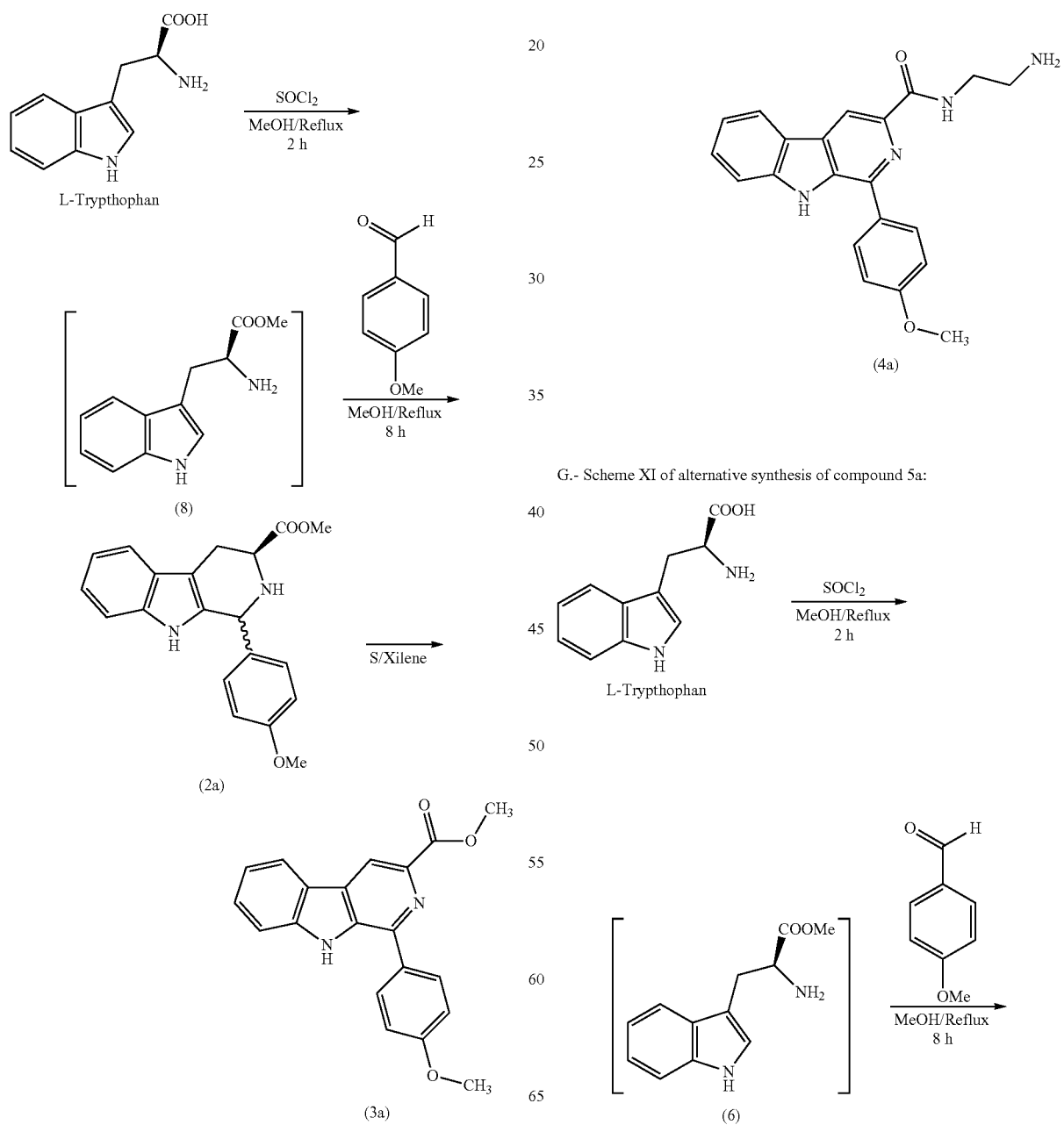
G.- Scheme XI of alternative synthesis of compound 5a:

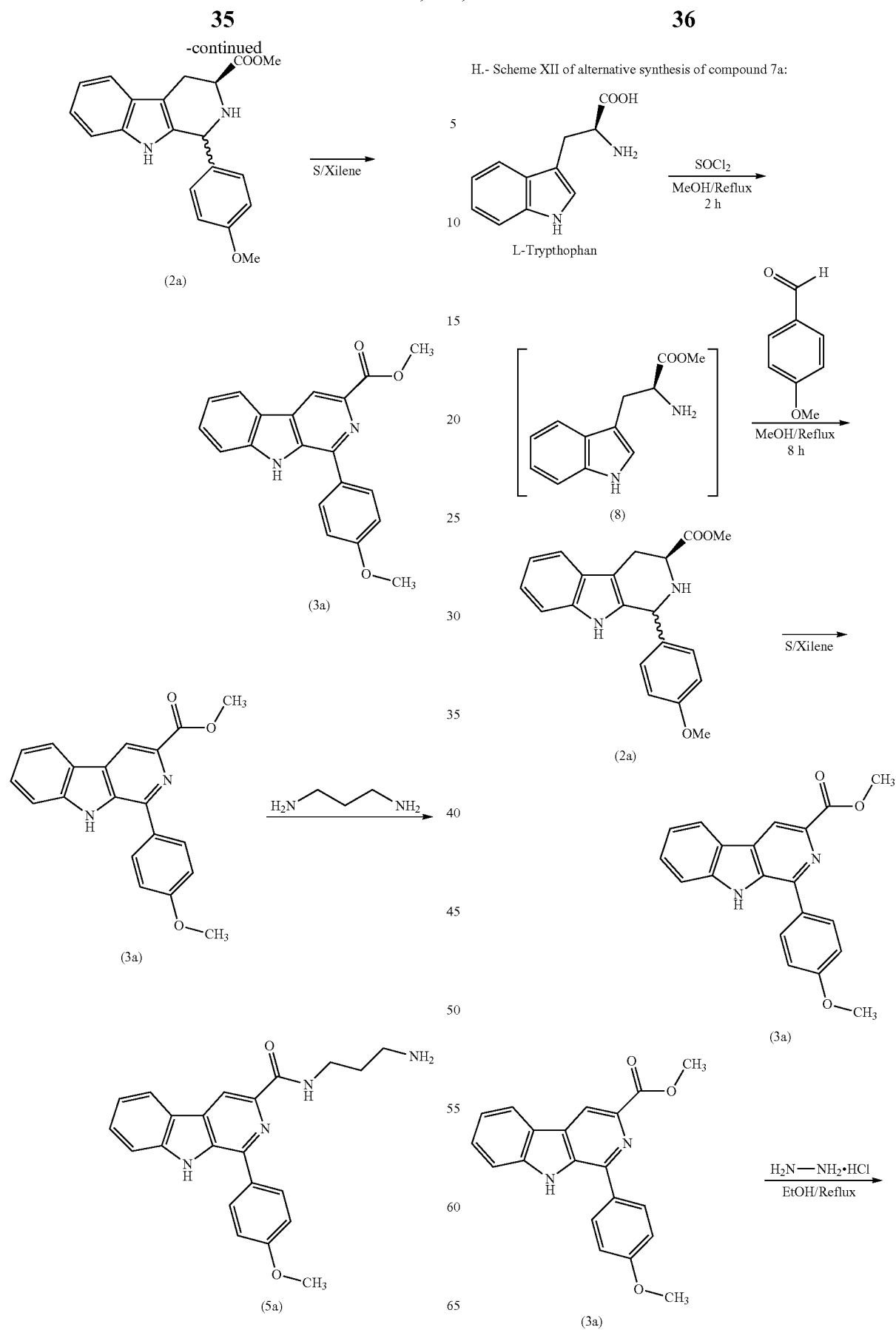

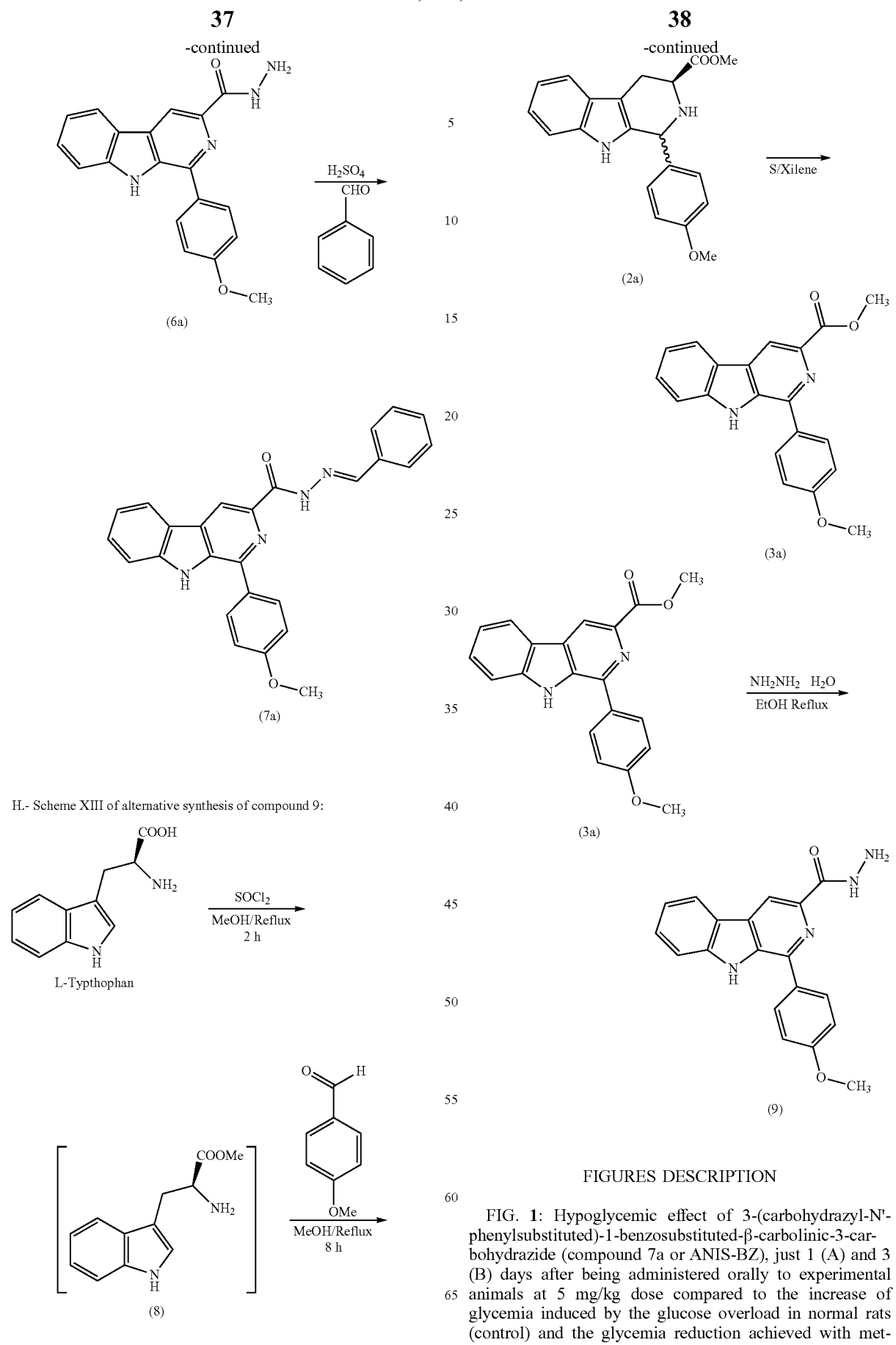

FIGURES DESCRIPTION

FIG. 1: Hypoglycemic effect of 3-(carbohydrazyl-N'-phenylsubstituted)-1-benzosubstituted-β-carbolinic-3-carbohydrazide (compound 7a or ANIS-BZ), just 1 (A) and 3 (B) days after being administered orally to experimental animals at 5 mg/kg dose compared to the increase of glycemia induced by the glucose overload in normal rats (control) and the glycemia reduction achieved with metformin (MET). Each bar represents the mean±SEM of 6 animals. *P<0.05, **P<0.01, compared with vehicle-treated control group.

Figure 2:
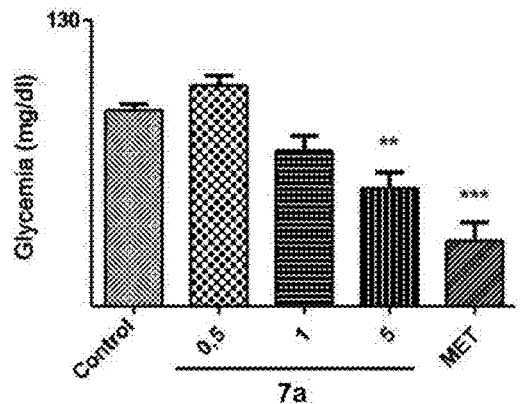

FIG. 2: Hypoglycemic effect after 3 days, of 3-(carbohydrazyl-N'-phenylsubstitute)-1-benzosubstitute-β-carbolinic-3-carbohydrazide (compound 7a or ANIS-BZ) at 0.5, 1 and 5 mg/kg doses compared to the increase of glycemia induced by glucose overload in normal rats and the glycemia reduction achieved with metformin (MET). Each bar represents the mean±SEM of 6 animals. P<0.01, *P<0.001, compared with vehicle-treated control group.

Figure 3:
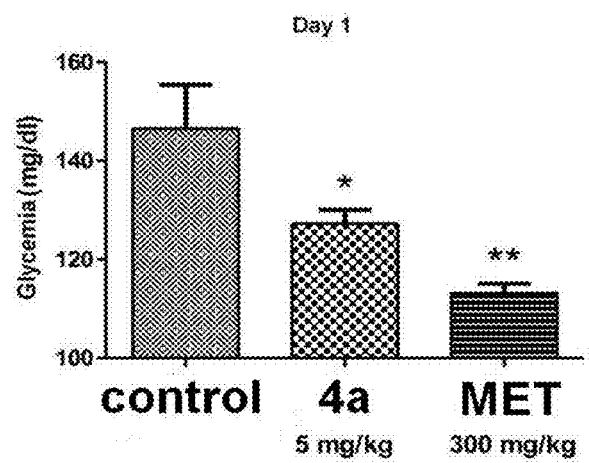
Figure 3:
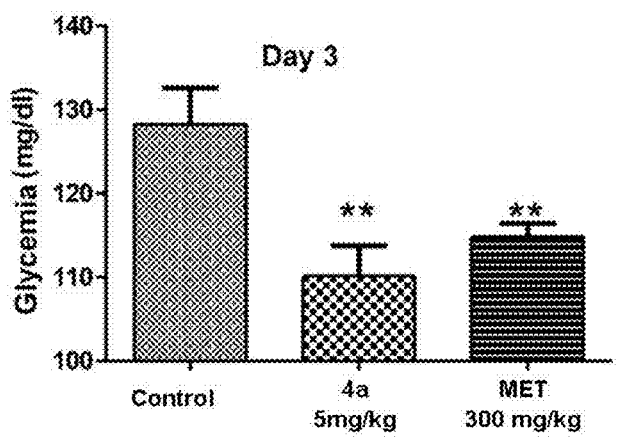

FIG. 3: Hypoglycemic effect of N(-ethylamine)-1-benzosubstituted-β-carboline-3-carboxamide (compound 4a or ANIS-NH2), 1 (A) and 3 (B) days after being administered orally to experimental animals at 5 mg/kg dose compared to the increase of glycemia induced by the glucose overload in normal rats (control) and the glycemia reduction achieved with metformin (MET). Each bar represents the mean±SEM of 6 animals. *P<0.05, **P<0.01 compared with vehicle-treated control group.

Figure 4:
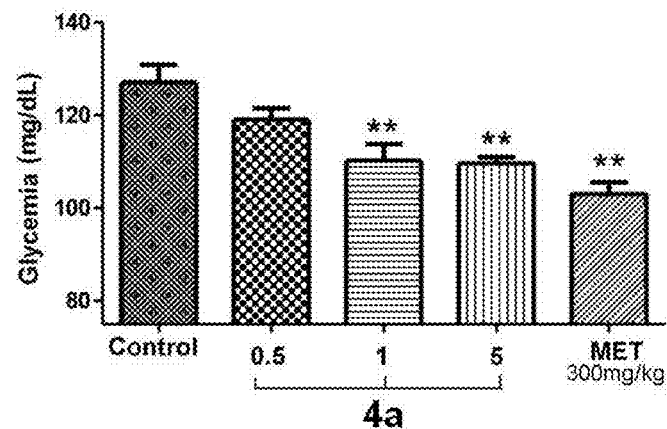

FIG. 4: Hypoglycemic effect after 3 days, of N(-ethylamine)-1-benzosubstituted-β-carboline-3-carboxamide (compound 4a or ANIS-NH2) at 0.5, 1 and 5 mg/kg doses compared to the increase of glycemia induced by glucose overload in normal rats and the glycemia reduction achieved with metformin (MET). Each bar represents the mean±SEM of 6 animals. **P<0.01 compared with vehicle-treated control group.

Figure 5:
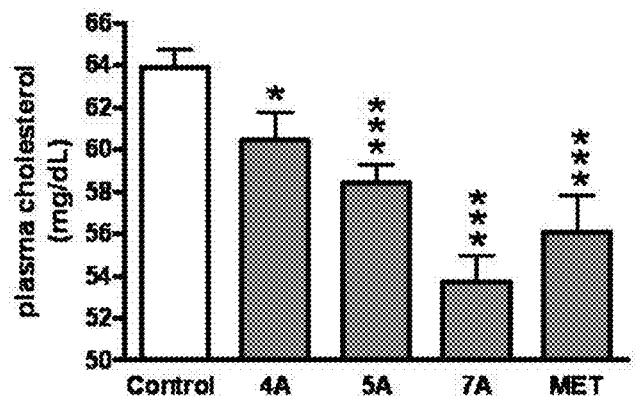

FIG. 5: Plasma cholesterol levels in SHR hypertensive rats treated with 4a or 5a or 7a at doses of 5 mg/kg the first 4 days, 10 mg/kg during the next 4 days and 15 mg/Kg until the end of the treatment period (25 days) or with metformin (MET) (positive control dissolved in water at 300 mg/Kg) compared with plasma cholesterol levels of untreated SHR rats (vehicle or control). Each bar represents the mean±SEM of 6 animals. *P<0.05 and ***P<0.001 compared with vehicle-treated control group.

Figure 6:
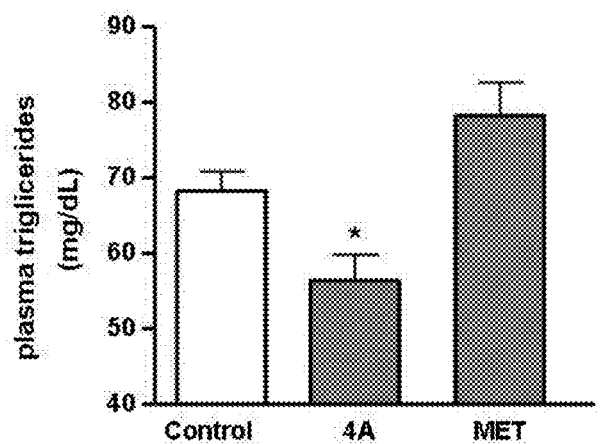

FIG. 6: Plasma triglycerides levels in SHR hypertensive rats treated with 4a at doses of 5 mg/kg the first 4 days, 10 mg/kg during the next 4 days and 15 mg/Kg until the end of the treatment period (25 days) or with metformin (MET) (positive control dissolved in water at 300 mg/Kg) compared with plasma cholesterol levels of untreated SHR rats (vehicle or control). Each bar represents the mean±SEM of 6 animals. *P<0.05 compared with vehicle-treated control group.

Figure 7:
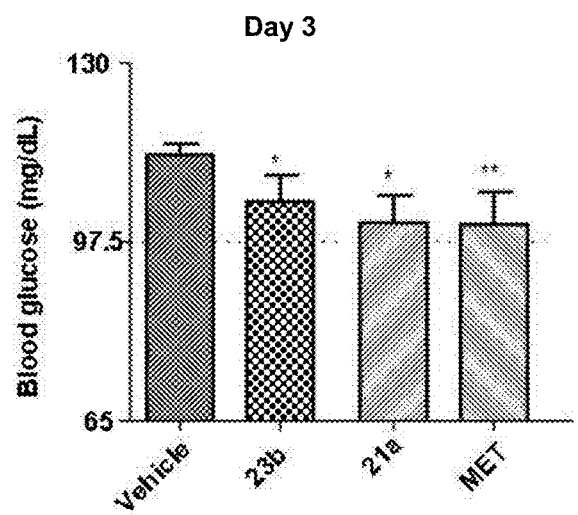

FIG. 7: Hypoglycemic effect of compounds 23b or 21a; 3 days after being administered orally to experimental animals at 10 mg/kg doses compared to the increase of glycemia induced by the glucose overload in normal rats (vehicle-treated control group) and the glycemia reduction achieved with metformin (MET). Each bar represents the mean of six animals and the vertical lines show the S.E.M. *P<0.05; P<0.01; *P<0.001) compared with vehicle-treated control group.

Figure 8:
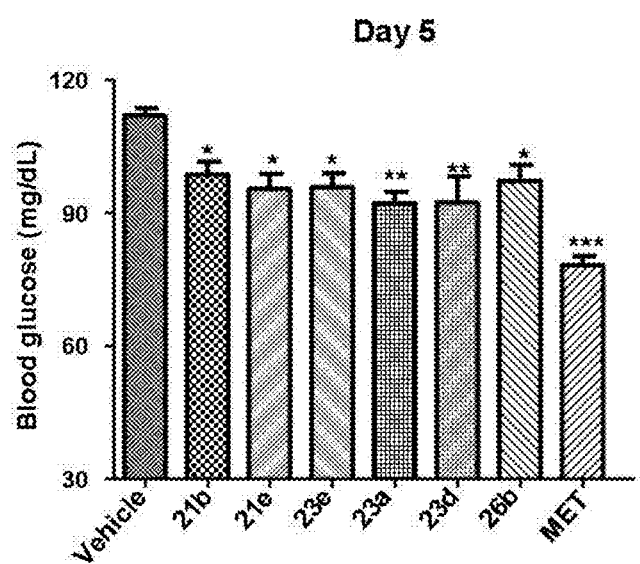

FIG. 8: Hypoglycemic effect of compounds 21b, 21e, 23e, 23a, 23d or 26b; 5 days after being administered orally to experimental animals at 10 mg/kg doses compared to the increase of glycemia induced by the glucose overload in normal rats (vehicle-treated control group) and the glycemia reduction achieved with metformin (MET). Each bar represents the mean of five-eight animals and the vertical lines show the S.E.M. Asterisks denote the significance levels in comparison with the vehicle-treated control group (one-way ANOVA followed by Newman-Keuls test). (*p<0.05; p<0.01, *p<0.001).

DEFINITIONS

According to the invention, the term "metabolic syndrome" as used herein, refers to a collection of factors (metabolic abnormalities), such as hypertension, obesity, hyperlipidemia, diabetes, central obesity, hyperglycemia, hypertension, and hepatic steatosis among others, associated with increased risk for cardiovascular disease. Metabolic syndrome is becoming increasingly common, largely as a result of the increase in the prevalence of obesity (4). The International Diabetes Foundation definition of metabolic syndrome is central obesity (body mass index>30 kg/m$^2$) and two or more of: 1) triglycerides>150 mg/dL; 2) high density lipoprotein (HDL)<40 mg/kL in males, <50 mg/dL in females, or specific treatment for low HDL; 3) elevated blood pressure (BP), e.g., systolic BP>130 mm Hg or diastolic BP>85 mm Hg, or treatment for elevated BP, or previous diagnosis of elevated BP; and 4) fasting blood glucose >100 mg/dL or previous diagnosis of type 2 diabetes. For the purposes of present patent application terms as "metabolic syndrome", "metabolic disease" or "metabolic disorders" should be taken as sinonimus.

According to the invention, the term "diabetes" as used herein, refers to group of metabolic diseases in which a person has high blood sugar, either because the body does not produce enough insulin, or because cells do not respond to the insulin that is produced. There are three main types of diabetes: (1) Type 1 diabetes (T1D): results from the body's failure to produce insulin, and presently requires the person to inject insulin. (Also referred to as insulin-dependent diabetes mellitus, IDDM for short, and juvenile diabetes.) (2) Type 2 diabetes T2D): results from insulin resistance, a condition in which cells fail to use insulin properly, sometimes combined with an absolute insulin deficiency. (Formerly referred to as non-insulin-dependent diabetes mellitus, NIDDM for short, and adult-onset diabetes.) (3) Gestational diabetes (GD): is when pregnant women, who have never had diabetes before, have a high blood glucose level during pregnancy. It may precede development of T2D.

According to the invention, the term "hyperlipidemia or hyperlipoproteinemia, or hyperlipidaemia" as used herein refers to a condition of abnormally elevated levels of any or all lipids and/or lipoproteins in the blood.

According to the invention, the term "hypercholesterolemia" as used herein refers to the presence of high levels of cholesterol in the blood. It is closely related to the terms "hyperlipidemia" (elevated levels of lipids in the blood) and "hyperlipoproteinemia" (elevated levels of lipoproteins in the blood).

According to the invention, the term "hypertriglyceridemia" as used herein refers to a high level of all glycerides, including monoglycerides, diglycerides and triglycerides. It has been associated with cardiovascular diseases, i.e. atherosclerosis, even in the absence of hypercholesterolemia (high cholesterol levels).

According to the invention, the term "hypertension or high blood pressure or arterial hypertension" as used herein refers to a chronic medical condition in which the blood pressure in the arteries is elevated. This requires the heart to work harder than normal to circulate blood through the blood vessels. Normal blood pressure at rest is within the range of 100-140 mmHg systolic (top reading) and 60-90 mmHg diastolic (bottom reading). High blood pressure is said to be present if it is persistently at or above 140/90 mmHg. Hypertension is a major risk factor for stroke, myocardial infarction (heart attacks), heart failure, aneurysms of the arteries (e.g. aortic aneurysm), peripheral arterial disease and is a cause of chronic kidney disease. Even moderate elevation of arterial blood pressure is associated with a shortened life expectancy.

According to the invention, the term "obesity or central obesity" as used herein refers to a medical condition in which excess body fat has accumulated to the extent that it may have an adverse effect on health, leading to reduced life expectancy and/or increased health problems. Body mass index (BMI), a measurement which compares weight and height, defines people as overweight (pre-obese) if their BMI is between 25 and 30 kg/m$^2$, and obese when it is greater than 30 kg/m$^2$.

According to the invention, the term "nutraceutical or nutraucetic food" refers to any substance that could be a food or a part of a food and provides medical or health benefits, including the prevention and treatment of a disease,

DETAILED DESCRIPTION

The invention is described hereto throughout the following examples which have no limitative, but demonstrative, purposes.

Example 1

Process synthesis of 1-benzosubstituted-tetrahydro-β-carbolinic-3-carboxylic acid derivatives (compounds 1a and 1b)

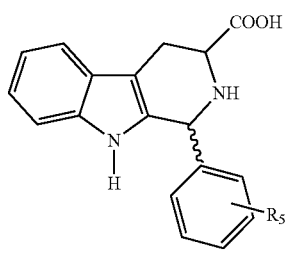

(1a) R$_5$ = p-OCH$_3$ (p = "para" position)
(1b) R$_5$ = H

The derivatives 3-carboxi-tetrahydro-β-carbolinic-1-benzosusbtituted (compounds 1a and 1b), were obtained through condensation of commercial L-tryptophan (5.0 mmol), with 1.1 equivalents of the following aldehydes: anisaldehyde (a) and benzaldehyde (b). The mixture was kept under reflux for approximately 2 hours in glacial acetic acid (20 ml), afterwards the pH was adjusted to pH=5 with concentrated ammonium hydroxide and the resulting precipitation washed with water and filtered in a Büchner's funnel. The reactions provided the mixture of cis and trans products (R-β and R-α group). The products 1a or 1b were obtained with a 92% and 87% yield, respectively.

Example 2

Process synthesis of methyl-1-benzosubstituted-tetrahydro-β-carbolinic-3-carboxylate derivatives (compounds 2a and 2b)

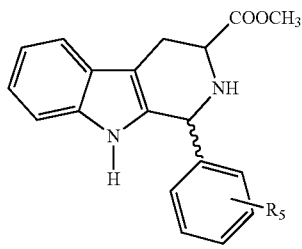

(2a) R$_5$ = p-OCH$_3$
(2b) R$_5$ = H

To a solution of 3-carboxi-tetrahydro-β-carbolinic-1-benzosubstituted (compounds 1a and 1b) (3.5 mmol), in MetOH (10 ml), 1.0 ml of H$_2$SO$_4$ concentrated was added. The solution was kept under reflux and agitation for approximately 48 hrs. After evaporation of all methanol, the resulting product was neutralized with a solution of sodium bicarbonate 10%. The organic phase was extracted with ethyl acetate (3×10 ml), dried up with sodium sulfate anhydrate and, after filtering off the drying agent, the solvent was removed by means of a rotation-evaporator. The compounds (2a or 2b) were obtained, respectively, with an 82 to 87% output.

Example 3

Process synthesis of methyl 1-benzosubstituted-ρ-carbolinic-3-carboxylate derivatives (compounds 3a or 3b)

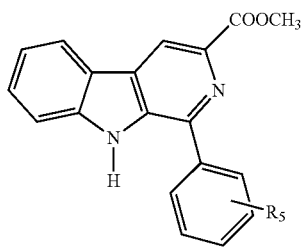

(3a) R$_5$ = p-OCH$_3$
(3b) R$_5$ = H

To a solution of 2.0 mmol of methyl-tetrahydro-β-carbolinic-3-carboxylate (compounds 2a or 2b), in xylene (25 ml), 2.5 sulfur equivalents were added. The solution was kept under reflux and agitation for 12 hours and afterwards, 3 hours at 0° C. under agitation. The formed precipitation was filtered in a Büchner's funnel and washed with petroleum ether. The products (3a and 3b) were obtained with a yield ranging 70 to 73%.

Example 4

Process synthesis of N(-ethylamine)-1-benzosubstituted-β-carboline-3-carboxamide (compound 4a) and N(-propylamine)-1-benzosubstituted-β-carboline-3-carboxamide (compound 5a)

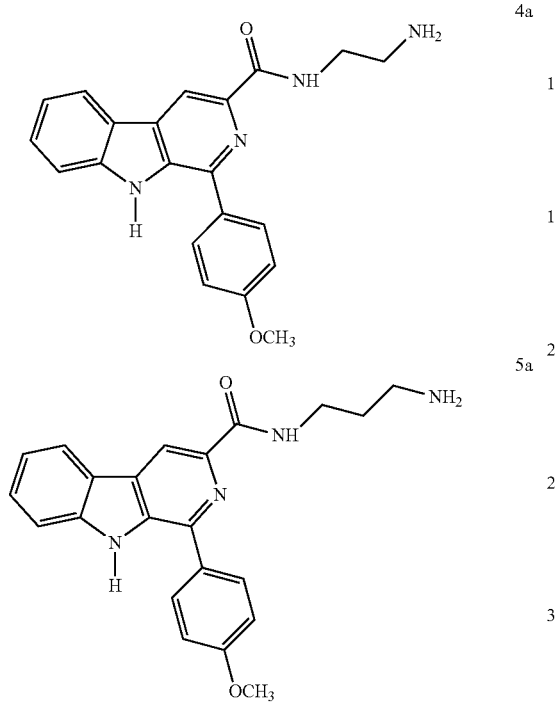

The compound 3a (2.0 mmol) with approximately 6.0 ml of ethylenediamine, was agitated at room temperature for 24 hours. After amine evaporation and recrystallization with methanol, it provided the 4a compound with an output of 55%.

The propylamine-β-carbolinic derivative (compound 5a) was obtained by the addition to the methyl-β-carbolinic-3-carboxilate derivative (compound 3a) (1.7 mmol) an equimolar amount of propylenediamine in CHCl$_3$/MeOH 1:1 under reflux, for approximately 32 hours. The reaction was monitored by thin layer chromatography. After evaporation of all chloroform and methanol, in a rotating evaporator, the product was recrystallized with methanol/acetone, obtaining an overall yield of 68%.

Example 5

Process synthesis of N-(hydrazyl)-1-benzosubstituted-β-carbolinic-3-carbohydrazide (compounds 6a and 6b)

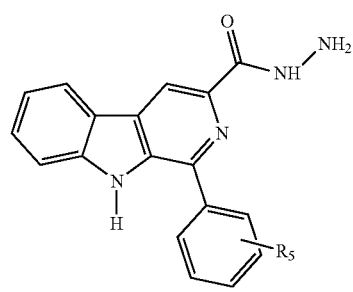

(6a) R$_7$ = p-OCH$_3$
(6b) R$_7$ = H

To a solution of (3a) or (3b) compounds (2.97 mmol) in ethanol (40 ml), 48.2 mmol of hydrated hydrazine were added. The reaction mixture was kept under reflux for 72 hours. The formed precipitation was filtered in a Büchner funnel and washed with ethanol. The products 6a and 6b were obtained with a yield ranging 72 to 76%.

Example 6

Process synthesis of 3-(carbohydrazyl-n'-phenylsubstituted)-1-benzosubstituted-β-carbolinic-3-carbohydrazide (compounds 7a and 7b)

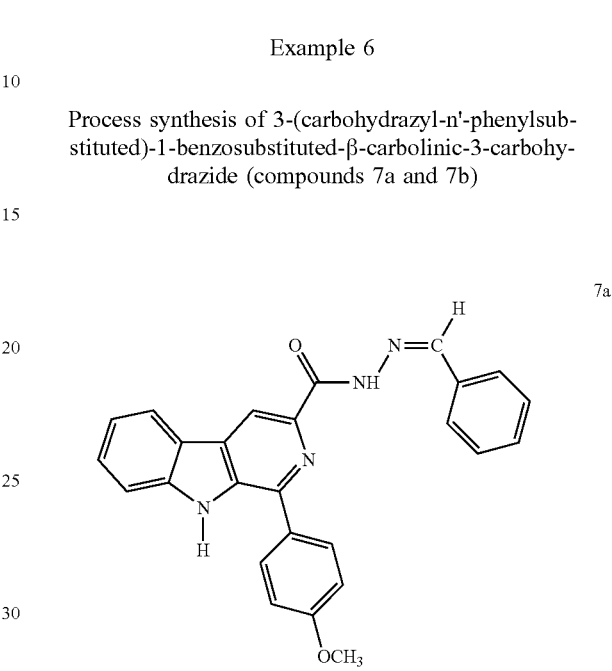

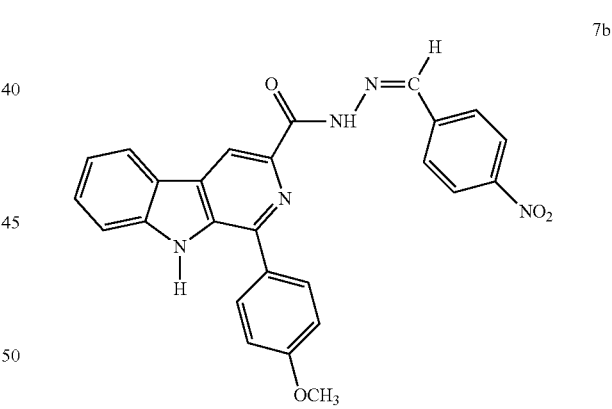

To a solution of N-hydrazyl-β-carbolinic (1.0 mmol) derivatives either (compound 6a) or (compound 6b) in water (10 ml), 2 drops of concentrated sulfuric acid were added. The mixture was kept under agitation, at 65° C., until complete solubilization. Afterwards, 1.50 mmol of the respective aromatic aldehydes (benzaldehyde for compound 6a or p-nitrobenzaldehyde for compound 6b) in ethanol (10 ml) were added and the solution was kept in reflux for 24 hours. The mixture was put in ice-bath and neutralized with a 10% sodium bicarbonate solution and the formed precipitate was filtered in a Buchner's funnel and recrystallized with methanol. The products 7a and 7b were obtained with a yield ranging of 58 to 60%.

Example 7

Process Synthesis of Compound 17a (IFC-1201-04)

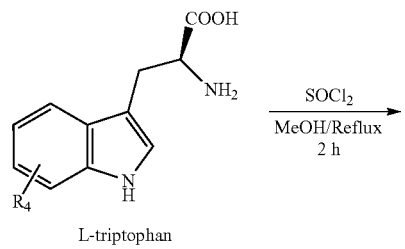

L-triptophan

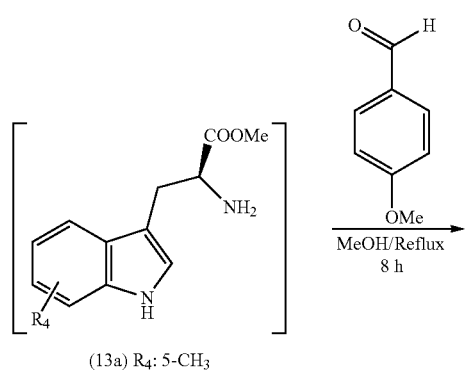

(13a) R₄: 5-CH₃

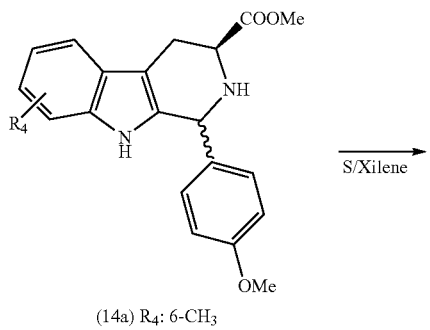

(14a) R₄: 6-CH₃

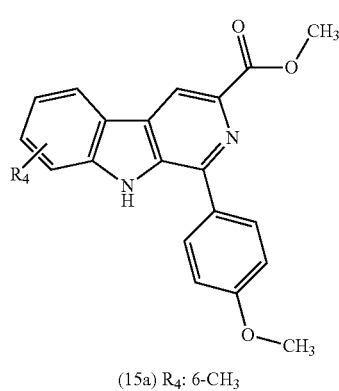

(15a) R₄: 6-CH₃

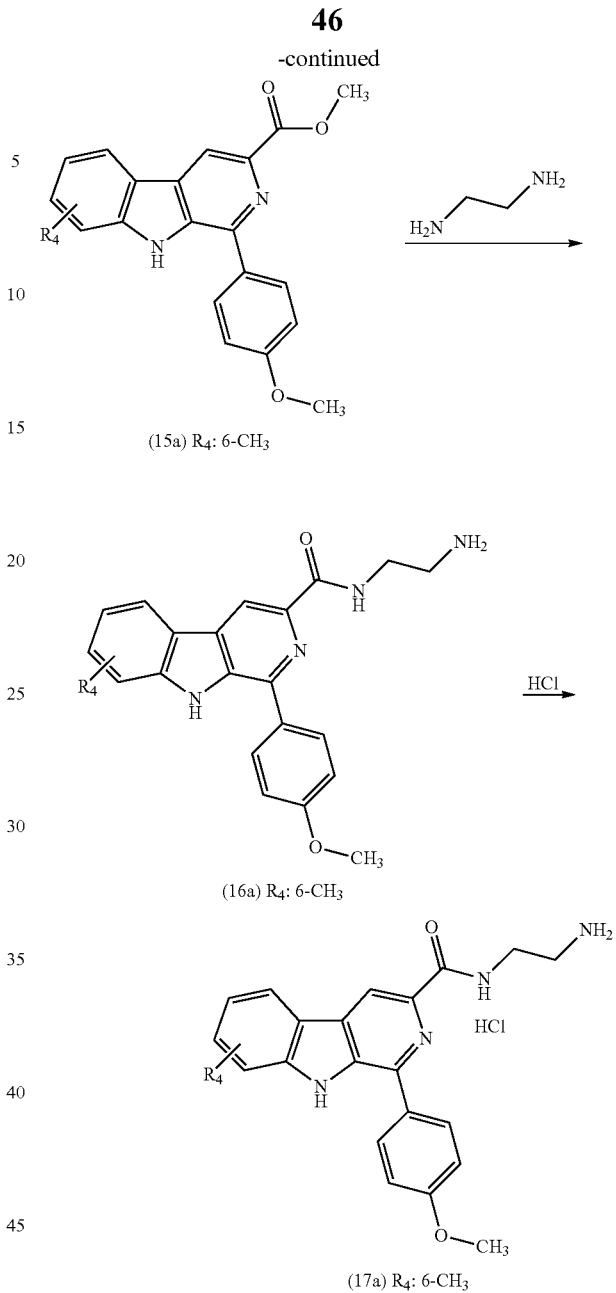

To a suspension of 5-Methyl-DL-triptofan (1 g; 4.58 mmol) in MeOH (10 mL) at 0° C. thionyl chloride (0.4 mL; 5.49 mmol) was added drop-wise. Mixture was refluxed (80° C.). After 4 hours p-anisaldehyde was added over the heating solution (613 mg; 5.03 mmol.) in portions. HPLC-MS after 10 hours showed two diastereoisomers. The mixture was cooled to room temperature and was concentrated to dryness. The resulting crude was dissolved in water (50 mL). DCM was added (20 mL) and saturated NaHCO3 was added until pH=7. The layers were separated and the aqueous phase was extracted with DCM. The organic layers were washed with H2O and brine. The layers were separated and organic layer was dried over Na2SO4, filtered and concentrated to dryness. The residue was purified by flash chromatography (SiO2, Hexane/acetona 20%) obtaining 837 mg of the mixture of diastereoisomers. Yield: 52%. HPLC-Ms: 99% (IFC-1201-01CF2)

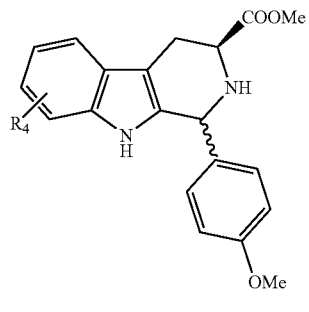

(14a)

R₄: 6-CH₃

To a solution of compound 14a (820 mg; 2.37 mmol) in Xilene (mixture; 40 mL) was added sulphur (229 mg; 7.11 mmol). The mixture was refluxed. HPLC after 20 hours showed total conversion. The reaction was cooled and stirred for 2 hours. The solid formed was filtered. This solid was washed with petroleum ether. 597 g of compound 15a were obtained. Yield: 73%, HPLC-Ms: 98%. (IFC-1201-03S1) Melting point (M.p.): 285-286° C.

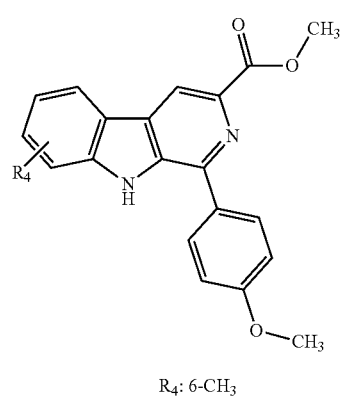

(15a)

R₄: 6-CH₃

Compound 15a (597 mg, 1.72 mmol) was dissolved in ethylendiamine (4.6 mL, 69 mmol). The reaction mixture was stirred at room temperature overnight. HPLC-Ms showed total conversion. The solvent was evaporated to dryness and the solid obtained was dried in oven at 45° C. 552.9 mg of compound 16a were obtained. Yield: 86%, HPLC-Ms: 98%. (IFC-1201-04 free base) M.p.: 207-208° C.

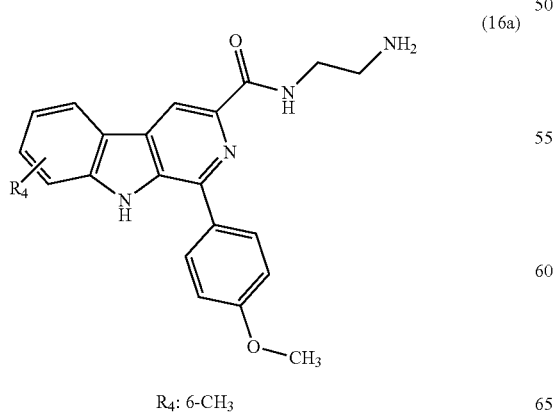

(16a)

R₄: 6-CH₃

Finally, 520 mg (1.39 mmol) of compound 16a were dissolved in ethanol (13 mL) and HCl 1.25M in ethanol (5 mL) was added dropwise at room temperature for 2 hours. The solid formed was filtered obtaining 489 mg of compound 17a (IFC-1201-04) Yield: 96%, HPLC-Ms: 98%. (IFC-1201-04) M.p.: 255-256° C.

Example 8

Process Synthesis of Compound 17b (IFC-1201-05)

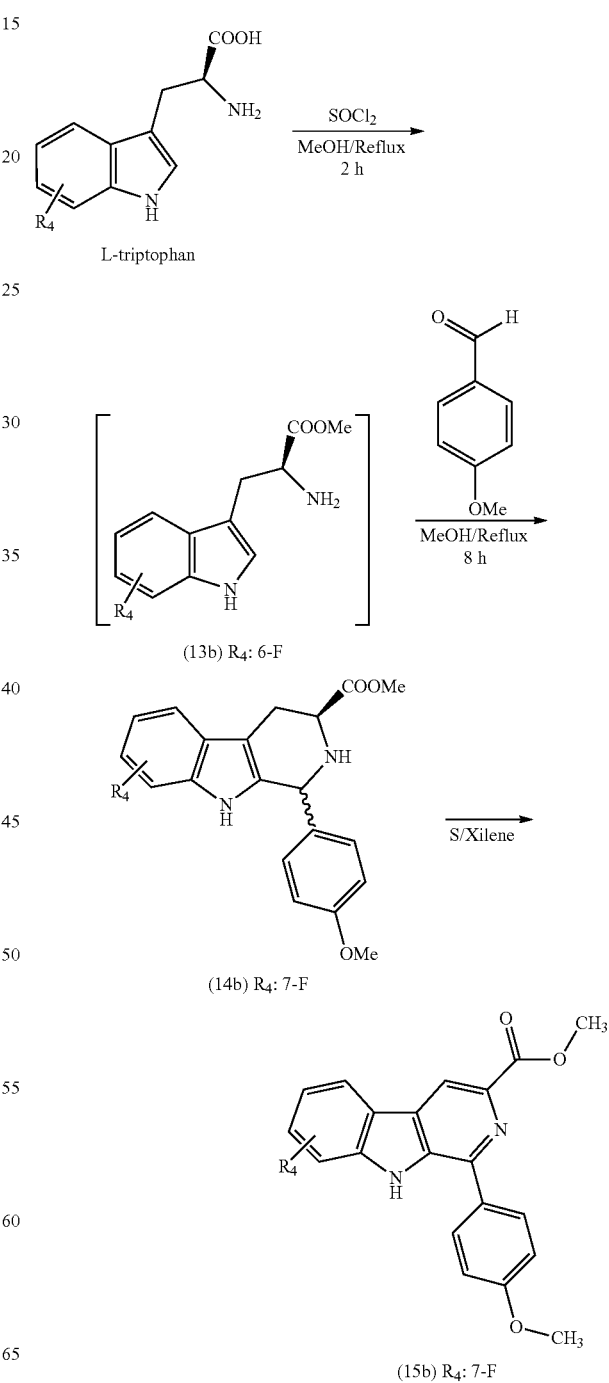

-continued

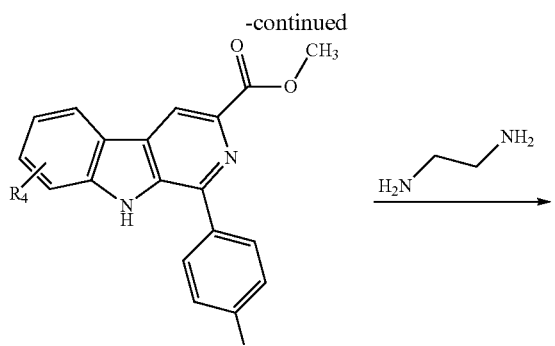

(15b) R₄: 7-F

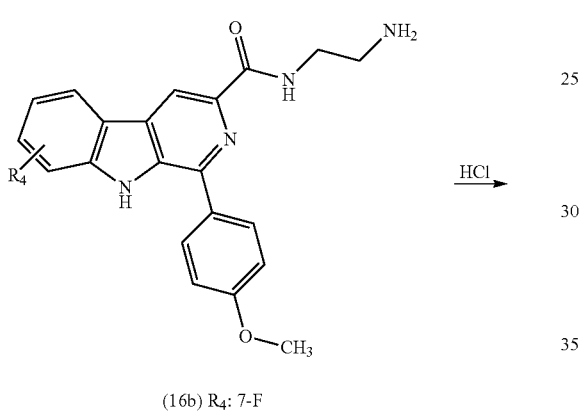

(16b) R₄: 7-F

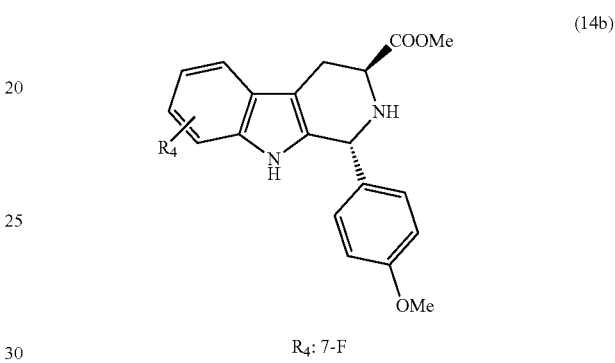

(14b)

R₄: 7-F

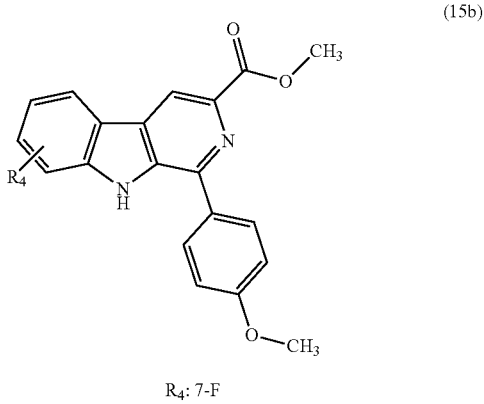

(15b)

R₄: 7-F

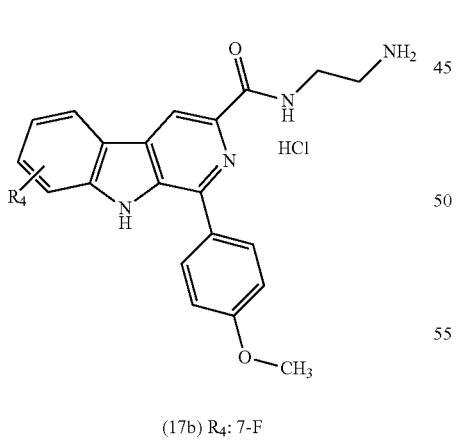

(17b) R₄: 7-F mg; 1.1 equiv.) and the mixture was stirred overnight. HPLC-MS after 14 hours showed two diastereoisomers (66%).

The mixture was cooled to room temperature and was concentrated to dryness. The resulting crude was partitioned between water (50 mL) and DCM (20 mL), and saturated NaHCO3 was added until pH=7. The layers were separated and the aqueous phase was extracted with DCM (2×20 ml). The organic layers were washed with $H_2O$ and brine, dried over $Na_2SO_4$, filtered and concentrated to dryness. The residue (1.9 g) was purified by flash chromatography ($SiO_2$, Hexane/AcOEt 2:1→0:2) obtaining 870 mg of the mixture of compound diastereoisomers (14b or JHG-1117-50CF2). Yield: 36%. HPLC-Ms: 91%.

To a solution of compound 14b (860 mg; 2.43 mmol) in Xilene (mixture; 31 mL) was added sulphur (390 mg; 12.14 mmol). The mixture was vigorously refluxed. HPLC after 16 hours showed total conversion. The reaction was cooled in the fridge overnight. The solid formed was filtered and washed with petroleum ether (2×20 ml) to obtain 620 mg of desired compound 15b (JHG-1117-54S). Yield: 73%, HPLC-Ms: 100%. M.p.: 275-276° C.

Compound 15b (580 mg; 16.57 mmol) was dissolved in ethylenediamine (4.4 mL; 66.29 mmol) and the mixture was stirred at room temperature for 16 hours. TLC shows total conversion. The mixture was concentrated to dryness and the residue was triturated with stirring with water (25 ml) overnight. White solid was filtered and dried to affort 550 mg (HPLC-MS 97%; Yield: 88%) of compound 16b (JHG-1117-57T). M.p.: 186-187° C.

To a suspension of 6-Fluor-D,L-triptofan (1.5 g; 6.75 mmol) in MeOH (7.5 mL) at 0° C., thionyl chloride (0.6 mL; 8.1 mmol) was added dropwise. The mixture was refluxed for 4 hours. HPLC-MS showed no starting material and p-anisaldehyde was added over the heating solution (756

(16b)

R₄: 7-F

Finally, compound 16b (510 mg; 1.35 mmol) was dissolved in ethanol (13 mL) and HCl 1.25 M in EtOH (5 mL) was added. A yellow solid was formed. The suspension was stirred at room temperature for 3 hours and filtered. Product was obtained as yellow solid 17b (IFC-1201-05): 528 mg; HPLC-MS 99%. Yield: 97%. M.p.: 249-250° C.

(17b)

R₄: 7-F

Example 9

Process Synthesis of Compound 17c (IFC-1201-07)

L-triptophan $\xrightarrow{\text{SOCl}_2}{\text{MeOH/Reflux} \atop 2\text{ h}}$

-continued (13c) R₄: 6-OCH₃

$\xrightarrow{\text{MeOH/Reflux} \atop 8\text{ h}}$ (14c) R₄: 6-OCH₃

$\xrightarrow{\text{S/Xilene}}$ (15c) R₄: 6-OCH₃

(15c) R₄: 6-OCH₃

$\xrightarrow{\text{H}_2\text{N}\frown\text{NH}_2}$

-continued

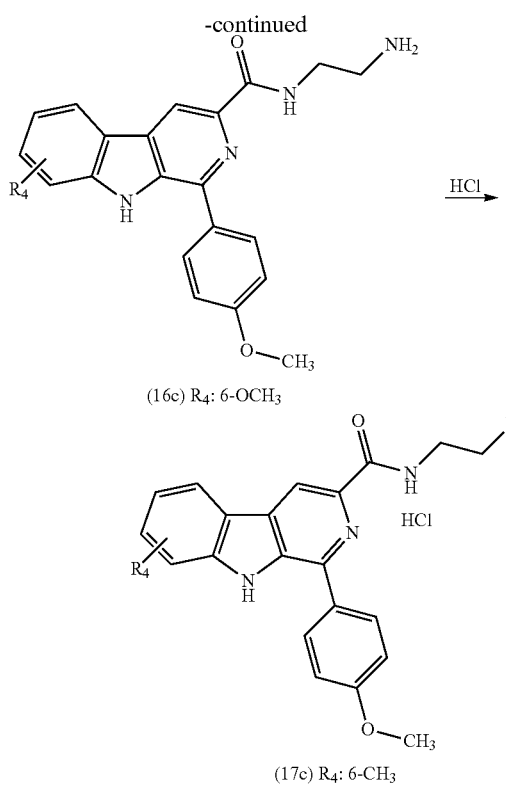

(16c) R₄: 6-OCH₃

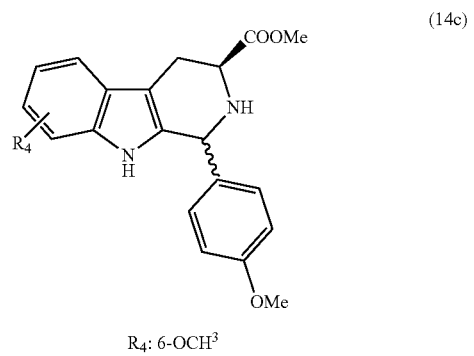

(17c) R₄: 6-CH₃

To a suspension of 5-Methoxy-L-tryptophan (1 g; 4.27 mmol) in MeOH (5 mL) at 0° C. thionyl chloride (0.37 mL; 5.12 mmol) was added dropwise. The mixture was refluxed for 4 hours. HPLC-MS showed no starting material. P-anisaldehyde was added over the heating solution (756 mg; 1.1 equiv.) and the mixture was stirred overnight. HPLC-MS after 14 hours showed two diastereoisomers (79%).

The mixture was cooled to room temperature and was concentrated to dryness. The resulting crude was dissolved in water (50 mL). DCM was added (20 mL) and saturated NaHCO₃ was added until pH=7. The layers were separated and the aqueous phase was extracted with DCM. The combined organic layers were washed with H2O and brine, dried over Na₂SO₄, filtered and concentrated to dryness. The residue (1.85 g) was purified by flash chromatography (SiO₂, Hexane/AcOEt 3:1) obtaining 226 mg of the mixture of diastereoisomers of compound 14c (JHG-1117-49CF1). Yield: 15%. HPLC-Ms: 95%. Another unidentified impurity was obtained (800 mg), likely due to degradation.

(14c)

R₄: 6-OCH³

To a solution of compound 14c (180 mg; 0.49 mmol) in Xilene (mixture; 7 mL) was added sulphur (80 mg; 2.46 mmol). The mixture was refluxed. HPLC after 16 hours showed total conversion. The reaction was cooled and MTBE was added. Solution was stored in the fridge for 2 hours. The solid formed was filtered and washed with petroleum ether to obtain 140 mg of desired compound. Filtrate was concentrated and purified by flash chromatography (SiO2, DCM→DCM/AcOEt 9:1) to obtain additional 14 mg of compound 15c (JHG-1117-56S). Both solids were joined to afford 154 mg. Yield: 87%, HPLC-Ms: 97%.

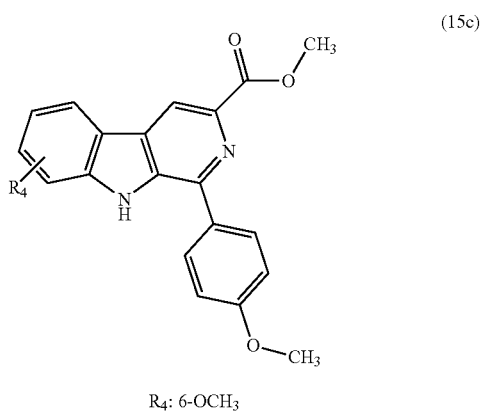

(15c)

R₄: 6-OCH₃

Compound 15c (155 mg; 0.428 mmol) was dissolved in ethylenediamine (1.1 mL; 17.12 mmol) and the mixture was stirred at room temperature for 16 hours. TLC shows total conversion. The mixture was concentrated to dryness coevaporating with additions of H2O and EtOH in order to eliminate the traces of ethylenediamine remaining. Compound 16c (IFC-1201-07 free base) was obtained: 190 mg (HPLC-MS 97%).

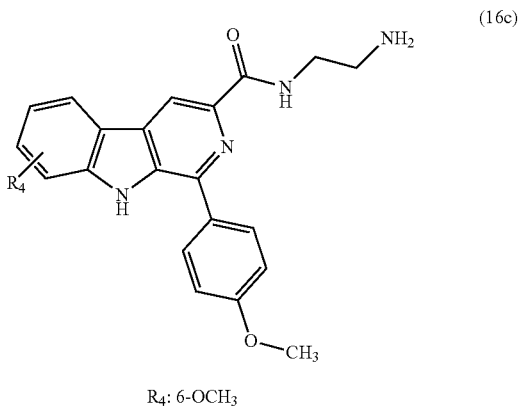

(16c)

R₄: 6-OCH₃

Finally, compound 16c (190 mg; 0.428 mmol) was dissolved in ethanol (4.2 mL) and HCl 1.25 M in EtOH (1.6 mL) was added. A yellow solid was formed. The suspension was stirred at room temperature for 3 hours and filtered. Product was obtained as yellow solid 17c (IFC-1201-07): 160 mg; HPLC-MS 96%. Yield: 90% (IFC-1201-07) M. p.: 215-216° C.

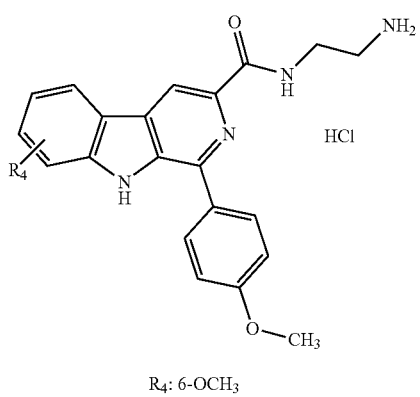

R4: 6-OCH3

Example 10

Process Synthesis of Compound 21a (IFC-1102-79)

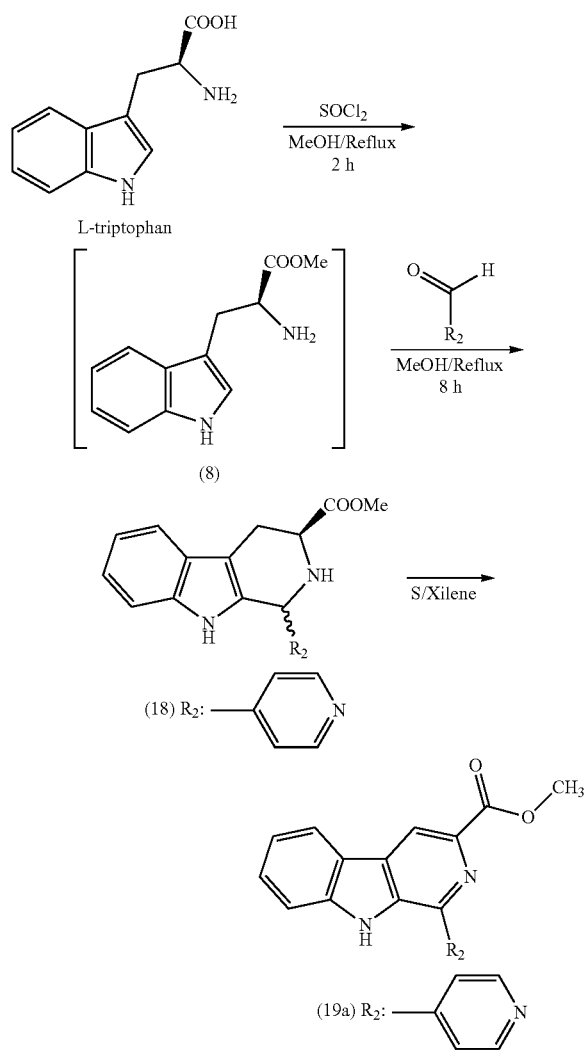

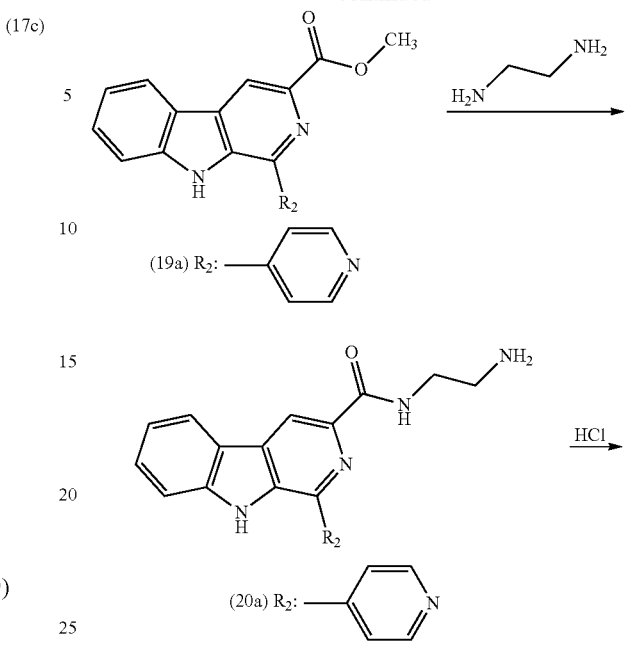

To a suspension of L-tryptophan (700 mg; 3.42 mmol) in MeOH (7 mL) at 0° C. was added thionyl chloride (0.3 mL; 1.2 equiv.) drop-wise. Total solution was observed. The mixture was refluxed (80° C.). HPLC-MS (Liquid chromatography-Mass Spectrometry) after 2 hours showed total conversion to the methyl ester. The aldehyde was added over the heating solution (403 mg; 1.1 equiv.) in portions. The mixture was refluxed for 9 more hours. A yellow solid was observed which makes impossible the stirring. The solid was filtered and washed with MeOH. A yellow solid was obtained: 390 mg. HPLC-MS data indicates that it corresponds to compound 19a (94%; M=303) in hydrochloride form. NMR (Nuclear Magnetic Resonance) spectrum confirms the structure. The solid was dissolved into water and saturated NaHCO3 was added until pH=8. A white solid was observed in suspension. It was filtered to give product 19a (IFC-1102-75S2): 280 mg, HPLC-MS 99%; Yield: 27%. NMR Structure confirmed. The first filtrate from the reaction was concentrated to dryness, solved in water and carried to pH=8 with saturated NaHCO3 solution. A beige solid was obtained. It was filtered to give: 509 mg of a mixture of compound 18a (62%) and 19a (IFC-1102-75S2) (7%).

Compound 19a (180 mg; 0.59 mmol) was dissolved in ethylenediamine (1.6 mL; 40.6 equiv.) and the mixture was stirred at room temperature for 16 hours. TLC (Thin-Layer Chromatography) shows total conversion. The mixture was concentrated to dryness. A beige solid was obtained: 191.5 mg; HPLC-MS 96% product 20a (IFC-1102-79 free base); Yield: 98%.

Finally, compound 20a (188 mg) was dissolved in ethanol (5 mL) and HCl 1.25 M in ethanol (2.3 mL) was added drop-wise. A yellow solid was formed. The suspension was stirred at room temperature for 2 hours and filtered. Product was obtained as yellow solid 21a (IFC-1102-79): 197 mg; HPLC-MS 99%. Yield: 95%. This compound was delivery in two batches.

Example 11

Process Synthesis of Compound 21b (IFC-1102-92)

-continued

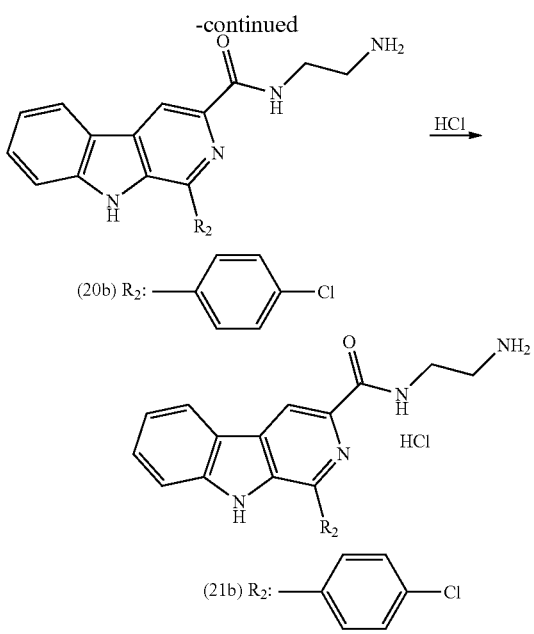

(20b) R₂: —⟨C₆H₄⟩—Cl (21b) R₂: —⟨C₆H₄⟩—Cl

To a suspension of L-tryptophan (1 g; 4.89 mmol) in MeOH (10 mL) at 0° C. was added thionyl chloride (0.43 mL; 1.2 equiv) drop-wise. Total solution was observed. The mixture was refluxed (80° C.). HPLC-MS after 2 hours showed total conversion to the methyl ester. The aldehyde was added over the heating solution (756 mg; 1.1 equiv.) in portions. HPLC-MS after 10 hours showed 3 peaks with the desired Mass. Two of them correspond to the diastereomers of 18b and the other one seems to be the intermediate imine. The mixture was refluxed 8 more hours in order to complete the reaction. HPLC after 8 hours did not show any evolution with 30% of imina. The mixture was cooled to room temperature and was concentrated to dryness. The resulting crude was dissolved in water and saturated NaHCO3 was added until pH=8. A white solid was formed. It was extracted with DCM. The organic layer was washed with water and brine, dried over MgSO4 and concentrated. A white solid was obtained: 1.65 g (HPLC showed product 18b and imine). This solid was purified by flash chromatography to obtain 440 mg of 18b (IFC-1102-82-C2F2) (HPLC-MS 96%); Yield: 28%.

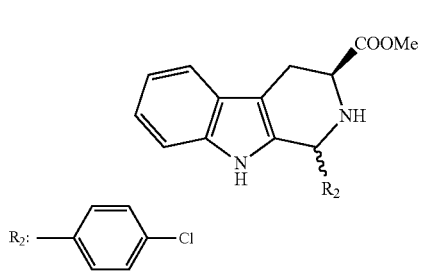

(18b)

To a solution of compound 18b (250 mg; 0.73 mmol) in Xilene (mixture; 12 mL) was added sulphur (64 mg; 2.7 equiv). The mixture was refluxed. HPLC after 20 hours showed little amount of starting material 18b so more sulphur was added (0.7 equiv). HPLC after 4 hours showed total conversion. The reaction was cooled with an ice-water bath for 3 hours. A light red solid was obtained, filtered and washed with petroleum ether. Product 19b (IFC-1102-88S1) was obtained as brown solid: 189 mg; HPLC-MS 99%; Yield: 77%.

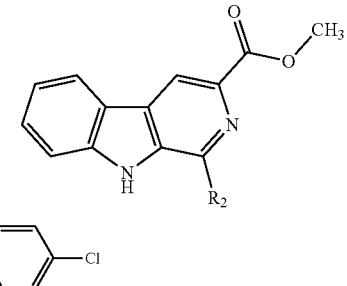

(19b)

R₂: —⟨C₆H₄⟩—Cl

Compound 19b (169 mg; 0.50 mmol) was dissolved in ethylenediamine (1.6 mL; 48 equiv.) and was stirred at room temperature for 16 hours. TLC confirmed total conversion. The mixture was concentrated to dryness. Product 20b was obtained as beige solid: 174 mg; HPLC-MS 98%. RMN showed a little amount of ethylenediamine so it was washed with water, filtered and dried. Pure product 20b (IFC-1102-92 free base) was obtained: 155 mg; Yield: (77%).

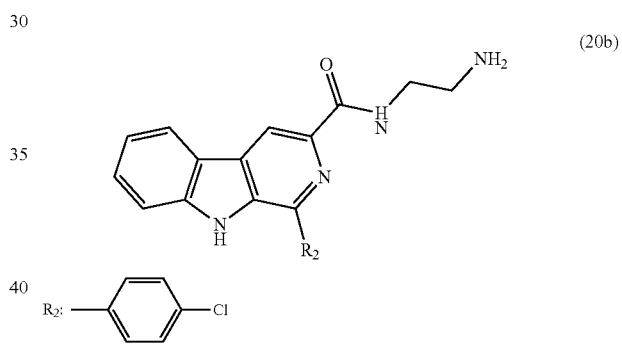

(20b)

R₂: —⟨C₆H₄⟩—Cl

Compound 20b (155 mg; 0.42 mmol) was dissolved in ethanol (5 mL) and HCl 1.25 M in EtOH (2 mL) was added drop-wise. A yellow solid was formed. The suspension was stirred at room temperature for 2 hours and filtered. Product was obtained as yellow solid 21b (IFC-1102-92): 125 mg; HPLC-MS 98%. Yield: 74%. This compound was delivery in two batches.

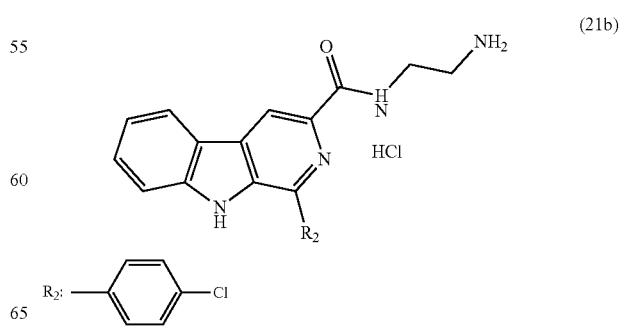

(21b)

R₂: —⟨C₆H₄⟩—Cl

Example 12

Process Synthesis of Compound 21c (IFC-1102-93)

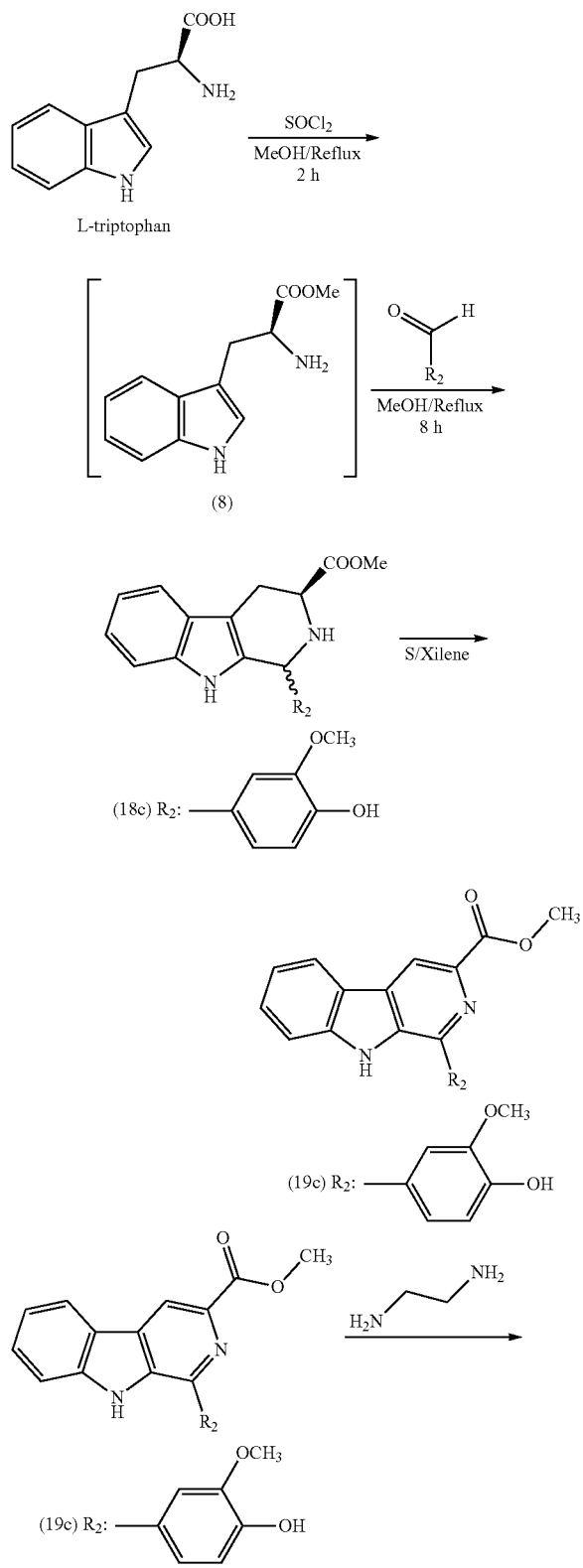

To a suspension of L-tryptophan (1 g; 4.89 mmol) in MeOH (10 mL) at 0° C. was added thionyl chloride (0.43 mL; 1.2 equiv) drop-wise. Total solution was observed. The mixture was refluxed (80° C.). HPLC-MS after 2 hours showed total conversion to the methyl ester. The aldehyde was added over the heating solution (818 mg; 1.1 equiv.) in portions. HPLC-MS after 10 hours showed 3 peaks with the desired Mass. Two of them correspond to the diastereomers of 18c and the other one seems to be the intermediate imine. The mixture was refluxed 8 more hours in order to complete the reaction. HPLC after 8 hours showed little evolution with 12% of imina. The mixture was cooled to room temperature and was concentrated to dryness. The resulting crude was dissolved in water and saturated $NaHCO_3$ was added until pH=8. A white solid was formed. It was filtered and washed with water. A white solid was obtained: 1.03 g (HPLC showed product 18c (80%) and imine). This solid was purified by silica gel chromatography column to obtain 810 mg of 18c (IFC-1102-83CF1) (HPLC-MS 99%); Yield: 47%.

To a solution of compound 18c (250 mg; 0.71 mmol) in Xylene (mixture; 12 mL) was added sulphur (64 mg; 2.8 equiv). The mixture was refluxed. HPLC after 20 hours showed little amount of starting material compound 18c so more sulphur was added (0.7 equiv). HPLC after 4 hours shows total conversion. The reaction was cooled with an ice-water bath for 3 hours. A light yellow solid was obtained, filtered and washed with petroleum ether. Product 19c (IFC-1102-89S1) was obtained as yellow solid: 170 mg; HPLC-MS 92%; Yield: 69%.

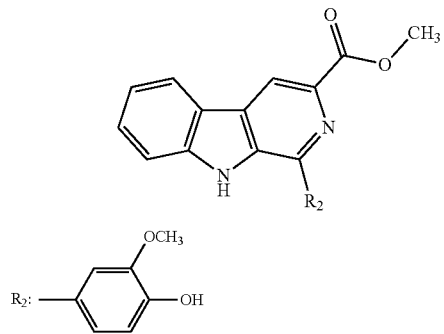

(19c)

Compound 19c (155 mg; 0.44 mmol) was dissolved in ethylenediamine (1.6 mL; 54 equiv.) and was stirred at room temperature for 16 hours. HPLC-MS confirmed total conversion. The mixture was concentrated to dryness. Product 20c (IFC-1102-93 free base) was obtained as beige solid: 160 mg; HPLC-MS 98%; Yield: (97%).

(20c)

Compound 20c (150 mg; 0.40 mmol) was dissolved in ethanol (5 mL) and HCl 1.25 M in EtOH (2 mL) was added drop-wise. A yellow solid was formed. The suspension was stirred at room temperature for 2 hours and filtered. Product was obtained as yellow solid 21c (IFC-1102-93): 133 mg; HPLC-MS 97%. Yield: 72%. (IFC-1102-93). This compound was delivery in two batches.

(21c)

-continued

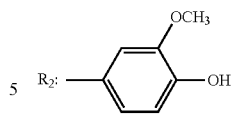

Example 13

Process Synthesis of Compound 21d (IFC-1102-94)

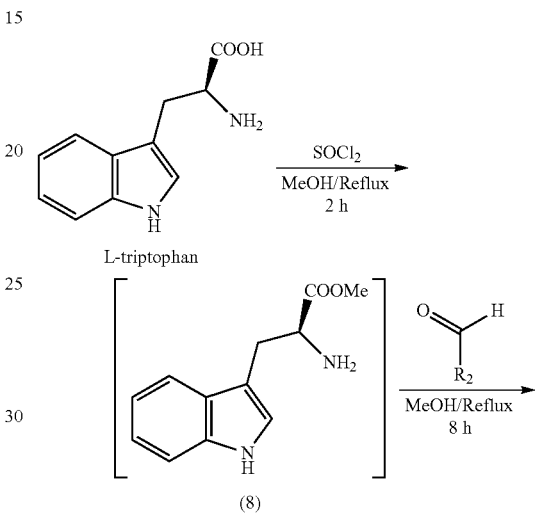

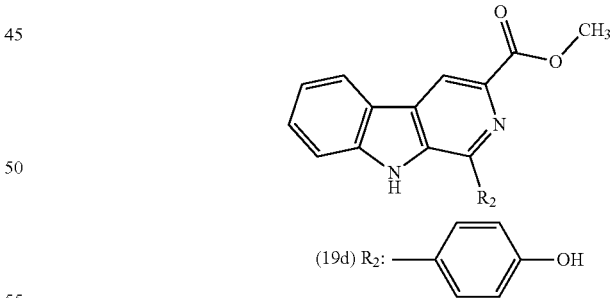

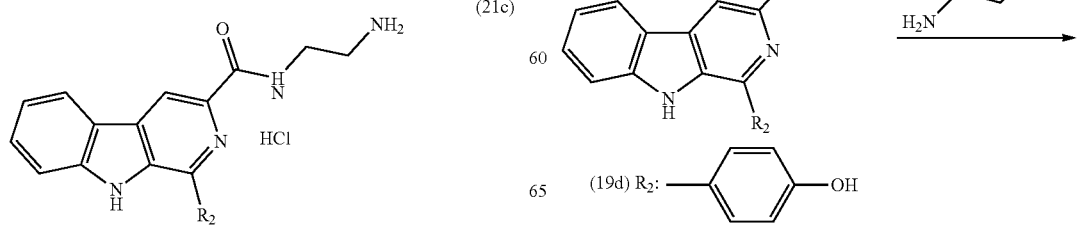

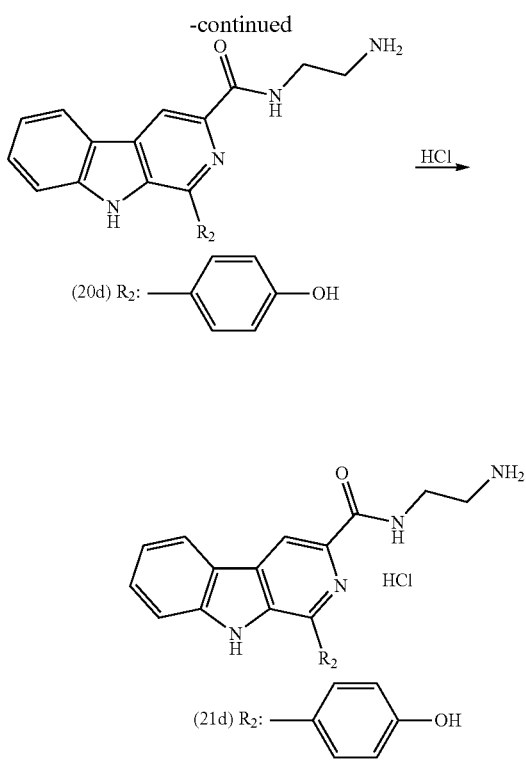

(20d) R$_2$: —⟨⟩—OH

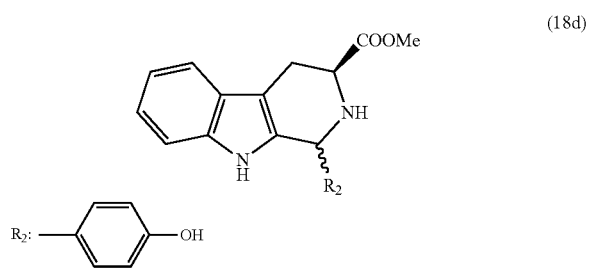

(18d)

R$_2$: —⟨⟩—OH

To a suspension of L-tryptophan (3 g; 14.69 mmol) in MeOH (30 mL) at 0° C. was added thionyl chloride (1.3 mL; 17.9 mmol) drop-wise. Total solution was observed. The mixture was refluxed (80° C.). HPLC-MS after 2 hours showed total conversion to the methyl ester. The aldehyde was added over the heating solution (1.97 g; 16.13 mmol) in portions. HPLC-MS after 28 hours showed total conversion. The mixture was cooled to room temperature and was concentrated to dryness. The resulting crude was dissolved in water and saturated NaHCO$_3$ was added until pH=8. A white solid was formed. It was filtered and washed with water. A brown solid was obtained: 3.45 g (HPLC: 90%). This solid was purified by silica gel chromatography column (SiO2 Hexane/acetone 30%) obtaining 1.08 g of 18d (IFC-1102-85CF1) (HPLC-MS 99%); Yield: 23%.

To a solution of compound 18d (500 mg; 1.55 mmol) in Xylene (mixture; 25 mL) was added sulphur (140 mg; 4.34 mmol). The mixture was refluxed. HPLC after 64 hours showed total conversion. The reaction was cooled to 0° C. overnight. A light yellow solid was obtained, filtered and washed with petroleum ether. Compound 19d (IFC-1102-91S1) was obtained as yellow solid: 170 mg; HPLC-MS 96%; Yield: 82%. M. p.: 260-261° C.

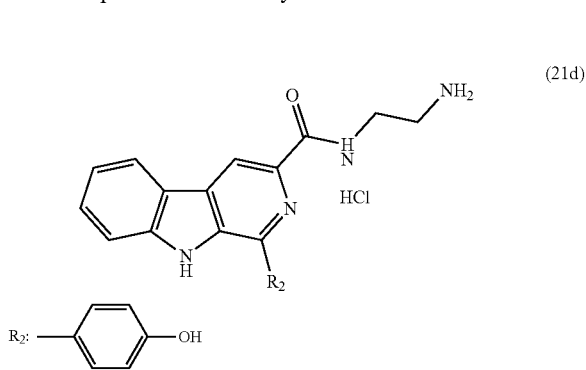

Compound 19d (372 mg; 1.17 mmol) was dissolved in ethylenediamine (3.1 mL; 46.8 mmol.) and was stirred at room temperature overnight. HPLC-MS confirmed total conversion. The mixture was concentrated to dryness. Product 20d (IFC-1102-94 free base) was obtained as beige solid: 417 mg; HPLC-MS 94%; Yield: (quantitative). M. p.: 238-239° C.

Compound 20d (400 mg; 1.15 mmol) was dissolved in ethanol (5 mL) and HCl 1.25 M in EtOH (5 mL) was added drop-wise. A yellow solid was formed. The suspension was stirred at room temperature for 2 hours and filtered. The solid was washed with ethanol and dried in oven at 45° C. Product was obtained as yellow solid 21d (IFC-1102-94): 309 mg; HPLC-MS 98%. Yield: 70%. M.p.: 301-303° C. This compound was delivery in two batches.

Example 14

Process Synthesis of Compound 21e (IFC-1102-96)

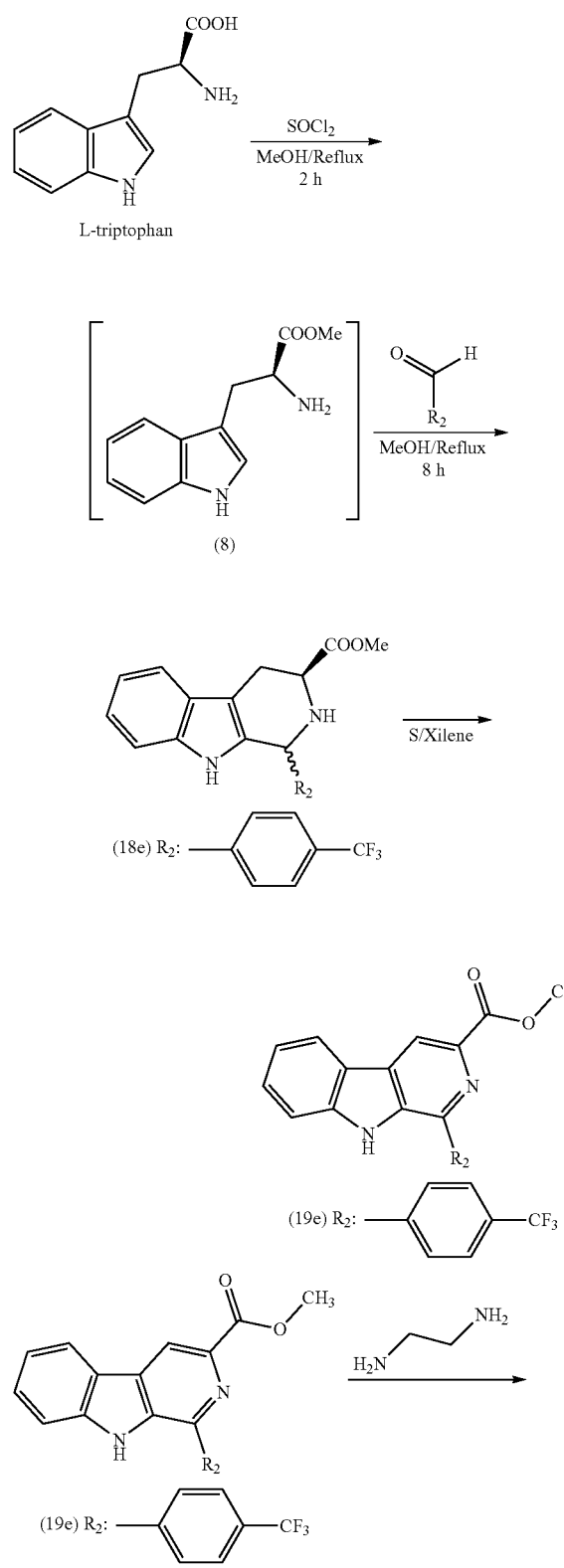

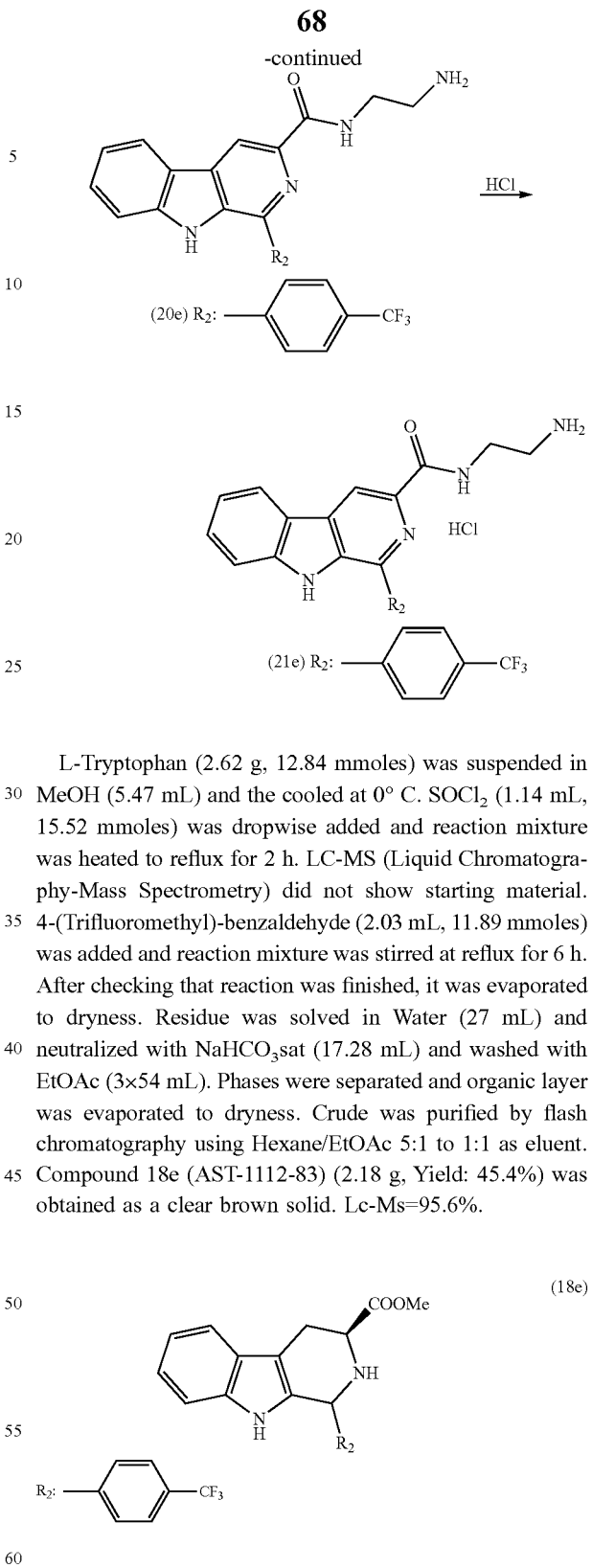

L-Tryptophan (2.62 g, 12.84 mmoles) was suspended in MeOH (5.47 mL) and the cooled at 0° C. SOCl₂ (1.14 mL, 15.52 mmoles) was dropwise added and reaction mixture was heated to reflux for 2 h. LC-MS (Liquid Chromatography-Mass Spectrometry) did not show starting material. 4-(Trifluoromethyl)-benzaldehyde (2.03 mL, 11.89 mmoles) was added and reaction mixture was stirred at reflux for 6 h. After checking that reaction was finished, it was evaporated to dryness. Residue was solved in Water (27 mL) and neutralized with NaHCO₃sat (17.28 mL) and washed with EtOAc (3×54 mL). Phases were separated and organic layer was evaporated to dryness. Crude was purified by flash chromatography using Hexane/EtOAc 5:1 to 1:1 as eluent. Compound 18e (AST-1112-83) (2.18 g, Yield: 45.4%) was obtained as a clear brown solid. Lc-Ms=95.6%.

Compound 18e (2.18 g, 5.82 mmoles) was suspended in a mixture of Xilene (81 mL) and S (0.465 g, 14.55 mmoles) was added. The mixture was refluxed overnight. LC-MS did not show starting material. Reaction mixture was cooled to 4° C. and a solid was filtered and washed with petroleum ether (10 mL). Compound 19e (AST-1112-84) (1.4 g, Yield 65%) was obtained as a brown solid. LC-MS=98.5%.

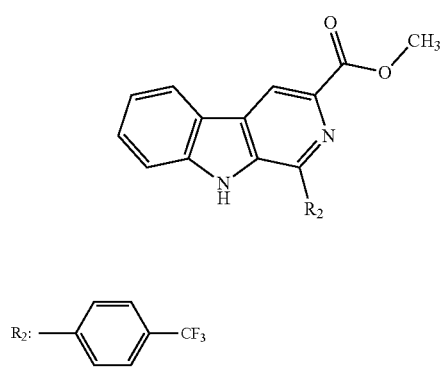

(19e)

R₂: ―⟨benzene⟩―CF₃

Compound 19e (1.0 g; 2.7 mmol) was dissolved in ethylenediamine (7.2 mL; 40 equiv.) and was stirred at room temperature for 16 hours. HPLC-MS confirmed total conversion. The mixture was concentrated to dryness. Product 20e (IFC-1102-96) was obtained as beige solid: 1.07 g; HPLC-MS 98%. Yield: 99%.

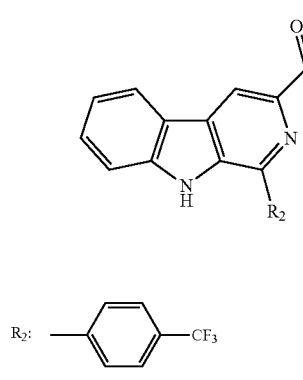

(20e)

R₂: ―⟨benzene⟩―CF₃

Compound 20e (513 mg; 1.28 mmol) was dissolved in ethanol (13 mL) and HCl 1.25 M in EtOH (5 mL) was added drop-wise. A yellow solid was formed. The suspension was stirred at room temperature for 2 hours and filtered. Product 21e (IFC-1102-96) was obtained as a yellow solid: 465 mg; HPLC-MS 98%/0. Yield: 84%. M.p.: 283-284° C.

(21e)

R₂: ―⟨benzene⟩―CF₃

Example 15

Process Synthesis of Compound 21f (IFC-1201-06)

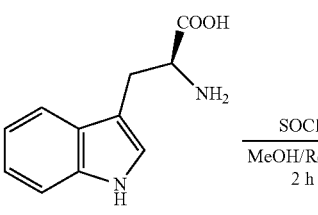

L-triptophan

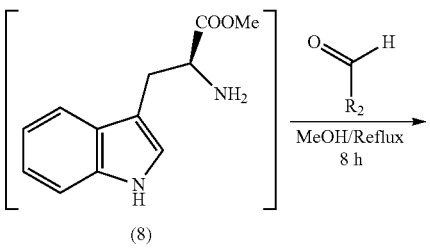

(8)

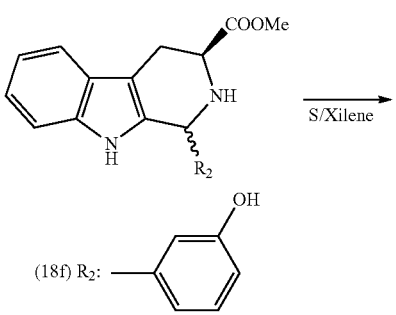

(18f) R₂: ―⟨benzene⟩―OH

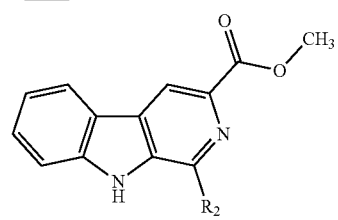

(19f) R₂: ―⟨benzene⟩―OH

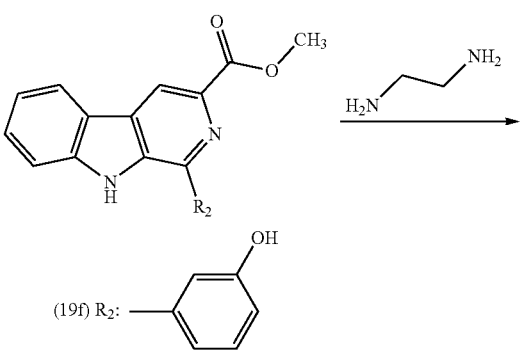

(19f) R₂: ―⟨benzene⟩―OH

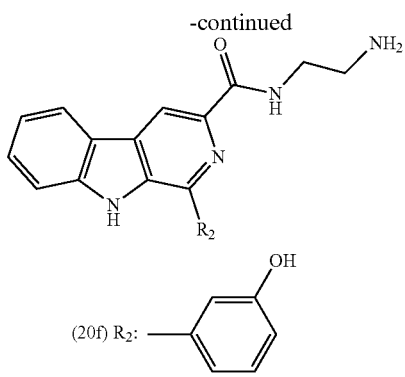

(20f) R₂:

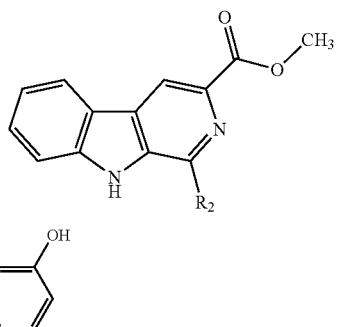

(19f)

R₂:

Compound 19f (263 mg; 0.82 mmol) was dissolved in ethylenediamine (2.6 mL; 39 mmol) and was stirred at room temperature for 16 hours. HPLC-MS confirmed total conversion. The mixture was concentrated to dryness. Product 20f (IFC-1201-06) was obtained as beige solid: 196.8 mg; HPLC-MS 91%. Yield: 75%.

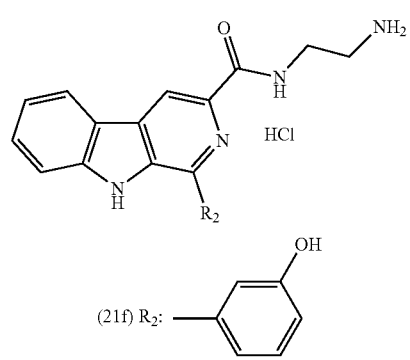

(21f) R₂:

L-Tryptophan (2.00 g, 9.88 mmoles) was suspended in MeOH (20 mL) and the cooled at 0° C. SOCl₂ (0.87 mL, 12 mmoles) was drop-wise added and reaction mixture was heated to reflux for 2 h. LC-MSs did not show starting material. 3-hydroxybenzaldehyde (1.31 g, 10 mmoles) was added and reaction mixture was stirred at reflux overnight. After checking that reaction was finished, it was evaporated to dryness. Residue was solved in Water (27 mL) and neutralized with NaHCO₃sat (17.28 mL). A brown solid was formed and filtered. This solid was purified by flash chromatography using Hexane/Acetone 7:3 to 1:1 as eluent. Compound 18f (IFC-1102-90CF1) (945 mg, Yield: 30%) was obtained as a clear brown solid. Lc-Ms=98%

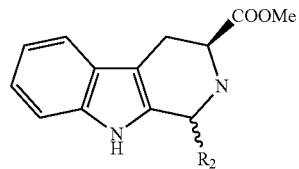

(18f)

R₂:

Compound 18f (445 mg, 1.38 mmoles) was suspended in a mixture of Xilene (25 mL) and S (133 mg, 4.15 mmoles) was added. The mixture was refluxed for 44 hours. Lc-Ms did not show starting material. Reaction mixture was cooled to 4° C. and a solid was filtered and washed with petroleum ether (10 mL). Compound 19f (IFC-1201-02S1) (263 mg, Yield 60%) was obtained as a brown solid. Lc-Ms=90%.

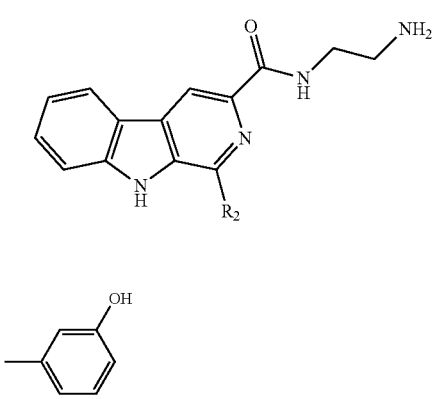

(20f)

R₂:

Compound 20f (196 mg; 0.61 mmol) was dissolved in ethanol (4 mL) and HCl 1.25 M in EtOH (1.5 mL) was added drop-wise. A yellow solid was formed. The suspension was stirred at room temperature for 2 hours and filtered. Product 21f (IFC-1201-06) was obtained as a yellow solid: 108 mg; HPLC-MS 96%. Yield: 52%.

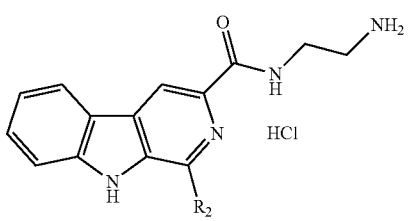

(21f)

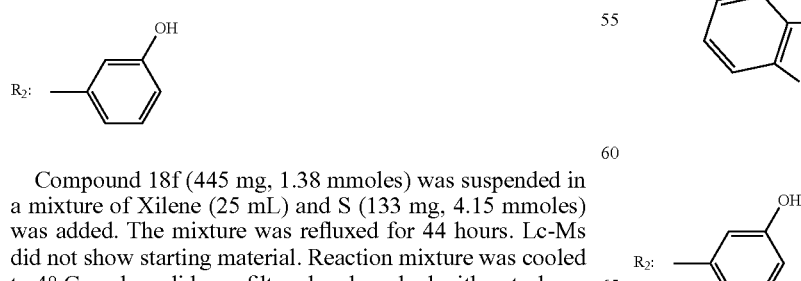

R₂:

Example 16

Process Synthesis of Compound 23a (JHG-1117-24)

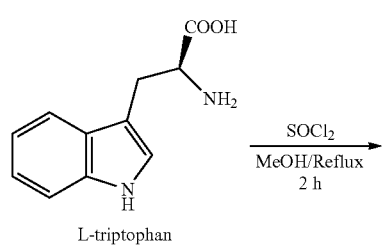

L-triptophan

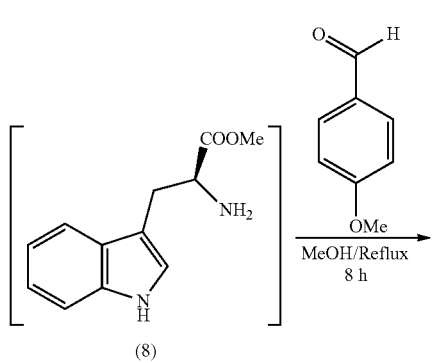

(2a) R₁: —N(morpholine)

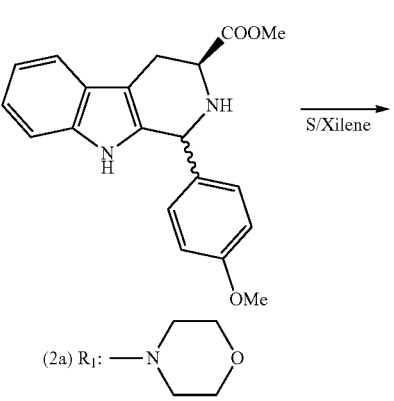

(3a) R₁: —N(morpholine)

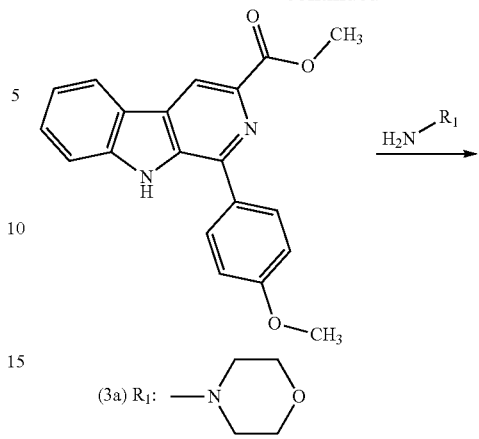

(3a) R₁: —N(morpholine)

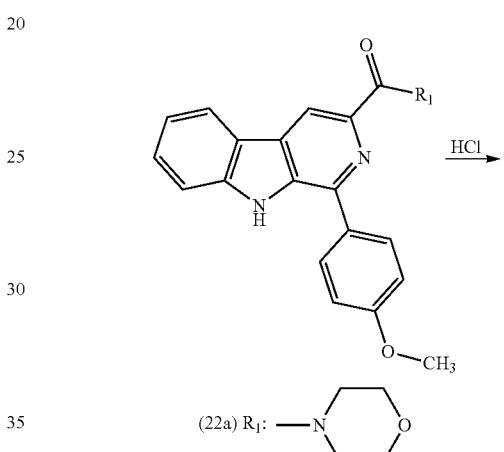

(22a) R₁: —N(morpholine)

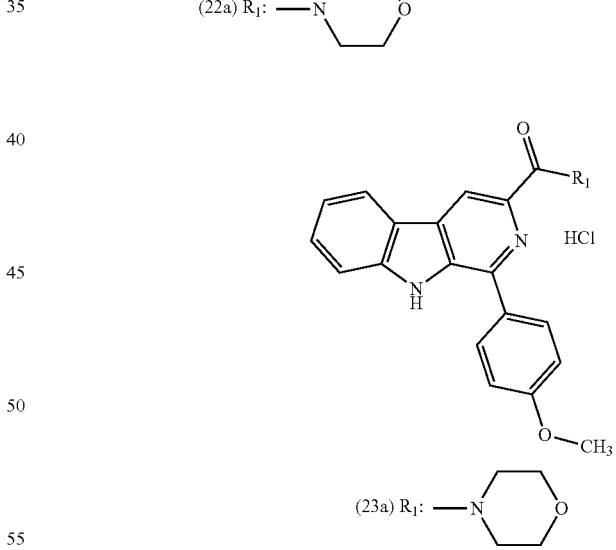

(23a) R₁: —N(morpholine)

L-Tryptophan (20 g, 0.098 mol) was suspended in methanol (100 mL). This suspension was cooled at 0° C. and SOCl2 (8.75 mL, 0.12 mol) was added dropwise. After, the reaction mixture was heated to reflux for 2.5 hours. During this time the starting material was completely dissolved and the solution was dark orange. After 2 hours an aliquot was concentrated to dryness and analyzed by HPLC-MS (99% of compound 6 (IQT-11-37)) and 1H-NMR checking that the starting material was disappeared.

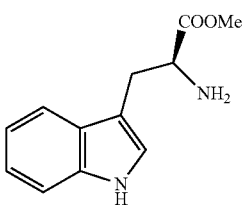

(8)

p-Anisaldehyde (32.5 mL, 0.28 mol) was added over the solution previously prepared, and this mixture was refluxed for 15 hours. After this time the reaction was checked by HPLC-MS. The starting material was disappeared. The reaction mixture was concentrated to dryness. The residue was dissolved in H2O (250 mL) and neutralized till pH-7 with NaHCO3 sat. (≈100 mL). This solution was extracted with Ethyl Acetate (3×400 ml). The organic layer was washed with $H_2O$ (2×400 ml) and NaCl sat. (2×200 mL). The organic layer was dried over $Na_2SO_4$, filtered and concentrated to dryness to obtain 30 g of compound 2a (IQT-11-37) (Yield: 91%) of a crude (HPLC-MS (purity): 94% mixture of two diastereoisomers. This crude was used in the next step with no further purification.

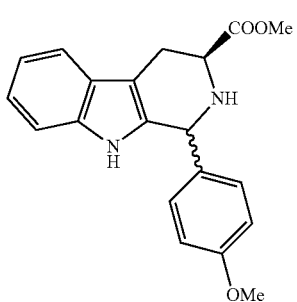

(2a)

Compound 2 (29.22 g, 0.087 mol) was suspended in a mixture of xylene (1080 mL) and S (13.9 g, 0.43 mol) was added. The mixture was refluxed for 22 hours. TLC and LC-MS: No SM was observed. After this time the reaction was cooled at 3° C. and kept with stirring overnight. Brown solid was filtered and washed with petroleum ether. Checking by HPLC-MS (94% 3a and 3% Xylene) and 1H-NMR showed no pure compound 3a. Brown solid (21.5 g) was purified by flash chromatography in silicagel (DCM-→DCM-AcOEt 9:1) to obtain pure compound 3a (IQT-11-37) (15.1 g; Yield: 52%)

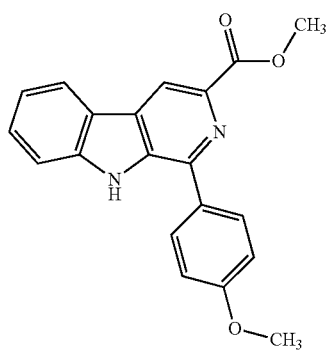

(3a)

To a suspension of compound 3a (400 mg, 1.20 mmol) in EtOH (4 ml) at room temperature, morpholine (0.5 ml; 6 mmol) was added. Starting material was solved and the mixture was heated to reflux. After 43 h, LC-MS showed no SM (42% of compound 22a). Mixture was cooled to room temperature and water (15 ml) was added. Mixture was stirred for 30 minutes and filtered. Cream colour solid obtained (260 mg) was purified by column chromatography in silicagel (Hexane: AcOEt 1:1) to afford pure compound 22a (JHG-1117-11-CF1) (140 mg; LC-MS: 100%; Yield: 30%).

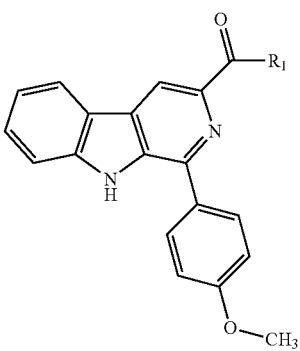

(22a)

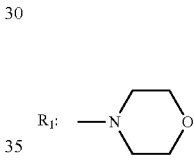

Compound 22a (136 mg; 0.340 mmol) was treated with a 1.25M solution of HCl (g) in EtOH (13.6 ml; 17.0 mmol) and stirred overnight. The pale yellow solid precipitated was filtered and washed with cold EtOH to obtain pure compound 23a (JHG-1117-24) (130 mg; LC-MS: 99%; Yield: 83%). 118 mg were delivered in two batches.

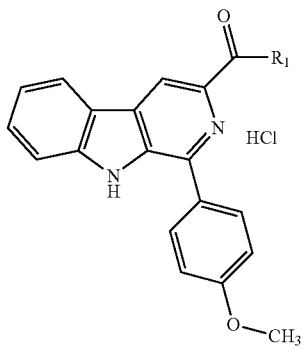

(23a)

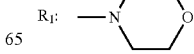

Example 17

Process Synthesis of Compound 23b
(JHG-1117-26)

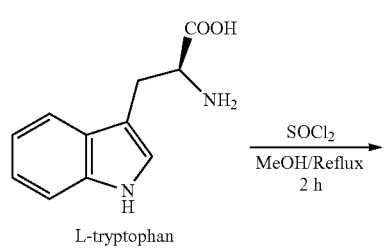
L-tryptophan

SOCl₂
MeOH/Reflux
2 h

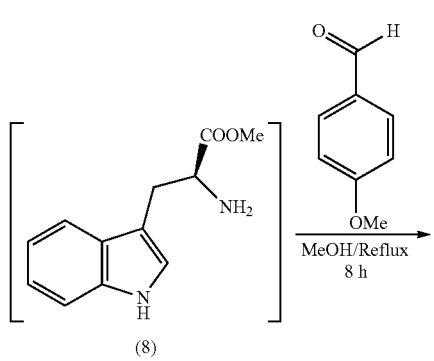
(8)

MeOH/Reflux
8 h

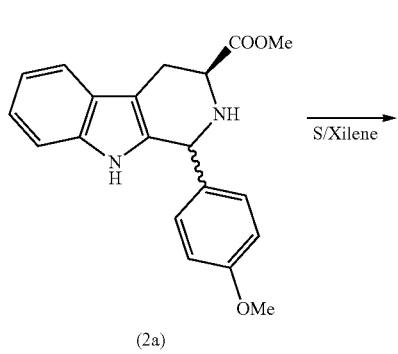
(2a)

S/Xilene

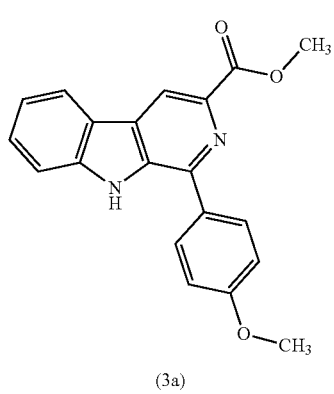
(3a)

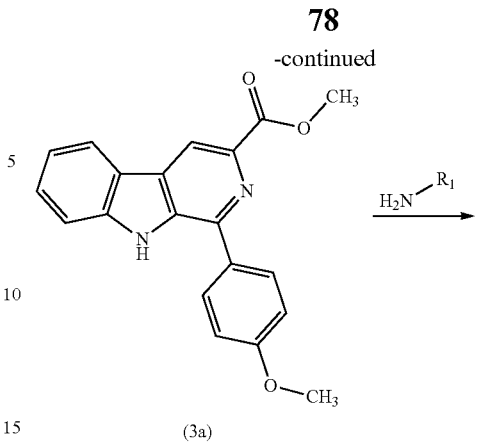
(3a)

H₂N—R₁

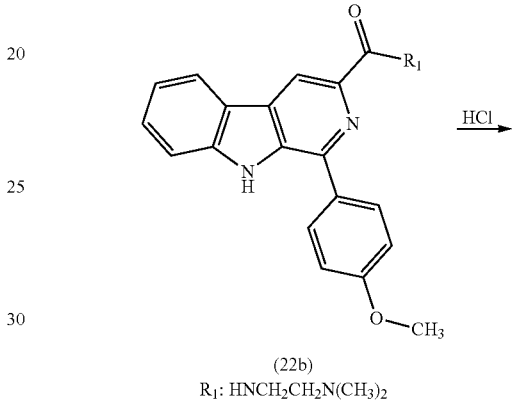
(22b)
R₁: HNCH₂CH₂N(CH₃)₂

HCl

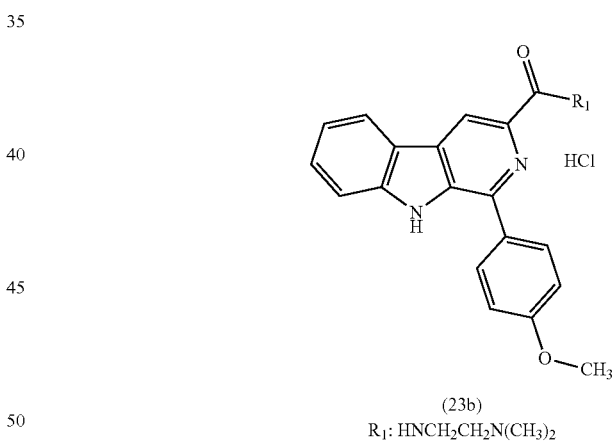
(23b)
R₁: HNCH₂CH₂N(CH₃)₂

Compound 3a (0.60 g, 1.80 mmol) (see Example 16) was solved and stirred in N,N-dimethylethylenediamine (8.2 mL, 75.1 mmol) at room temperature overnight. TLC after 15 hours showed starting material remaining. Mixture was heated at 50° C. and after additional 4 hours the reaction was completed. The mixture was concentrated to dryness to remove the excess of dimethylethylenediamine. Crude was triturated in water and filtered to obtain 490 mg of a brown solid that was purified by flash chromatography in silicagel (Acetone→Acetone: EtOH 9:1). Pure compound 22b (JHG-1117-5-CF1) was obtained as pale yellow solid (240 mg; LC-MS: 100%; Yield: 34%).

(22b)

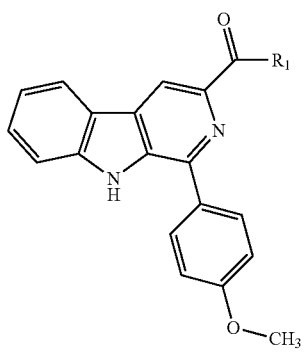

R₁: HNCH₂CH₂N(CH₃)₂

Compound 22b (240 mg; 0.618 mmol) was treated with a 1.25M solution of HCl (g) in EtOH (24.7 ml; 30.9 mmol). The orange solution formed was stirred at room temperature for 15 hours. Solvent was removed and the resulting reddish oil was triturated with iPrOH for 2 hours. Solid obtained was filtered and washed with MTBE to afford pure compound 23b (JHG-1117-26) (170 mg; LC-MS: 100%; Yield: 65%). 120 mg were delivered (two batches).

(23b)

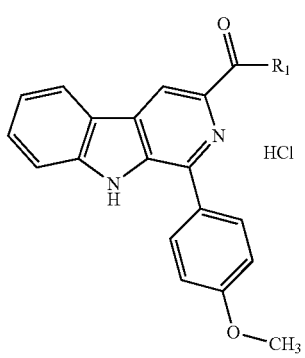

R₁: HNCH₂CH₂N(CH₃)₂

Example 18

Process Synthesis of Compound 23c (JHG-1117-28)

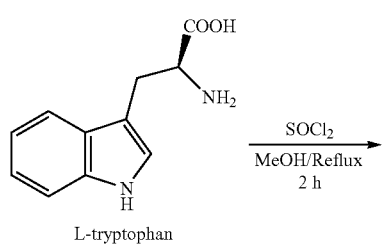

L-tryptophan

-continued

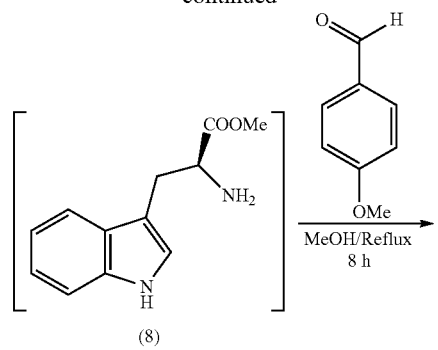

(8)

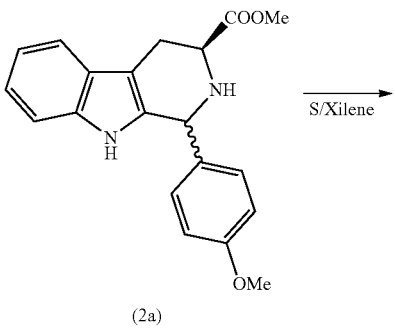

(2a)

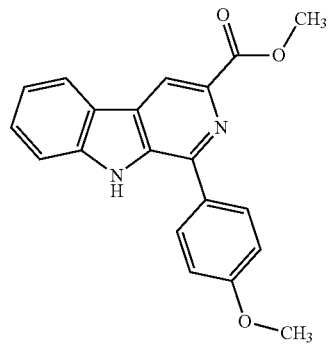

(3a)

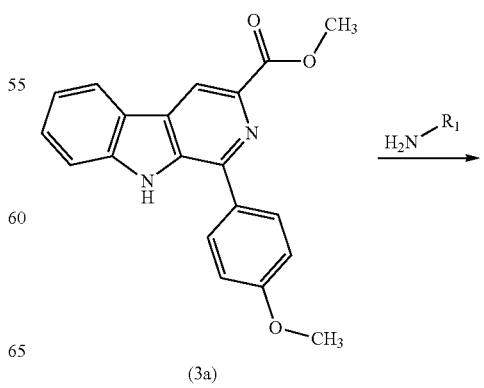

(3a)

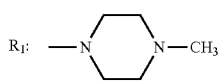

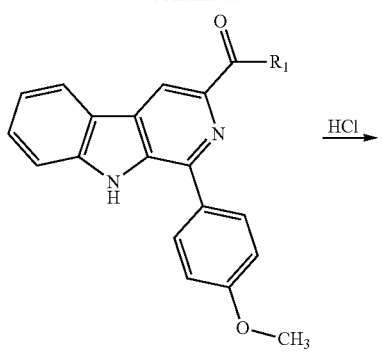

(22c) R₁: 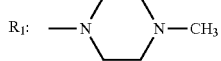

To a suspension of compound 3a (see Example 16) (400 mg, 1.20 mmol) in EtOH (4 ml) at room temperature, N-methylpiperazine (5.4 ml; 48.7 mmol) was added. Starting material was solved and the yellow solution was heated to reflux. After 137 h, LC-MS showed no SM (27% of compound 22c). Mixture was cooled to room temperature and concentrated to dryness. Resulting black oil was precipitated in water (10 ml) and clear brown solid obtained was filtered, washed with water and dried. This solid (330 mg; 49% of 22c by LC-MS) was purified by flash chromatography in silica gel (Acetone→Acetone: EtOH 10:1) to obtain pure compound 22c (JHG-1117-10-CF1) (147 mg; LC-MS: 96%; Yield: 30%).

(22c)

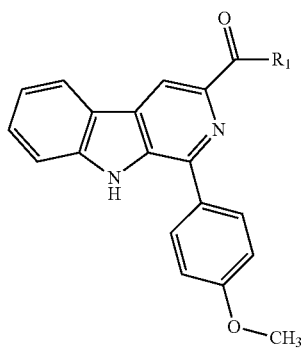

R₁: 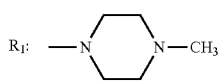

Compound 22c (136 mg; 0.340 mmol) was treated with a 1.25M solution of HCl (g) in EtOH (13.6 ml; 17.0 mmol) and stirred overnight. The pale yellow solid precipitated was filtered and washed with cold EtOH to obtain pure compound 23c (JHG-1117-28) (148 mg; LC-MS: 97%; Yield: 99%). 132 mg were delivered (two batches).

(23c)

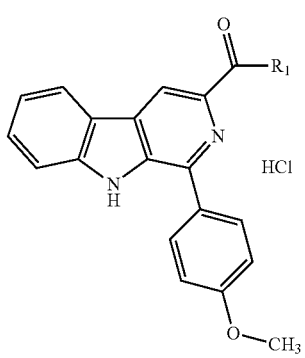

R₁: 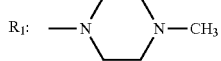

Example 19

Process Synthesis of Compound 23d (JHG-1117-41)

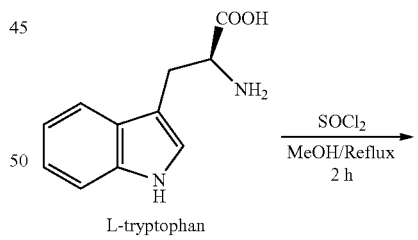

-continued

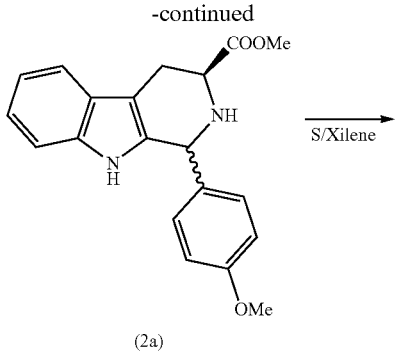
(2a)

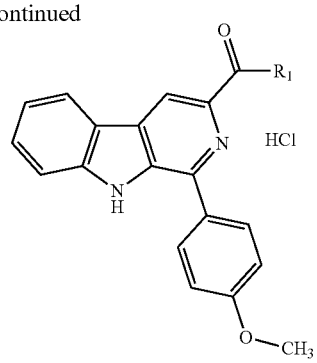
(23d) R₁: HNCH₂CH₂OH

A mixture of compound 3a (see Example 16) (0.50 g, 1.50 mmol) and 2-aminoethanol (2.7 ml, 45 mmol) was heated to 100° C. and stirred for 5 hours. TLC showed no starting material. Mixture was cooled to room temperature and water was added (20 ml). After 10 minutes, white solid precipitated was filtered and dried in vacuum to obtain compound 22d (JHG-1117-30S) (500 mg; LC-MS: 99%; Yield: 92%).

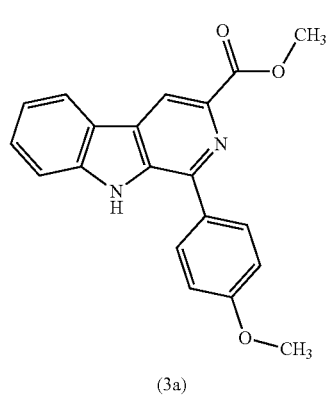
(3a)

(22d)

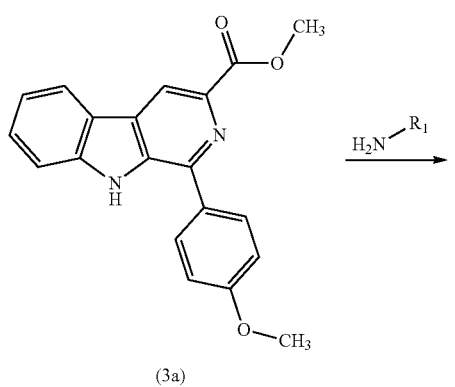
(3a)

R₁: HNCH₂CH₂OH

A suspension of the compound 22d (370 mg; 1.02 mmol) in a 1.25M solution of HCl (g) in EtOH (24.6 ml; 30.72 mmol) was stirred for 5 hours. After this time, the starting material was disappeared by TLC. Precipitated solid of compound 23d (JHG-1117-41) was filtered and dried in vacuum overnight (330 mg; LC-MS: 100%; Yield: 81%). 126 mg were delivered (two batches).

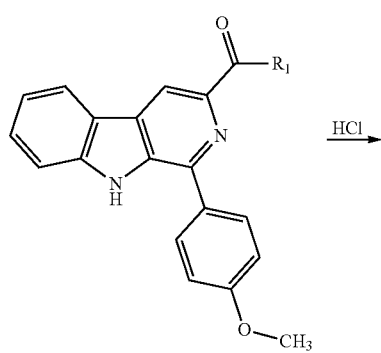
(22d) R₁: HNCH₂CH₂OH (23d)

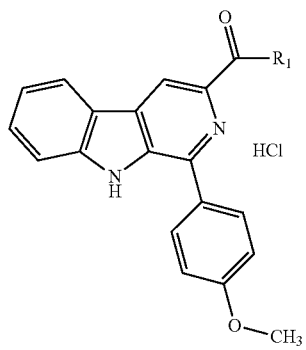
R₁: HNCH₂CH₂OH

Example 20

Process Synthesis of Compound 23e (JHG-1117-27S2)

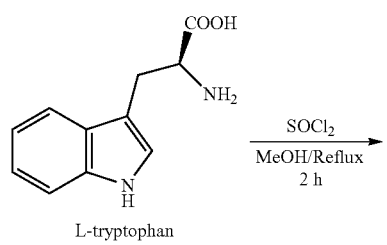

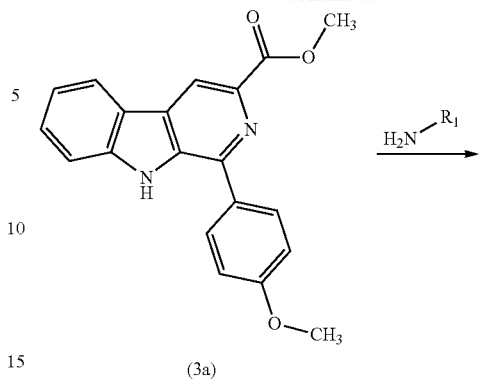

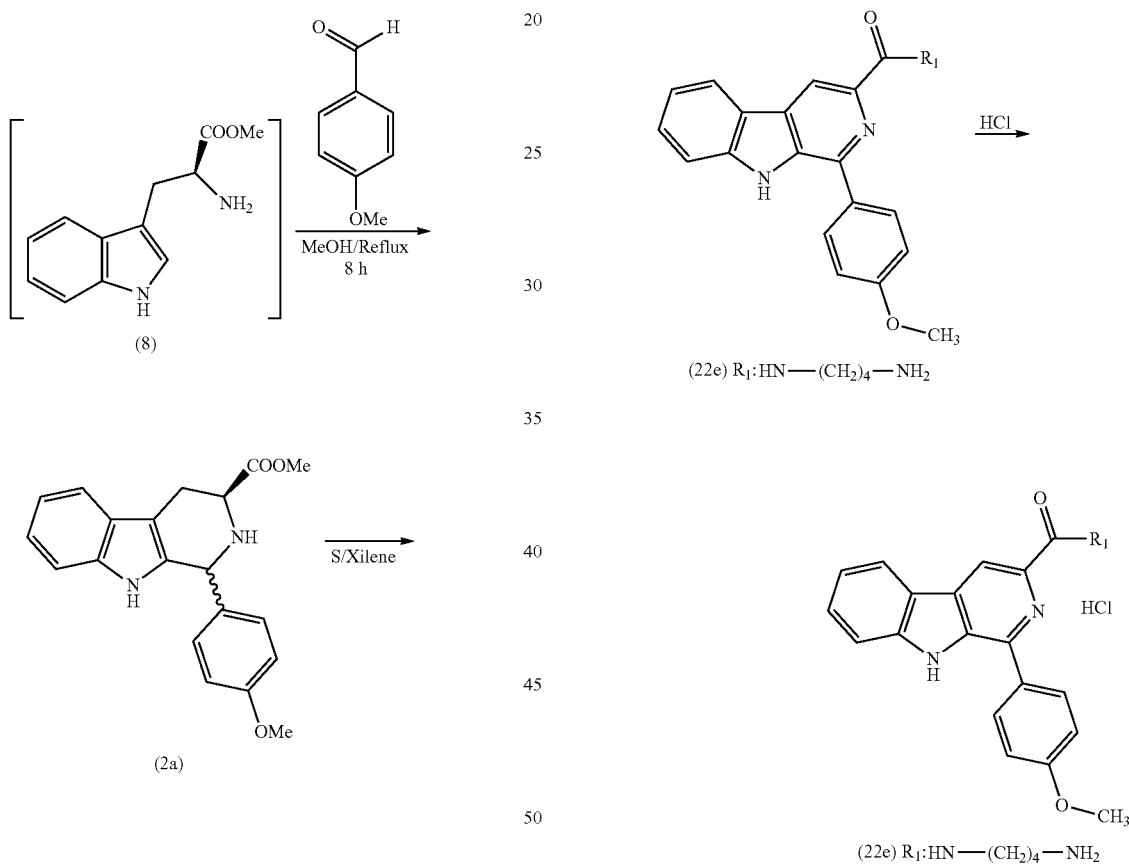

To a solution of compound 3a (see Example 16) (0.50 g, 1.50 mmol) in DCM (5 ml), 1,4-diaminobutane (2.65 g, 30 mmol) was added and the mixture stirred at room temperature overnight. TLC after 22 hours showed no starting material remaining. Water (15 ml) was added and the phases were separated. Organic layer was washed with water (8×30 ml) and brine, dried over sodium sulfate, filtered and concentrated to dryness. Yellow oil obtained (700 mg) was purified by column chromatography in silicagel ((Acetone→Acetone: EtOH 9:1) and after, treated with MTBE and concentrated to dryness (this treatment was repeated twice) affording the compound 22e (JHG-1117-8) as greenish solid (420 mg; LC-MS: 97%; Yield: 72%).

(22e)

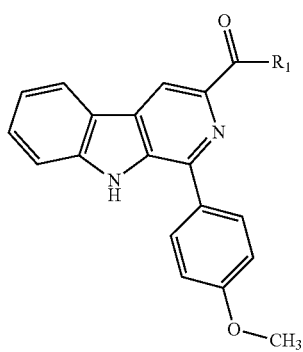

R₁: HN—(CH₂)₄—NH₂

Compound 22e (390 mg; 1.00 mmol) was solved in a 1.25M solution of HCl (g) in EtOH (35 ml; 43.7 mmol). Mixture was stirred at room temperature for 15 hours. Solvent was removed and the resulting reddish oil was triturated with iPrOH for 2 hours, filtered and washed with a mixture iPrOH-MTBE 1:1 to obtain a pale brown solid (LC-MS: 87% 23e). This solid was suspended in hot iPrOH (15 ml) and stirred 3 hours. Warm suspension was filtered and dried to obtain pure compound 23e (JHG-1117-27-S2) as beige solid (160 mg; LC-MS: 97%; Yield: 38%). 124 mg of compound 23e were delivered (two batches).

(23e)

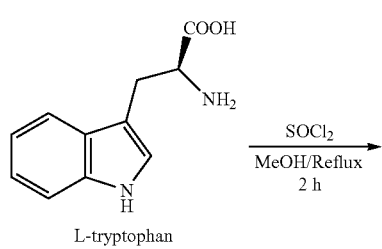

R₁: HN—(CH₂)₄—NH₂

Example 21

Process Synthesis of Compound 23f ((IFC-1201-09))

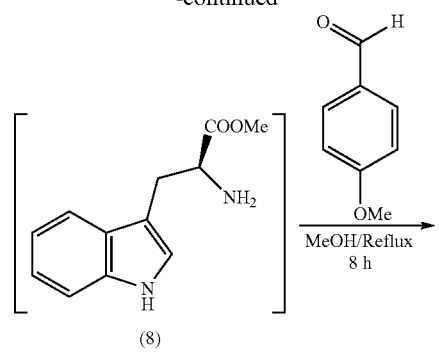

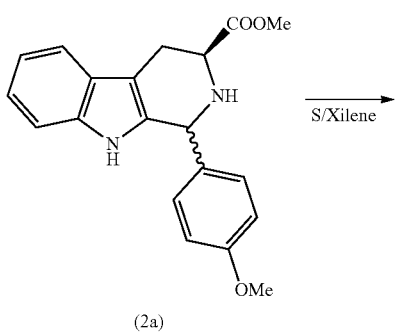

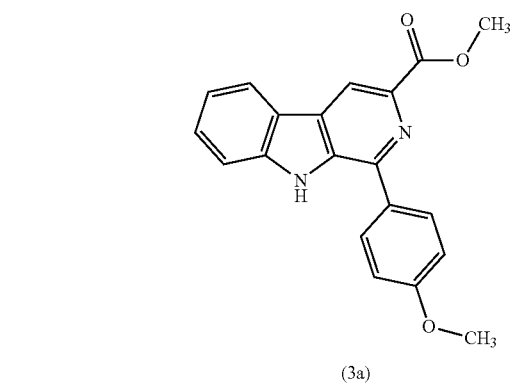

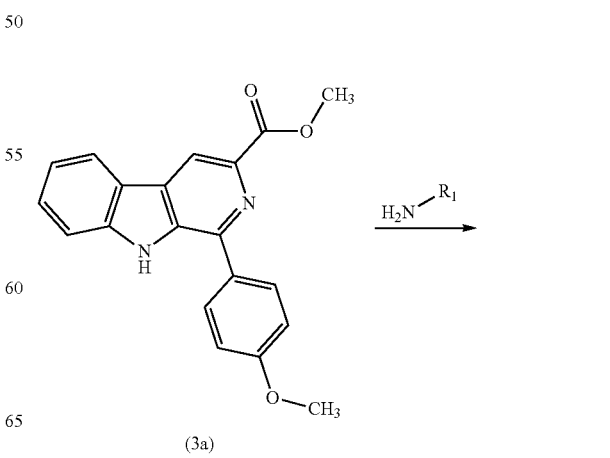

-continued

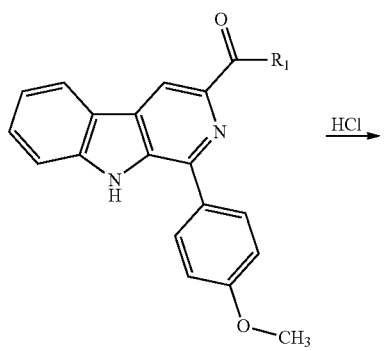

(22f) R₁: HNCH₂CH₂OCH₃

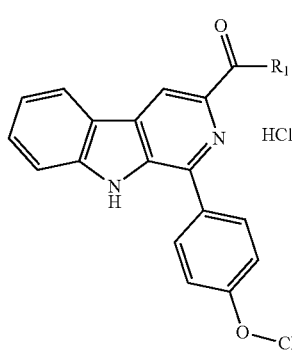

(23f) R₁: HNCH₂CH₂OCH₃

Compound 3a (obtained by the process disclosed in Example 16) (1.0 gg, 3.0 mmol) was dissolved in 2-methoxyethylamine (6.7 ml, 78 mmol) and the mixture was stirred at room temperature for 3 days. After this time a white solid was formed. This solid was filtered and washed with water and dried in oven at 45° C. 616 mg of compound 22f (IFC-1201-09 free base) were obtained (LC-MS: 98%; Yield: 55%). M.p.: 200-201° C.

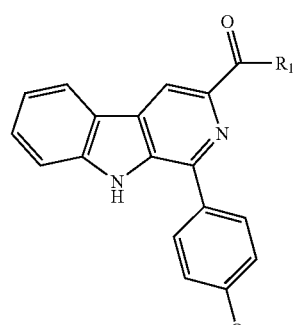

(22f)

R₁: HNCH₂CH₂OCH₃

Compound 22f (362 mg; 0.93 mmol) was solved in Ethanol (9 mL) and 1.25M solution of HCl (g) in EtOH (3.5 ml) was added. Mixture was stirred at room temperature for 4 hours. A yellow solid was formed, filtered and washed with EtOH to obtain 300.7 mg of a yellow solid (Yield: 75%, LC-MS: 87% 23f). (IFC-1201-09) were delivered (two batches). M.p.: 109-110° C.

(23f)

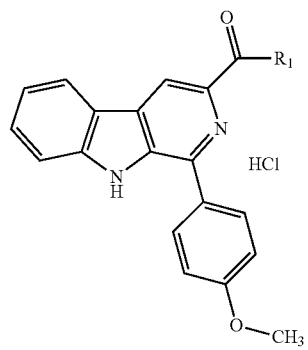

R₁: HNCH₂CH₂OCH₃

Example 22

Process Synthesis of Compound 26a
(JHG-1117-29)

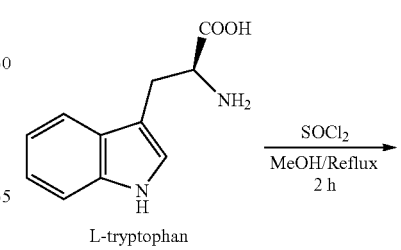

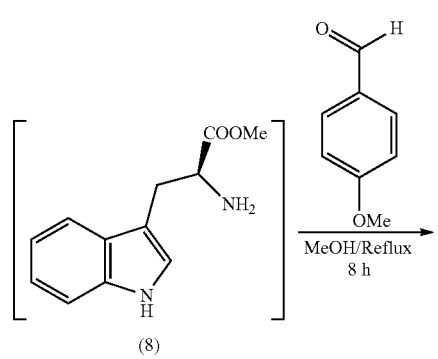

(8)

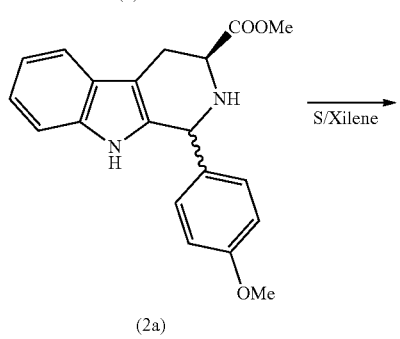

(2a)

-continued

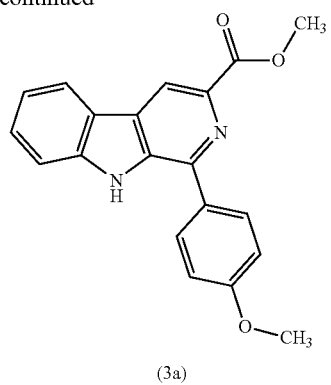

(3a)

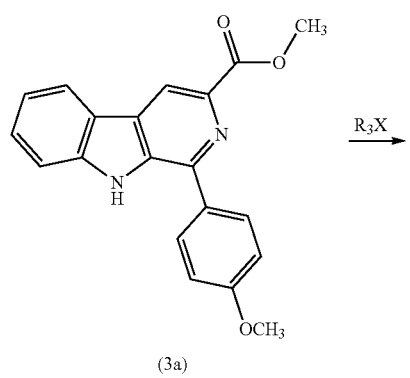

(3a)

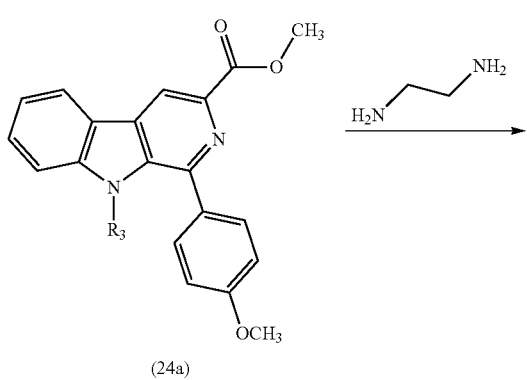

(24a)

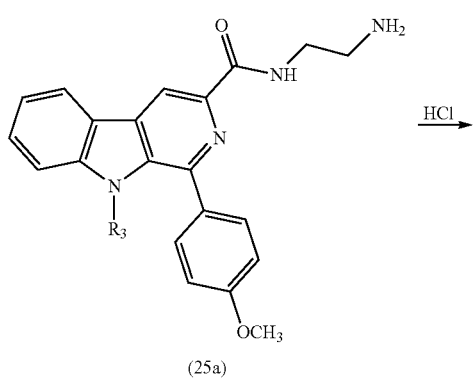

(25a)

-continued

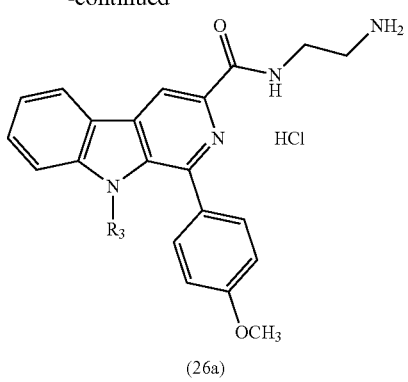

(26a)

To a solution of compound 3a (see Example 15) (300 mg, 0.9 mmol) in anhydrous DMF (5 ml), under N2 at room temperature, NaH 60% dispersion in mineral oil (55 mg, 1.35 mmol) was added (mixture turning to red solution). Mixture was stirred for 10 minutes and MeI (0.17 ml; 2.7 mmol) was dropwise added. Reaction mixture was stirred at this temperature overnight. LC-MS showed no starting material. Water (25 ml) and AcOEt (25 ml) were added and phases were separated. Organic layer was washed with H2O (2×) and brine, dried over sodium sulfate, filtered and concentrated to dryness. Resulting yellow oil (370 mg) was purified by flash chromatography in silica-gel (Hexmane-AcOEt 2:1→1:1) to afford compound 24a (JHG-1117-14-CF1) as pale yellow solid (260 mg; LC-MS: 100%; Yield: 84%.

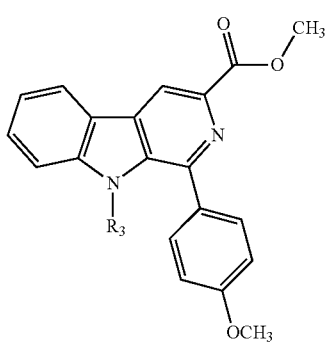

(24a)

R3: CH3

To a solution of compound 24a (0.50 g, 1.50 mmol) in DCM (3 ml), Ethylenediamine (2 ml; 30 mmol) was added and the mixture stirred at room temperature overnight. TLC after 15 hours showed no starting material remaining. Water (10 ml) was added and DCM was evaporated. Cream solid precipitated was filtered and washed several times with water (3×10 ml) in order to eliminate the excess of ethylenediamine. Pure compound 25a (JHG-1117-19-S): was obtained as beige solid (270 mg; LC-MS: 98%; Yield: 96%).

(25a)

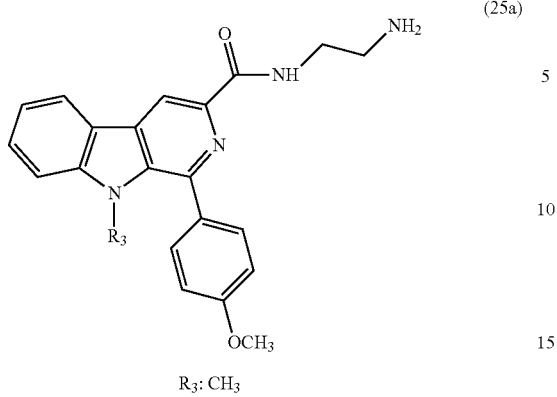

R₃: CH₃

Compound 25a (260 mg; 0.694 mmol) was treated, at room temperature, with a 1.25M solution of HCl (g) in EtOH (18 ml; 22.5 mmol) and the initial solution turning to suspension after 5 minutes of stirring. After 15 hours at this temperature, the mixture was filtered, washed with more cold EtOH and dried in vacuum overnight (285 mg; LC-MS: 98%; Yield: Quantitat). 132 mg of compound 26a (JHG-1117-29) were delivered (two batches).

(26a)

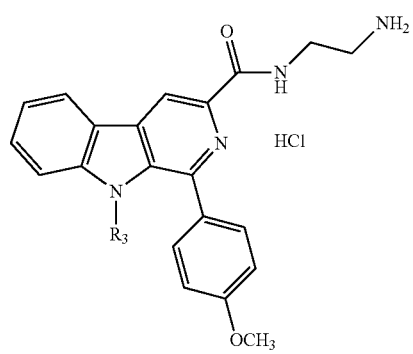

R₃: CH₃

Example 23

Process Synthesis of Compound 26b
(JHG-1117-43)

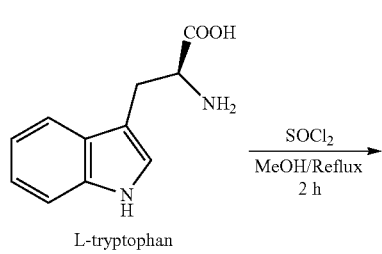

L-tryptophan $\xrightarrow{\text{SOCl}_2}{\text{MeOH/Reflux} \\ 2\text{ h}}$

-continued

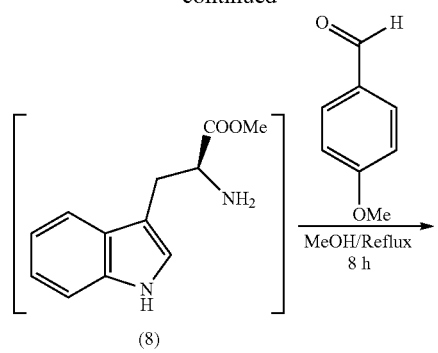

(8)

$\xrightarrow{\text{S/Xilene}}$ (2a)

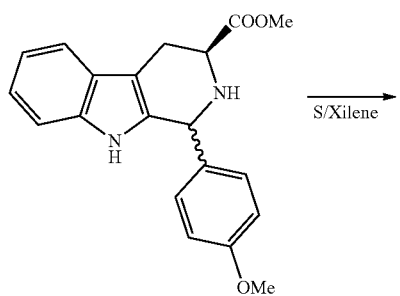

(3a)

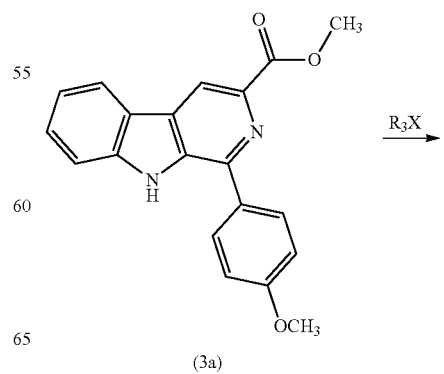

(3a)

$\xrightarrow{\text{R}_3\text{X}}$

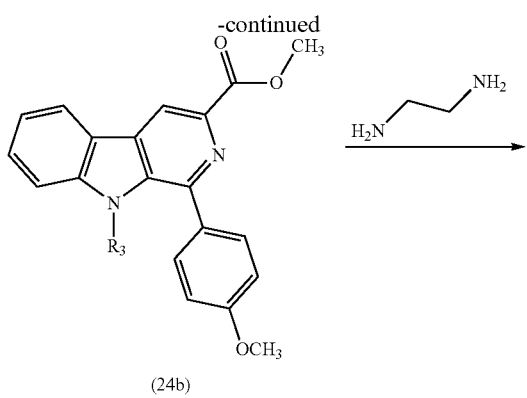

(24b)

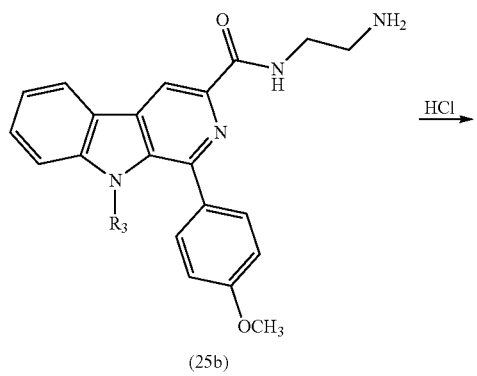

(25b)

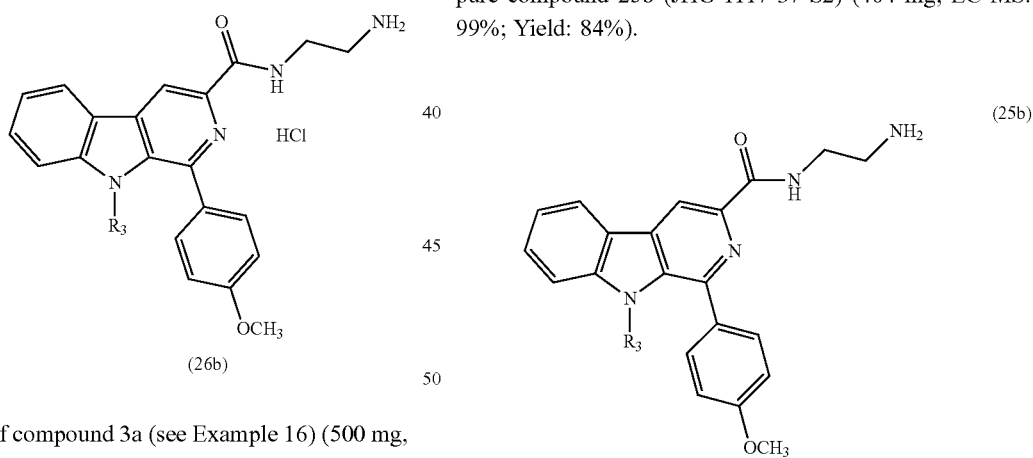

(26b)

To a solution of compound 3a (see Example 16) (500 mg, 1.5 mmol) in anhydrous DMF (10 ml), under N₂ at room temperature, NaH 60% dispersion in mineral oil (90 mg, 2.25 mmol) was added (mixture turning to red solution). Mixture was stirred for 10 minutes and Benzyl bromide (0.72 ml; 6.02 mmol) was dropwise added. Reaction mixture was stirred at this temperature for 4.5 hours. TLC showed no starting material. Water (50 ml) and AcOEt (20 ml) were added and phases were separated. Organic layer was washed with H₂O (3×), sat. NH₄Cl solution and brine, dried over sodium sulfate, filtered and concentrated to dryness. Resulting solid (1.5 g) was triturated with acetone to obtain white solid (210 mg; LC-MS: 99%; JHG-1117-31-S). Filtrate was concentrated (900 mg) and purified by flash chromatography in silica-gel (Hexane-AcOEt 4:1→3:1) to afford another white solid (280 mg; LC-MS: 100%; JHG-1117-31-CF1). Both solids were joined to obtain compound 24b (JHG-1117-31) 490 mg (Yield: 77%).

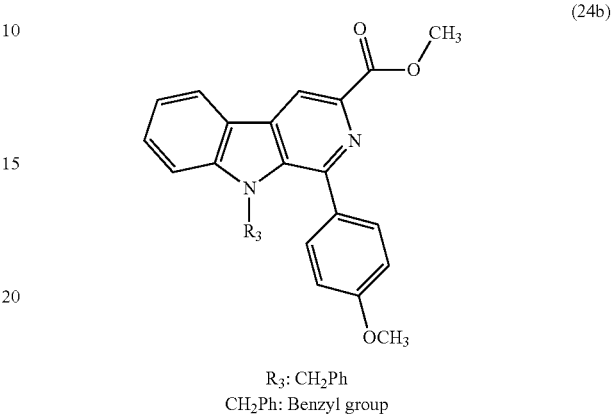

R₃: CH₂Ph
CH₂Ph: Benzyl group

To a solution of compound 24b (450 mg, 1.066 mmol) in DCM (7 ml), ethylenediamine (2 ml; 30 mmol) was added and the mixture stirred at room temperature overnight. TLC after 15 hours showed no starting material remaining. Water (15 ml) was added and DCM was evaporated. Orange solid suspended in water was triturated until a solid was formed. Filtration, washed with water and drying of this solid gave pure compound 25b (JHG-1117-37-S2) (404 mg; LC-MS: 99%; Yield: 84%).

Compound 25b (400 mg; 0.889 mmol) was treated, at room temperature, with a 1.25M solution of HCl (g) in EtOH (21.3 ml; 26.67 mmol) and the initial solution turning to suspension after 5 minutes of stirring. After 2 hours at this temperature, the mixture was filtered, washed with more cold EtOH and dried in vacuum overnight (230 mg; LC-MS: 100%; Yield: 53%). 127 mg (JHG-1117-43) were delivered (two batches).

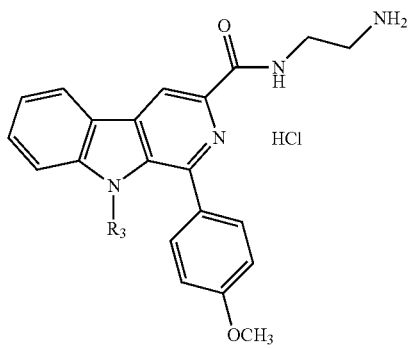

(26b)

R₃: CH₂Ph

Example 24

Alternative Process Synthesis of Compound 4a
(IFC-1102-48S)

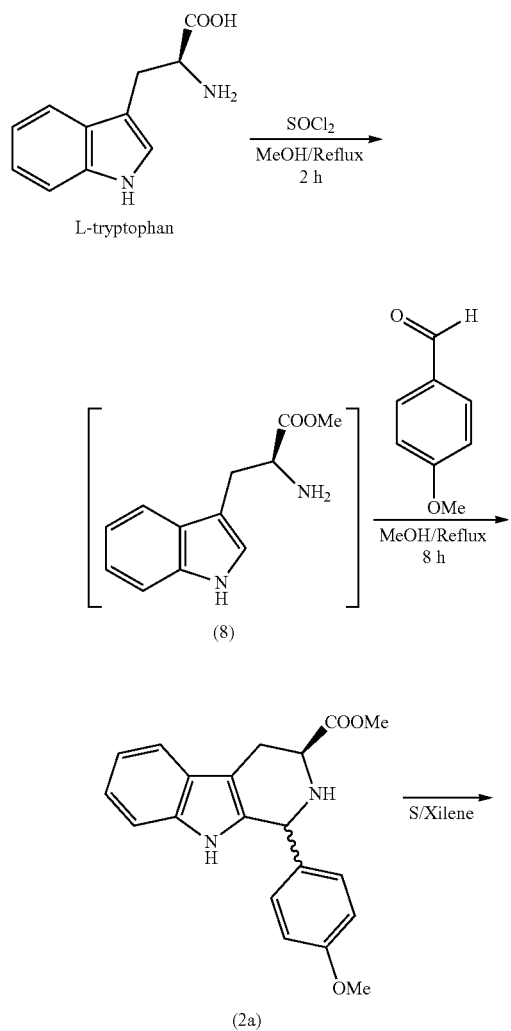

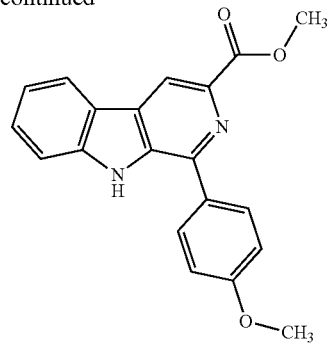

(3a)

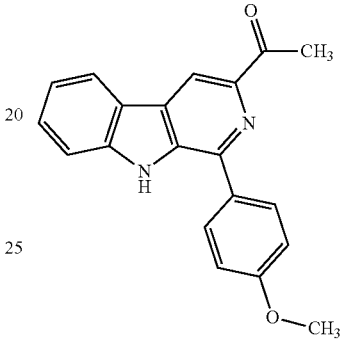

(3a)

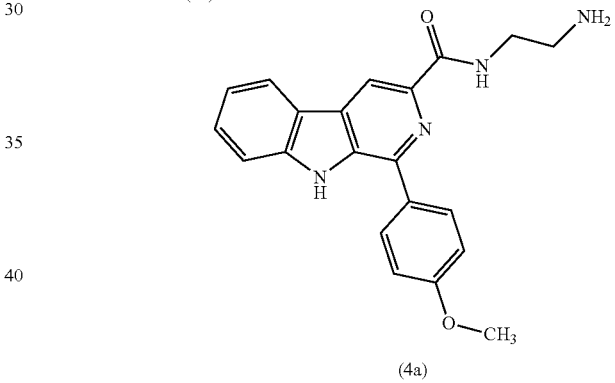

(4a)

To obtain the compound 8, L-Tryptophan (50 g, 0.24 mol) was suspended in methanol (100 mL). This suspension was cooled at 0° C. and SOCl₂ (21.5 mL, 0.29 mol) was added dropwise. After, the reaction mixture was heated to reflux for 2 hours. During this time the starting material was completely dissolved and the solution was dark. After 2 hours an aliquot was concentrated to dryness and analyzed by HPLC-MS and 1H-NMR checking that compound 6a was obtained and the starting material was disappeared.

To obtain the compound 2a, first anisaldehyde (32.5 mL, 0.28 mol) was added over the solution previously prepared, and this mixture was refluxed for 8 hours. After this time the reaction was checked by HPLC-MS. The starting material was disappeared. The reaction mixture was concentrated to dryness. The residue was dissolved in H₂O (500 mL) and was neutralized with NaHCO₃ sat. (≈320 mL). This solution was extracted with Ethyl Acetate (3×1 L). The organic layer was washed with H₂O (2×1 L) and NaCl sat. (2×500 mL). The organic layer was dried over Na₂SO₄, filtered and concentrated to dryness to obtain 82.9 g of a crude (HPLC-MS (purity): 76% mixture of two diastereoisomers). This crude was purified by flash chromatography in SiO$_2$ (eluents: hexane/EtOAc 3:1→EtOAc). In this case (it is no necessary) we separated the two diastereoisomers to analyze them. After, these were joined to prepare compound 3a. 54.88 g (yield: 67%) of the mixture of diastereoisomers were obtained with purity upper than 90%.

To obtain compound 3a, the previously obtained compound 2 (50.0 g, 0.148 mol) was suspended in a mixture of xilene (1800 mL) and S (23.68 g, 0.74 mol) was added. The mixture was refluxed for 22 hours. After this time the reaction was cooled at 4° C. and kept with agitation overnight. A light brown solid was obtained. This solid was washed with petroleum ether and checking by HPLC-MS and 1H-NMR. 39.11 g (yield: 79%) of compound 3a were obtained.

Finally, to obtained compound 4a, the previously obtained compound 3a (5.6 g, 0.017 mol) was suspended in ethylenediamine (51 mL, 0.73 mol) and this solution was stirred at room temperature overnight. The reaction was checking by TLC. The reaction mixture was concentrated to dryness to remove the excess of ethylenediamine. 7.4 g of compound 4a were obtained. This compound was recrystallized in methanol (90 mL) and was kept cold overnight. The solid obtained was filtered. Finally, 4.8 g (yield: 78%) of compound 4a (IFC-1102-48S) were obtained by the process disclosed herein with a purity of 98.6%.

To obtain the compound 4a hydrochloride (4a HCl), the compound 4a (0.1 g, 0.27 mmol) was treated, at room temperature, with a 1.25M solution of HCl (g) in EtOH (0.43 mL, 0.54 mmol) and the initial solution turning to suspension after 5 hours of stirring. A white solid (57 mg of compound 4a HCl) was formed. It was filtered and washed with cool EtOH. To confirm whether the compound 4a HCl obtained is mono or dihydrochloride as would be necessary to perform elemental analysis for example: HPCL, LC-MS, etc. The obtained compound is soluble in water. Structure confirmed by NMR.

Example 25

Alternative Process Synthesis of Compound 5a (IFC-1102-57S)

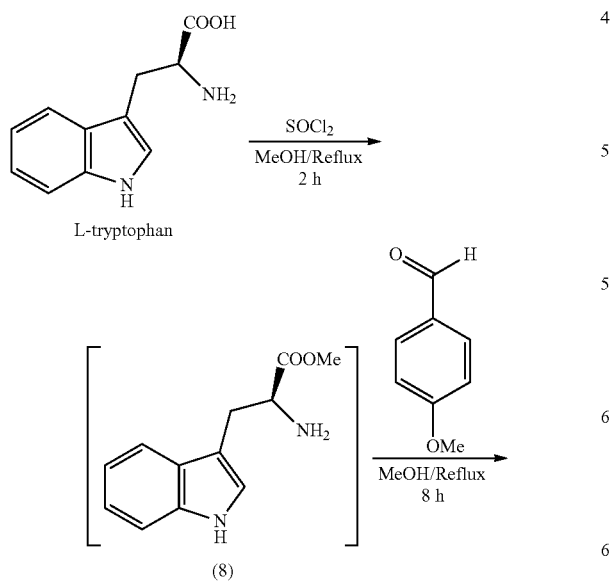

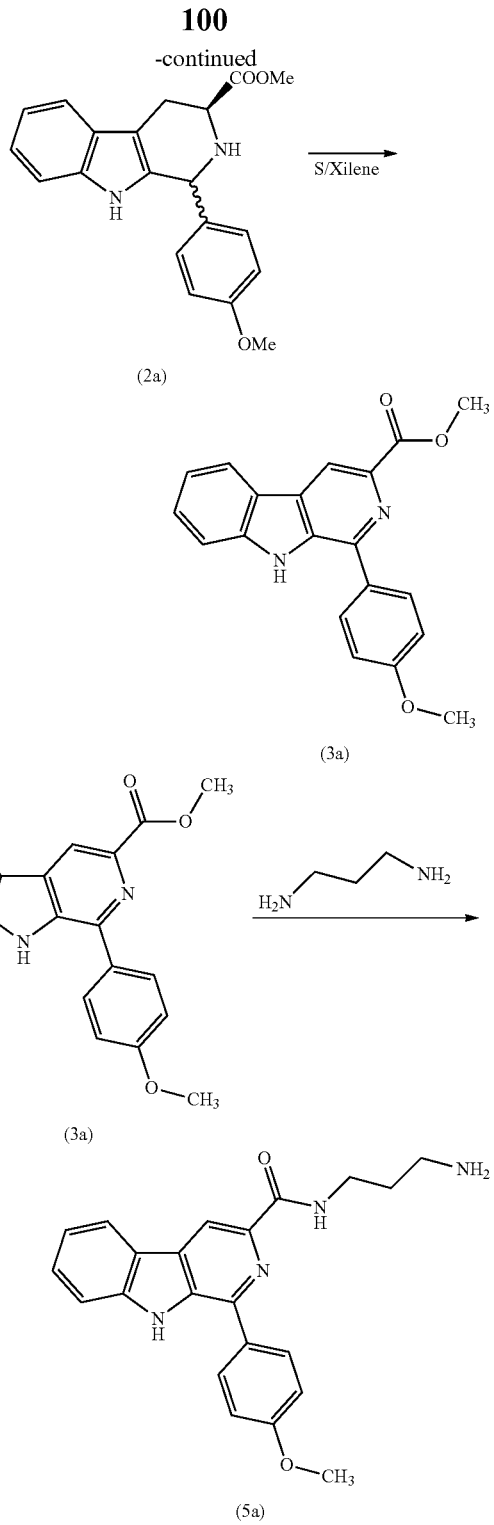

Compound 3a (6.0 g; 18 mmol) (obtained by the process disclosed in Example 24) was dissolved in 1,3-diaminepropane (60 mL; 40 eq.) and was stirred at room temperature overnight. After 16 hours, HPLC-MS showed total conversion. The excess of diamine was removed in the rotatory evaporator. A brown solid was obtained. This solid was triturated with acetone for 2 hours and then was filtered, obtained a white solid corresponding to the compound 5a (HPLC-MS (purity): 98%). 1H-NMR of this solid showed rests of diamine so it was necessary to wash with more water. The solid was filtered and dried in a vacuum oven at 40° C. The solid was washed again with acetone, filtered and dried. 5.42 g (yield: 80%) of compound 5a were obtained as a white solid (purity HPLC-MS: 99%).

Example 26

Alternative Process Synthesis of Compound 7a (PGP-11048SR1)

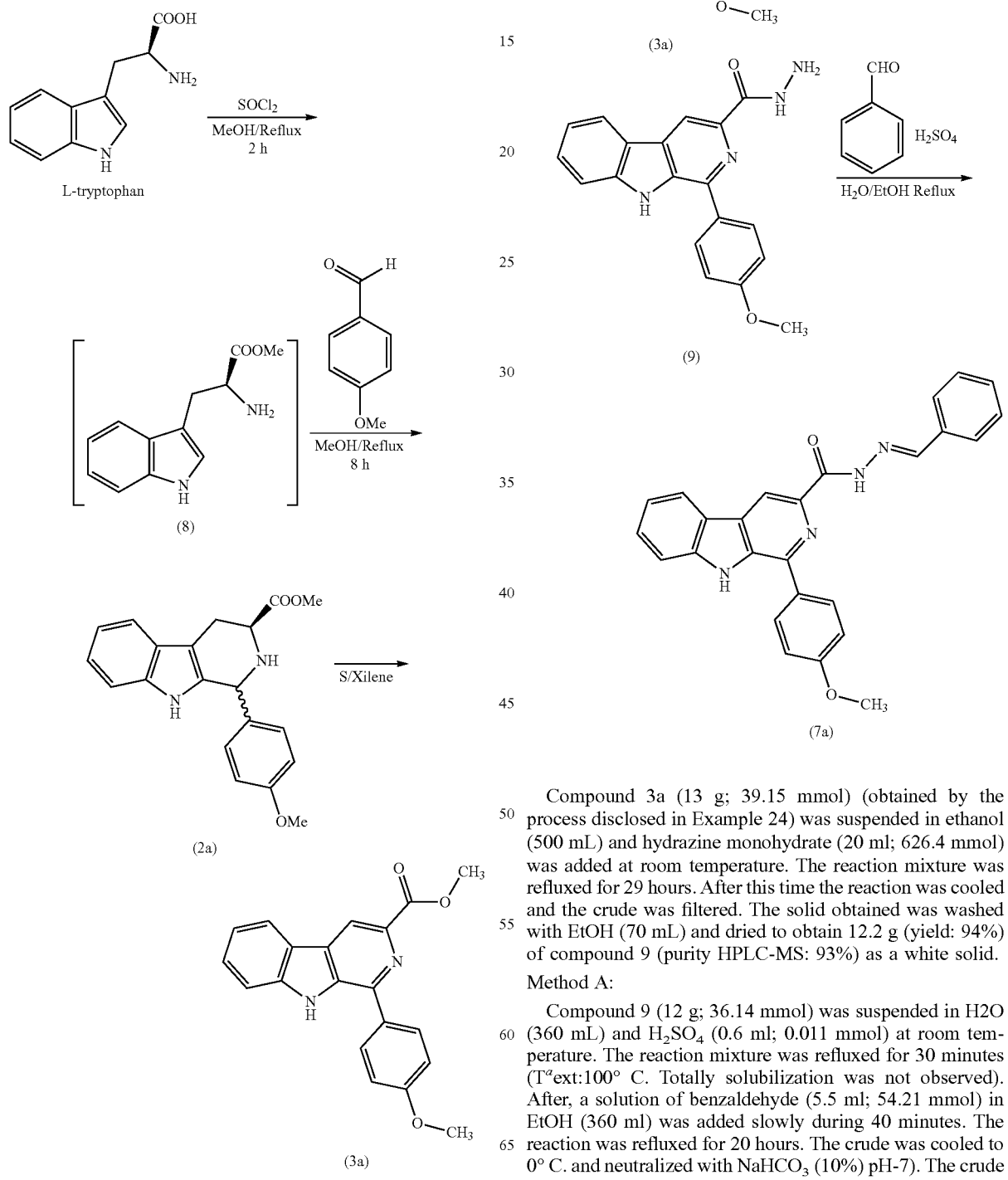

Compound 3a (13 g; 39.15 mmol) (obtained by the process disclosed in Example 24) was suspended in ethanol (500 mL) and hydrazine monohydrate (20 ml; 626.4 mmol) was added at room temperature. The reaction mixture was refluxed for 29 hours. After this time the reaction was cooled and the crude was filtered. The solid obtained was washed with EtOH (70 mL) and dried to obtain 12.2 g (yield: 94%) of compound 9 (purity HPLC-MS: 93%) as a white solid.

Method A:

Compound 9 (12 g; 36.14 mmol) was suspended in H2O (360 mL) and $H_2SO_4$ (0.6 ml; 0.011 mmol) at room temperature. The reaction mixture was refluxed for 30 minutes ($T^a$ext:100° C. Totally solubilization was not observed). After, a solution of benzaldehyde (5.5 ml; 54.21 mmol) in EtOH (360 ml) was added slowly during 40 minutes. The reaction was refluxed for 20 hours. The crude was cooled to 0° C. and neutralized with $NaHCO_3$ (10%) pH-7). The crude was filtered and dried. The solid obtained was recrystallized in MeOH (15.9 g in 1.85 L de MeOH) obtaining 10.5 g of compound 7a (purity HPLC-MS: 99%; Yield: 69%) as a white solid.

Method B:

Compound 9 (400 mg; 1.2 mmol) was suspended in EtOH (12 ml) and heated to reflux. Benzaldehyde (0.18 ml; 1.8 mmol) in EtOH (12 ml) was added slowly (when the addition was finished the solubilization was full). The reaction was refluxed for 18 hours. The crude was concentrated obtaining a solid (700 mg). This solid was recrystallized in MeOH (700 mg in 70 ml de MeOH) obtaining 418 mg of compound 7a (purity HPLC-MS:99%; Yield: 83%) as a white solid.

Example 27

Pre-clinical studies in experimental animals. Effect of 3-(carbohydrazyl-N'-phenylsubstituted)-1-benzosubstituted-β-carbolinic-3-carbohydrazide derivative (compound 7a or ANIS-BZ) in an oral glucose tolerance test performed in normoglycemic rats.

Male Wistar rats were utilized provided by Mato Grosso do Sul's Federal University's Bioterium. Until the experiments were carried out, the animals have had free access to feed and water. The room temperature was kept at 22±2° C. and the light/dark cycle was of 12 hours.

All procedures were submitted to the Animal Experimentation Ethics Committee.

The glucose tolerance test is a reference method for the diagnosis of diabetes or glucose intolerance (5).

Distinct rat groups were orally treated, once a day, with 3-(carbohydrazyl-N'-phenylsubstituted)-1-benzosubstituted-β-carbolinic-3-carbohydrazide (compound 7a or ANIS-BZ) at doses: 0.5, 1 or 5 mg/kg or vehicle (control) for 3 days. Similarly, another rat group received metformin (reference drug used for lowering glucose serum levels) in a 300 mg/kg dose, orally, once a day for 3 days. The oral glucose tolerance test was carried out by administering of a glucose solution (2 g/kg body mass). Glycemia was determined at zero time (before oral administering) and at 60 minutes after the glucose overload.

FIG. 1A shows that on the first day, the oral treatment with 3-(carbohydrazyl-N'-phenylsubstituted)-1-benzosubstituted-β-carbolinic-3-carbohydrazide (compound 7a or ANIS-BZ) in a 5 mg/kg dose, reduces the glycemic levels of animals that received an oral glucose overload when compared to the control group. Similarly, the oral treatment with metformin induces reduction of glycemic levels, but a doses 60 times fold higher.

FIG. 1B shows that after 3 days, the oral treatment with 3-(carbohydrazyl-N'-phenylsubstituted)-1-benzosubstituted-β-carbolinic-3-carbohydrazide (compound 7a or ANIS-BZ), at 5 mg/kg dose, reduces the glycemic levels of animals that received oral glucose overload when compared to the control group. Similarly, the oral treatment with metformin induces glycemic levels reduction but a doses 60 times fold higher.

FIG. 2 shows that after 3 days of oral treatment with 3-(carbohydrazil-N'-phenylsubstituted)-1-benzosubstituted-β-carbolinic-3-carbohydrazide (compound 7a or ANIS-BZ), only the 1 and 5 mg/kg doses reduced statistically significant the glycemic levels of animals that received oral glucose overload when compared to the control group. Similarly, the oral treatment with metformin induces reduction of glycemic levels, but a doses 60 times fold higher.

Example 28

Pre-clinical studies in experimental animals. Effect of N(-ethylamine)-1-benzosubstituted-β-carboline-3-carboxamide (compound 4a or ANIS-NH2) in an oral glucose tolerance test performed in normoglycemic rats.

Distinct groups of rats were treated orally, once a day, with N(-ethylamine)-1-benzosubstituted-β-carboline-3-carboxamide (compound 4a or ANIS-NH2) at doses: 0.5, 1 or 5 mg/kg, or vehicle for 3 days. Similarly, another group of rats received metformin in a 300 mg/kg dose orally for 3 days once a day. The oral glucose tolerance test was done under the administration of a glucose solution (2 g/kg body mass). Glycemia will be determined at the zero (before oral administration) time and 60 minutes after glucose overload.

FIG. 3A shows that on the first day, the oral treatment with N(-ethylamine)-1-benzosubstituted-β-carboline-3-carboxamide (compound 4a or ANIS-NH2) in a 5 mg/kg dose, reduces the glycemic levels of animals that received an oral glucose overload when compared to the control group. Similarly, the oral treatment with metformin induces reduction of glycemic levels, but a doses 60 times fold higher.

FIG. 3B shows that after 3 days, the oral treatment with N(-ethylamine)-1-benzosubstituted-β-carboline-3-carboxamide (compound 4a or ANIS-NH2), at 5 mg/kg dose, reduces the glycemic levels of animals that received oral glucose overload when compared to the control group. Similarly, the oral treatment with metformin induces glycemic levels reduction but a doses 60 times fold higher.

FIG. 4 shows that after 3 days of oral treatment with N(-ethylamine)-1-benzosubstituted-β-carboline-3-carboxamide (compound 4a or ANIS-NH2), only the 1 and 5 mg/kg doses reduced statistically significant the glycemic levels of animals that received oral glucose overload when compared to the control group. Similarly, the oral treatment with metformin induces reduction of glycemic levels, but a doses 60 times fold higher.

Example 29

Pre-clinical studies in experimental animals. Effect of compounds 4a (IFC-1102-48S), 5a (IFC-1102-57S) and 7a (PGP-11048SR1) on systolic blood pressure test performed in SHR hypertensive rats.

Male Spontaneously Hypertensive Rats (SHR) were provided by Charles River Laboratories (USA). Until the experiments were carried out, the animals have had free access to feed and water. The room temperature was kept at 22±2° C. and the light/dark cycle was of 12 hours. All procedures were submitted to the Animal Experimentation Ethics Committee.

Distinct rat groups were orally treated, once a day, with 5 mg/kg of compounds 4a or 5a or 6a during the first 4 days, 10 mg/kg during the next 4 days and 15 mg/kg until the end of the treatment period or vehicle (control) for the same days. Similarly, another rat group received metformin (MET) (reference drug used for lowering glucose serum levels) in a 300 mg/kg dose, orally, from day 1 to the end of the treatment. Plasma cholesterol levels were measured in triplicate 12 hours after drug administration by the cholesterol oxidase/peroxidase method (BioSystems S.A, Barcelona, Spain). Blood samples were obtained by femoral vein punction. This method was chosen because of its noninvasive character, enabling daily measurements with the same rats throughout the entire treatment.

Compounds 4a, 5a and in a less degree compound 7a, disclosed in the present invention, shows in SHR rats an inhibitory effect on systolic blood pressure at different times and doses of treatment. This effect at 5-15 mg/kg is greater than that of metformin at 300 mg/kg. Rats treated with compound 4a ($p<0.001$), 5a ($p<0.001$) and 7a ($p<0.05$)

decreased the systolic blood pressure between 5-7%, compared to the vehicle-control group, statistically significant.

Example 30

Pre-clinical studies in experimental animals. Effect of compounds 4a (IFC-1102-48S), 5a (IFC-1102-57S) and 7a (PGP-11048SR1) on plasma cholesterol levels test performed in SHR hypertensive rats.

Male SHR were provided by Charles River Laboratories (USA). Until the experiments were carried out, the animals have had free access to feed and water. The room temperature was kept at 22±2° C. and the light/dark cycle was of 12 hours. All procedures were submitted to the Animal Experimentation Ethics Committee.

Distinct rat groups were orally treated, once a day, with 5 mg/kg of compounds 4a or 5a or 6a during the first 4 days, 10 mg/kg during the next 4 days and 15 mg/kg until the end of the treatment period or vehicle (control) for the same days. Similarly, another rat group received metformin (reference drug used for lowering glucose serum levels) in a 300 mg/kg dose, orally, from day 1 to the end of the treatment. Blood pressure was measured in triplicate 4 hours after drug administration in warmed warmed, restrained, conscious rats by the tail-cuff method with a computerized oscillometric system recorder (Nyprem, Cibertec). This method was chosen because of its noninvasive character, enabling daily measurements with the same rats throughout the entire treatment.

Compounds 4a, 5a and 7a, disclosed in the present invention shows, in SHR rats, inhibition of plasma cholesterol levels at 25 days of treatment (15 mg/Kg) similar to Metformin (300 mg/Kg) (FIG. 5), although the latter did the effect at much higher concentration (20 times fold higher). This result indicates that said compounds are candidates to become medicaments to treat hypercholesterolemia or metabolic syndrome. The effect on plasma cholesterol levels was more pronounced for compounds 5a and 7a (FIG. 5).

Example 31

Pre-clinical studies in experimental animals. Effect of compound 4a (IFC-1102-48S) on plasma triglyceride levels test performed in SHR hypertensive rats.

Male SHR were provided by Charles River Laboratories (USA). Until the experiments were carried out, the animals have had free access to feed and water. The room temperature was kept at 22±2° C. and the light/dark cycle was of 12 hours. All procedures were submitted to the Animal Experimentation Ethics Committee.

Distinct rat groups were orally treated, once a day, with 5 mg/kg of compound 4a during the first 4 days, 10 mg/kg during the next 4 days and 15 mg/kg until the end of the treatment period or vehicle (control) for the same days. Similarly, another rat group received metformin (reference drug used for lowering glucose serum levels) in a 300 mg/kg dose, orally, from day 1 to the end of the treatment. Plasma triglyceride levels were measured in triplicate 12 hours after drug administration by the glycerol phosphate oxidase/peroxidase method (BioSystems S.A, Barcelona, Spain). Blood samples were obtained by femoral vein punction. This method was chosen because of its noninvasive character, enabling daily measurements with the same rats throughout the entire treatment.

As shown in FIG. 6, Compound 4a disclosed in the present invention shows, in SHR rats a statistically significant ($p<0.05$), inhibition of plasma triglyceride levels at 25 days of treatment (5-15 mg/Kg).

Example 32

Pre-clinical studies in experimental animals. Effect of compound 5a (IFC-1102-57S) on body weight in SHR hypertensive rats.

Male SHR were provided by Charles River Laboratories (USA). Until the experiments were carried out, the animals have had free access to feed and water. The room temperature was kept at 22±2° C. and the light/dark cycle was of 12 hours. All procedures were submitted to the Animal Experimentation Ethics Committee.

Distinct rat groups were orally treated, once a day, with 5 mg/kg of compound 5a during the first 4 days, 10 mg/kg during the next 4 days and 15 mg/kg until the end of the treatment period or vehicle (control) for the same days. Similarly, another rat group received metformin (reference drug used for lowering glucose serum levels) in a 300 mg/kg dose, orally, from day 1 to the end of the treatment. Rats were weighted in a CHYO MK2000B precision weight chamber.

Compound 5a showed a statistically significant effect in lowering SHR body weight compared to control untreated rats ($p<0.05$).

Example 33

Pre-clinical studies in experimental animals. Effect of compound 4a (IFC-1102-48S) on blood glucose levels test performed in SHR hypertensive rats.

Male SHR were provided by Charles River Laboratories (USA). Until the experiments were carried out, the animals have had free access to feed and water. The food was removed 12 h before glucose determination. The room temperature was kept at 22±2° C. and the light/dark cycle was of 12 hours. All procedures were submitted to the Animal Experimentation Ethics Committee.

Distinct rat groups were orally treated, once a day, with 5 mg/kg of compound 4a during the first 4 days, 10 mg/kg during the next 4 days and 15 mg/kg until the end of the treatment period or vehicle (control) for the same days. Similarly, another rat group received metformin in a 300 mg/kg dose, orally, from day 1 to the end of the treatment. Blood glucose levels were measured in triplicate 12 hours after drug administration with the aid of a GLUCOCARD TM G meter, GT-1810. Results were compared with the effect of metformin at the same dosis as the compounds. Blood samples were obtained by femoral vein punction. This method was chosen because of its noninvasive character, enabling daily measurements with the same rats throughout the entire treatment.

Compound 4a showed statistically significant ($p<0.01$) blood glucose decrease in the range of doses from 5 to 15 mg/kg after treatment periods of 4-15 days between 5-7%, compared to the vehicle-control group. Metformin (300 mg/kg for 23 days) had a slightly greater effect on blood glucose levels, although the dose was much greater than that of the test compounds. Although SHR is not the best model to study glycemia, the results obtained were similar to those previously obtained in other animal model of diabetes, and suggest that the test compounds disclosed herein have a positive effect to regulate blood sugar levels.

Example 34

Toxicology Study of Compounds 4a (IFC-1102-48S), 5a (IFC-1102-57S) and 7a (PGP-11048SR1) in a *Drosophila melanogaster* (Oregon-R Strain) Model The purpose of this study was to test and compare the potential toxic effects of compounds 5a, 6a and 7a on the larva-to-adult viability and development time in a *Drosophila melanogaster* (Oregon-R) flies. These studies have a relevant predictive role with the aim to anticipate possible adverse toxicological effects that may happen during preclinical studies with animal, preferably mammals. In addition, the data provided are highly quantitative.

The study procedures were checked and approved by the animal welfare guidelines of the European Union and the Institutional Committee for Animal Research of the University of the Balearic Islands (Spain).

*Drosophila melanogaster* (Oregon-R) flies were obtained by the University of the Balearic Islands (Spain). The larvae had access to food ad libitum during treatment. The larvae were seeded on standard food supplemented with the appropriate dose of compounds tested. Each compound was tested at 1, 10, 100, 1000 and 2000 µg/ml dissolved in standard food.

*Drosophila melanogaster* (Oregon-R strain) flies were maintained by serial transfers in 150 ml bottles containing 30 ml of yeast medium (water, agar, salt, sugar, and inactive yeast), complemented with a fungicide (methyl-4-hydroxybenzoate), antibacterial (propionic acid) and active yeast powder on the surface, at 25° C. and 65% humidity with day-night cycles. Fly adults were transferred from the serial transfer system to bottles with fresh food for 24 h. Adults 5 days old were placed on egg collecting devices (layers) containing a mixture of agar, water, acetic acid, and ethyl alcohol, with a drop of active yeast on it. Every 2 h., the layer glasses were changed, in this way, the eggs of a glass have similar age, with a maximum difference of 2 h. among them. The glasses of the layers were kept at 25° C. for at least 22 h. in Petri dishes until larvae hatched. Fifty larvae were picked with a lancet under a stereoscopic microscope and were seeded into 10×2 cm vials with 5 ml food. Vials were supplemented with 4a, 5a and 7a at 1, 10 and 100 µg/ml. As positive control we used cupric acetate (toxic) at 350 µg/ml.

The number of adult flies which emerged from each vial was counted daily until the exhaustion of the culture. The parameters studied were the larvae-to-adult viability (V) and development time.

Viability is expressed as V=NA/NL, where NL is the input number of larvae (25 in our case) and NA the output number of adults emerging from these NL larvae. Development time was measured in days by the formula DT=$\Sigma$Nidi/$\Sigma$Ni where Ni is the number of flies emerging on the day di after the larvae were placed in the medium.

The data are expressed as the mean±SEM values from 3 independent experiments involving triplicate vials at the number of flies indicated.

The V and DT of the control larvae were approximately of 85% and 12 days, respectively. The results showed that larvae-to-adult viability and development time were not affected by 4a, 5a and 7a compounds at the tested concentrations (Tables 6, 7 and 8). These results indicate a potential safety profile for these 4a, 5a and 7a compounds, at the doses assayed although, at least for compounds 5a and 7a, the safety profile may reach doses up to 2000 µg/mL.

TABLE 6

Effect of compound 4a (IFC-1102-48S) in larva to adult viability and development time of *Drosophila melanogaster*.

| Compound 4a (µg/ml) | Larva-to-adult viability (% emerged adult flies) | Larva-to adult development days |
|---|---|---|
| 0 | 85.46 ± 2.5 | 11.90 ± 0.2 |
| 1 | 86.19 ± 2.2 | 10.96 ± 0.2 |
| 10 | 79.96 ± 3.9 | 10.37 ± 0.6 |
| 100 | 85.91 ± 1.9 | 10.70 ± 0.1 |
| Cupric acetate (350 µg/ml) | 0 | not applicable |

TABLE 7

Effect of compound 5a (IFC-1102-57S) in larva to adult viability and development time of *Drosophila melanogaster*.

| Compound 5a (µg/ml) | Larva-to-adult viability (% emerged adult flies) | Larva-to adult development days |
|---|---|---|
| 0 | 85.46 ± 2.2 | 11.90 ± 0.2 |
| 1 | 86.91 ± 6.2 | 12.96 ± 0.6 |
| 10 | 93.48 ± 3.0 | 12.12 ± 0.2 |
| 100 | 80.74 ± 4.6 | 11.81 ± 0.5 |
| Cupric acetate (350 µg/ml) | 0 | not applicable |

TABLE 8

Effect of compound 7a (PGP-11048SR1) in larva to adult viability and development time of *Drosophila melanogaster*.

| Compound 7a (µg/ml) | Larva-to-adult viability (% emerged adult flies) | Larva-to adult development days |
|---|---|---|
| 0 | 85.46 ± 2.5 | 11.90 ± 0.2 |
| 1 | 92.23 ± 3.0 | 11.03 ± 0.2 |
| 10 | 92.32 ± 2.6 | 10.51 ± 1.6 |
| 100 | 99.51 ± 4.9 | 11.52 ± 0.4 |
| Cupric acetate (350 µg/ml) | 0 | not applicable |

Example 35

Toxicology Study of Compounds 4a (IFC-1102-48S), 5a (IFC-1102-57S) and 7a (PGP-11048SR1) in a Mice Model The experiments were conducted using female Swiss mice (20-30 g), housed under a 12-h light-dark cycle, with controlled humidity (60-80%), and temperature (22±1° C.). Food and water were freely available to the mice.

Female mice (n=6) were orally (2000 mg/kg) administered with a single dose of 4a, 5a, and 7a for the observation of acute signs of toxicity until 14 days. After treatment, the animals were observed for the first hour, followed by every hour up to 6 h, and subsequently daily for 14 days. The observations comprised the behavior and manifestations of the toxic symptoms, and were carried out according to the Guidelines of the Organization for Economic Cooperation and Development (OECD, 2008).

All compounds were dissolved in sterile saline and were administered by oral gavage to mice based in the weight, for example 20 g received 20 µL.

The data are expressed as mean±S.E.M. of experiments. Statistical significance was determined through one-way analysis of variances (ANOVA), followed by either Newman-Keuls test. A p<0.05 was considered statistically significant. Graphs were drawn and statistical analysis was carried out using GraphPad Prism version 5.00 for Windows (GraphPad Software, San Diego, Calif., USA).

The oral (2000 mg/kg) administration of 4a, 5a or 7a compounds in mice did not produce mortality or any behavioral disorders, after observation for 14 days.

Example 36

Effect of Compounds 23b or 21a in an oral glucose tolerance test performed in normoglycemic rats.

Male Wistar rats (200-300 g) were utilized provided by Mato Grosso do Sul's Federal University's Biotherium. Until the experiments were carried out, the animals have had free access to feed and water. The room temperature was kept at $22\pm2°$ C. with controlled humidity (60-80%) and the light/dark cycle was of 12 hours.

All procedures were submitted to the Animal Experimentation Ethics Committee.

The glucose tolerance test was evaluated as described by Al-Awaki et al (6).

Rats were randomly divided into six groups of four animals that were control group that received only a solution of saline, compound 23b group (10 mg/kg), compound 21a group (10 mg/kg) and metformin 300 mg/kg group. Respective treatments were made orally and daily for five days.

On day 1, 3, and 5, different groups of rats were fasted overnight (at least 12 h) prior to the test, but with given water ad libitum. The oral glucose tolerance test was carried out by administering of a glucose solution (2 g/kg body weight) according to Al-Awadi et al (6). Glycemia was determined in blood samples collected from the tail vein at −30 minutes (just before the administration of the oral extract) time 0 (prior to the glucose overload) and at 60 minutes after the glucose overload. Serum glucose concentrations were measured by the glucose oxidase method (7) using commercial kit (Accuchek-performa (Roche)) according to the manufacture's instructions.

The animals received Compounds 23b or 21a in dose of 10 mg/kg orally in a single dose per day, on the third day there was a significant reduction in glucose levels induced by compounds 23b and 21a (FIG. 7). Similarly, the oral treatment with metformin induces reduction of glycemic levels, but a doses 30 times fold higher (FIG. 11). In the fifth day, only compound 23b and metformin (but at doses 30 times fold higher) reduced the glucose levels in relation to control group.

Example 37

Effect of Compounds 21b, 21e, 23e, 23a, 23d or 26b in an oral glucose tolerance test performed in normoglycemic rats.

Male Wistar rats (200-300 g) were utilized provided by Mato Grosso do Sul's Federal University's Biotherium. Until the experiments were carried out, the animals have had free access to feed and water. The room temperature was kept at $22\pm2°$ C. with controlled humidity (60-80%) and the light/dark cycle was of 12 hours. All procedures were submitted to the Animal Experimentation Ethics Committee.

The glucose tolerance test was evaluated as described by Al-Awaki et al (6).

The compounds 21b, 23a and 23d were diluted firstly in 20 μl of ethanol and after in 980 μl de saline. Compounds 21e, 23e and 26b were dissolved in sterile saline and were administered by oral gavage to rats based in the weight, for example 200 g received 200 μL.

54 rats were randomly divided into seven groups of five-eight animals that were control group (n=8) that received only a solution of vehicle, compound 21b group (n=5) (10 mg/kg), compound 21e group (n=5) (10 mg/kg), compound 23e group (n=5) (10 mg/kg), compound 23a group (n=5) (10 mg/kg), compound 23d group (n=5) (10 mg/kg), compound 26b group (n=5) (10 mg/kg) and metformin (n=6) 300 mg/kg group. Respective treatments were made orally and daily for five days.

On day 1, 3, and 5, different groups of rats were fasted overnight (at least 12 h) prior to the test, but with given water ad libitum. The oral glucose tolerance test was carried out by administering of a glucose solution (2 g/kg body weight) according to Al-Awadi et al (6). Glycemia was determined in blood samples collected from the tail vein at −30 minutes (just before the administration of the oral extract) time 0 (prior to the glucose overload) and at 60 minutes after the glucose overload. Serum glucose concentrations were measured by the glucose oxidase method (7) using commercial kit (Accuchek-performa (Roche)) according to the manufactures's instructions.

The animals received compounds 21b, 21e, 23e, 23d or 26b in dose of 10 mg/kg orally in a single dose per day. On the first day there was a significant reduction in glucose levels induced by compounds 21e, 23e and 23a, and the positive control metformin, but at a doses 30 times fold higher. On the third day there was a significant reduction in glucose levels induced by compounds 21e and 23e and the positive control metformin. In the fifth day, compounds 21b, 21e, 23e, 23d or 26b and metformin (but at a doses 30 times fold higher) reduced the glucose levels in relation to control group (FIG. 8).

REFERENCES

1.—Molina P, Fresneda P M, Garcia-Zafra S, Almendros P. Tetrahedron Letters 1994, 35, 8851.
2.—Moty A, Sakai S, Aimi N, Takayama H, Kitajima M, Shorbagi A, Ahmed A N, Omar N M. European Journal Medicinal Chemistry 1997, 32, 1009.
3.—Grundy S M. Drug therapy of the metabolic syndrome: minimizing the emerging crisis in polypharmacy. Nat Rev Drug Discov. 2006 5(4):295-309.
4.—Crunkhorn (2011). Metabolic disease: Birch bark compound combats metabolic syndrome. Nature Reviews Drug Discovery 10, 175.
5.—Gross J L, Silveiro S P, Camargo J L, Reichelt A J, Azevedo M J. Diabetes Melito: Diagnóstico, Classifição e Avaliação do Controle Glicêmico. Arq Bras Endocrinol Metab 46(1) 2002.
6.—Al-Awadi F M, Khattar M A, Gumaa K A: On the mechanism of the hypoglycaemic effect of a plant extract. Diabetologia. 1985 Jul.; 28(7):432-4.
7.—Trinder P.: Determination of blood glucose using an oxidase-peroxidase system with a non-carcinogenic chromogen. J Clin Pathol. 1969 Mar.; 22(2):158-61.

The invention claimed is:

1. A compound of formula I and any pharmaceutically, cosmetically or food grade acceptable salt thereof.

2. A pharmaceutical composition comprising at least a compound according to claim 1, their pharmaceutically acceptable salts, or combinations thereof and, optionally, at least an inert compound, carrier or excipient.

* * * * *